(12) United States Patent
Pouletty et al.

(10) Patent No.: US 11,992,499 B2
(45) Date of Patent: May 28, 2024

(54) QUINOLINE DERIVATIVES FOR USE IN THE TREATMENT OF INFLAMMATION DISEASES

(71) Applicants: ABIVAX, Paris (FR); INSTITUT CURIE, Paris (FR); UNIVERSITE DE MONTPELLIER, Montpellier (FR); CENTRE NATIONAL DE LA RECHERCHE SCIENTIFIQUE, Paris (FR)

(72) Inventors: Philippe Pouletty, Paris (FR); Hartmut Ehrlich, Paris (FR); Didier Scherrer, Castelnau le Lez (FR); Jamal Tazi, Clapiers (FR)

(73) Assignees: ABIVAX, Paris (FR); INSTITUT CURIE, Paris (FR); UNIVERSITE DE MONTIPELLIER, Montpellier (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 108 days.

(21) Appl. No.: 17/416,856

(22) PCT Filed: Dec. 19, 2019

(86) PCT No.: PCT/EP2019/086477
§ 371 (c)(1),
(2) Date: Jun. 21, 2021

(87) PCT Pub. No.: WO2020/127843
PCT Pub. Date: Jun. 25, 2020

(65) Prior Publication Data
US 2022/0023324 A1    Jan. 27, 2022

(30) Foreign Application Priority Data
Dec. 20, 2018 (EP) ................................ 18306782

(51) Int. Cl.
*A61K 31/706* (2006.01)
*A61P 1/16* (2006.01)
*A61P 9/12* (2006.01)

(52) U.S. Cl.
CPC .............. *A61K 31/706* (2013.01); *A61P 1/16* (2018.01); *A61P 9/12* (2018.01)

(58) Field of Classification Search
None
See application file for complete search history.

(56) References Cited

U.S. PATENT DOCUMENTS 2,605,182 A    7/1952   Peterson
4,376,202 A    3/1983   Ura et al.
(Continued)

FOREIGN PATENT DOCUMENTS

DE    958 647 C        2/1957
EP    0 394 112 A2    10/1990
(Continued)

OTHER PUBLICATIONS

Aberg, Judith A. "Aging, inflammation, and HIV infection." Topics in antiviral medicine 20.3 (2012): 101.*
(Continued)

*Primary Examiner* — Patrick T Lewis
(74) *Attorney, Agent, or Firm* — Oliff PLC

(57) ABSTRACT

A compound of Formula (I):

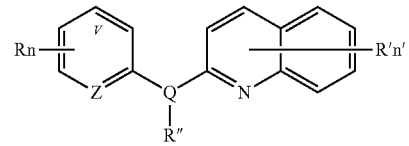

or anyone of its metabolites or a pharmaceutically acceptable salt thereof, for use for treating and/or preventing an inflammatory disease, disorder or condition, wherein each R is independently hydrogen, halogen, —CN, hydroxyl, ($C_1$-$C_3$)fluoroalkyl, ($C_1$-$C_3$)fluoroalkoxy, ($C_3$-$C_6$)cycloalkyl, —$NO_2$, —$NR_1R_2$, ($C_1$-$C_4$)alkoxy, phenoxy, —$NR_1$—$SO_2$—$NR_1R_2$, —$NR_1$—$SO_2$—R1, —$NR_1$—C(=O)—$R_1$, —$NR_1$—C(=O)—$NR_1R_2$, —$SO_2$—$NR_1R_2$, —$SO_3H$, —O—$SO_2$—$OR_3$, —O—P(=O)—($OR_3$)($OR_4$), —O—$CH_2$—$COOR_3$, ($C_1$-$C_3$)alkyl; each R' is independently hydrogen, (C1-C3)alkyl, hydroxyl, halogen, —$NO_2$, —$NR_1R_2$, morpholinyl, morpholino, N-methylpiperazinyl, ($C_1$-$C_3$)fluoroalkyl, ($C_1$-$C_4$)alkoxy, —O—P(=O)—($OR_3$)($OR_4$), —CN, a —NH—$SO_2$—N($CH_3$)$_2$ group, or other groups and further relates to A compound of formula (IV):

(IV)

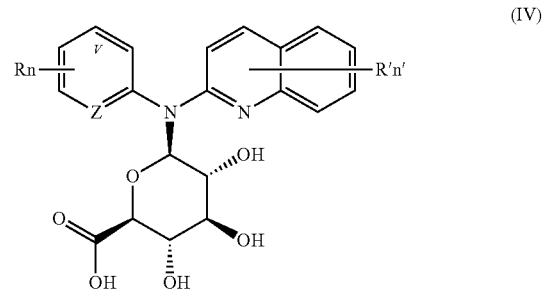

or a pharmaceutically acceptable salt thereof, for use for treating and/or preventing an inflammatory disease, disorder or condition, wherein V, Z, R, R', n, and n' are as described above.

38 Claims, 3 Drawing Sheets

(56) References Cited

U.S. PATENT DOCUMENTS

| | | | |
|---|---|---|---|
| 4,425,343 A | 1/1984 | Sakata et al. | |
| 4,434,290 A | 2/1984 | Bisagni et al. | |
| 4,738,710 A | 4/1988 | Serban et al. | |
| 6,180,632 B1 | 1/2001 | Myers et al. | |
| 7,019,147 B1 | 3/2006 | Barth et al. | |
| 8,394,796 B2 | 3/2013 | Castanedo et al. | |
| 8,933,033 B2 | 1/2015 | Naylor et al. | |
| 8,957,065 B2 | 2/2015 | Cha et al. | |
| 9,061,999 B2 * | 6/2015 | Tazi | A61P 31/18 |
| 9,108,919 B2 | 8/2015 | Roux et al. | |
| 9,145,367 B2 | 9/2015 | Tazi et al. | |
| 9,637,475 B2 | 5/2017 | Roux et al. | |
| 9,827,237 B2 | 11/2017 | Tazi et al. | |
| 10,017,498 B2 | 7/2018 | Tazi et al. | |
| 10,253,020 B2 | 4/2019 | Tazi et al. | |
| 10,435,370 B2 | 10/2019 | Tazi et al. | |
| 10,683,284 B2 | 6/2020 | Tazi et al. | |
| 10,981,874 B2 | 4/2021 | Scherrer et al. | |
| 2003/0207886 A1 | 11/2003 | Plucker et al. | |
| 2004/0038969 A1 | 2/2004 | Doherty et al. | |
| 2004/0242603 A1 | 12/2004 | Fujiwara et al. | |
| 2005/0085482 A1 | 4/2005 | Ramurthy et al. | |
| 2005/0119225 A1 | 6/2005 | Schumacher et al. | |
| 2006/0089380 A1 | 4/2006 | Barnham et al. | |
| 2008/0119478 A1 | 5/2008 | Tsubouchi et al. | |
| 2008/0161353 A1 | 7/2008 | Barnham et al. | |
| 2008/0318984 A1 | 12/2008 | Verkman et al. | |
| 2009/0227628 A1 | 9/2009 | Kolczewski et al. | |
| 2010/0167948 A1 | 7/2010 | Krichevsky et al. | |
| 2011/0003843 A1 | 1/2011 | Lejeune et al. | |
| 2011/0111976 A1 | 5/2011 | Fare et al. | |
| 2012/0202870 A1 | 8/2012 | Weiner et al. | |
| 2012/0277230 A1 | 11/2012 | Roux et al. | |
| 2012/0283265 A1 | 11/2012 | Tazi et al. | |
| 2012/0329796 A1 | 12/2012 | Tazi et al. | |
| 2013/0040988 A1 | 2/2013 | Deka et al. | |
| 2013/0267703 A1 | 10/2013 | Tazi et al. | |
| 2014/0051085 A1 | 2/2014 | Ding et al. | |
| 2014/0080831 A1 | 3/2014 | Roux et al. | |
| 2014/0288120 A1 | 9/2014 | Tazi et al. | |
| 2015/0225796 A1 | 8/2015 | Snijders et al. | |
| 2015/0299129 A1 | 10/2015 | Roux et al. | |
| 2015/0307478 A1 | 10/2015 | Tazi et al. | |
| 2015/0361491 A1 | 12/2015 | Tazi et al. | |
| 2016/0041153 A1 | 2/2016 | Brown et al. | |
| 2017/0204063 A1 | 7/2017 | Tazi et al. | |
| 2017/0226095 A1 | 8/2017 | Tazi et al. | |
| 2018/0030078 A1 | 2/2018 | Scherrer et al. | |
| 2019/0077760 A1 | 3/2019 | Rabe et al. | |
| 2019/0382347 A1 | 12/2019 | Scherrer et al. | |
| 2020/0062713 A1 | 2/2020 | Rabe et al. | |
| 2021/0047273 A1 | 2/2021 | Scherrer et al. | |
| 2021/0087145 A1 | 3/2021 | Tazi et al. | |

FOREIGN PATENT DOCUMENTS

| | | | |
|---|---|---|---|
| EP | 1 897 914 A1 | 3/2008 | |
| EP | 2 075 309 A2 | 7/2009 | |
| EP | 2 266 972 A1 | 12/2010 | |
| EP | 2 465 502 A1 | 6/2012 | |
| EP | 2 757 161 A1 | 7/2014 | |
| EP | 2 974 729 A1 | 1/2016 | |
| EP | 3 059 236 A1 | 8/2016 | |
| FR | 2 387 229 A1 | 11/1978 | |
| FR | 2 436 786 A1 | 4/1980 | |
| FR | 2 627 493 A1 | 8/1989 | |
| FR | 2 645 861 A1 | 10/1990 | |
| FR | 2 849 474 A3 | 7/2004 | |
| FR | 2 859 474 A1 | 3/2005 | |
| FR | 2 859 475 A1 | 3/2005 | |
| GB | 585362 A | 2/1947 | |
| GB | 2087387 A | 5/1982 | |
| IN | 554/CHE/2003 | 4/2005 | |
| JP | S52-72821 A | 6/1977 | |
| JP | S56-051454 A | 5/1981 | |
| JP | H09-508642 A | 9/1997 | |
| JP | 2005-507365 A | 3/2005 | |
| JP | 2006-504646 A | 2/2006 | |
| JP | 2006-519846 A | 8/2006 | |
| JP | 2008-519814 A | 6/2008 | |
| JP | 2009-174368 A | 8/2009 | |
| JP | 6378802 B2 | 8/2018 | |
| WO | 95/21613 A1 | 8/1995 | |
| WO | 00/59875 A2 | 10/2000 | |
| WO | 2002/074726 A2 | 9/2002 | |
| WO | 02/083643 A1 | 10/2002 | |
| WO | 03/000660 A1 | 1/2003 | |
| WO | 2003/037866 A1 | 5/2003 | |
| WO | 2004/007461 A1 | 1/2004 | |
| WO | 2004/078731 A1 | 9/2004 | |
| WO | 2004/080463 A1 | 9/2004 | |
| WO | 2005/023255 A2 | 3/2005 | |
| WO | 2005/051302 A2 | 6/2005 | |
| WO | 2005/112930 A1 | 12/2005 | |
| WO | 2006/051311 A1 | 5/2006 | |
| WO | 2006/060318 A2 | 6/2006 | |
| WO | 2006/081444 A2 | 8/2006 | |
| WO | 2007/000876 A1 | 1/2007 | |
| WO | 2007/042899 A2 | 4/2007 | |
| WO | 2007/103162 A2 | 9/2007 | |
| WO | 2007/147217 A1 | 12/2007 | |
| WO | 2008/003864 A1 | 1/2008 | |
| WO | 2008/008234 A1 | 1/2008 | |
| WO | 2008/089459 A1 | 7/2008 | |
| WO | 2008/101935 A2 | 8/2008 | |
| WO | 2008/115870 A2 | 9/2008 | |
| WO | 2008/118468 A1 | 10/2008 | |
| WO | 2008/143440 A1 | 11/2008 | |
| WO | 2009/021696 A1 | 2/2009 | |
| WO | 2009/023844 A2 | 2/2009 | |
| WO | 2009/029617 A1 | 3/2009 | |
| WO | 2009/085234 A2 | 7/2009 | |
| WO | 2009/087238 A2 | 7/2009 | |
| WO | 2009/132273 A2 | 10/2009 | |
| WO | 2010/107965 A1 | 9/2010 | |
| WO | 2010/127208 A1 | 11/2010 | |
| WO | 2010/129451 A1 | 11/2010 | |
| WO | 2010/143168 A2 | 12/2010 | |
| WO | 2010/143169 A2 | 12/2010 | |
| WO | 2010/143170 A2 | 12/2010 | |
| WO | 2010/151755 A2 | 12/2010 | |
| WO | WO-2010143169 A2 * | 12/2010 | A61K 31/4709 |
| WO | 2011/057003 A2 | 5/2011 | |
| WO | 2012/080953 A1 | 6/2012 | |
| WO | 2014/055944 A1 | 4/2014 | |
| WO | 2014/111892 A1 | 7/2014 | |
| WO | 2015/001518 A1 | 1/2015 | |
| WO | 2015/131019 A1 | 9/2015 | |
| WO | 2016/009065 A2 | 1/2016 | |
| WO | 2016/009066 A1 | 1/2016 | |
| WO | 2016/135055 A1 | 9/2016 | |
| WO | WO-2016135052 A1 * | 9/2016 | A61K 31/4709 |
| WO | 2017/158201 A1 | 9/2017 | |

OTHER PUBLICATIONS

Gavegnano, Christina, et al. "Ruxolitinib and tofacitinib are potent and selective inhibitors of HIV-1 replication and virus reactivation in vitro." Antimicrobial agents and chemotherapy 58.4 (2014): 1977-1986.*
CAS Registry No. 438481-24-4 added on STN on Jul. 12, 2002.
CAS Registry No. 933238-11-0 added on STN on Apr. 29, 2007.
Connor et al., "Vpr is Required for Efficient Replication of Human Immunodeficiency Virus type-1 in Mononuclear Phagocytes," Virology, 1995, vol. 206, pp. 935-944.
Cottet et al., "Recommendable Routes to Trifluoromethyl-Substituted Pyridine-and Quinolinecarboxylic Acids," Eur. J. Org. Chem., 2003, pp. 1559-1568.
Database CAS Registry of RN 1019446-43-5. Retreived 2020.
Database CAS Registry of RN 1094714-12-1. Retreived 2020.
Database CAS Registry of RN 1457614-02-6. Retreived Feb. 2020.
Database CAS Registry of RN 1548036-82-3. Retreived 2020.

(56) References Cited

OTHER PUBLICATIONS

Database CAS Registry of RN 1556532-05-8. Retreived Feb. 2020.
Database CAS Registry of RN 298216-45-2. Retreived 2020.
Database CAS Registry of RN 338749-91-0. Retreived Feb. 2020.
Database CAS Registry of RN 338750-07-5, RN 338749-97-6, and RN 338417-00-8 (2001).
Database CAS Registry of RN 448932-63-6. Retreived Feb. 2020.
Database CAS Registry of RN 478032-29-0. Retreived Feb. 2020.
Database CAS Registry of RN 926207-30-9. Retreived 2020.
De Sandre-Giovannoli et al. "Lamin a Truncation in Hutchinson-Gilford Progeria". Science, vol. 300, p. 2055, 2003.
De Sandre-Giovannoli et al., "Altered Splicing in Prelamin A-associated Premature Aging Phenotypes," Progress in Molecular and Subcellular Biology, 2006, pp. 199-232.
Derrick D. Eichele et al. "Dextran sodium sulfate colitis murine model: An indispensable tool for advancing our understanding of inflammatory bowel diseases pathogenesis." World Journal of Gastroenterology, No. 33, vol. 23, Sep. 2017, pp. 6016-6029.
Desai et al., "2-Methyl-4-quinoline-hydrazide Derivatives as Antitubercular/Antibacterial Agents—Part I," Asian Journal of Chemistry, vol. 10, No. 2, (1998), pp. 370-372.
Desai et al., "Some Quinoline, Quinazoline and Pyrazine Derivatives as Antitubercular-Antibacterial Agents," Asian Journal of Chemistry, vol. 10, No. 4 (1998), pp. 993-994.
Deuerleine, "Dipryridyl-, diquinolyl-, and Pyridylquinolylamines," Journal fuer Praktische Chemie (Liepzig), 1923, vol. 106, pp. 53-65.
Dhanabal et al., "Heteroatom Directed Photoannulation: Synthesis of Indoloquinoline Alkaloids: Cryptolepine, Cryptotackieine, Cryptosanguinolentine, and their Methyl Derivatives," Tetrahedron, 2006, vol. 62, pp. 6258-6263.
Dignam et al., "Eukaryotic Gene Transcription with Purified Components," Methods in Enzymology, 1983, vol. 101, pp. 582-598.
Dobson, J. et al., "Attempts to find new antimalarials. XXVII. Derivatives of various benzacridines and pyridoacridines", Journal of the Chemical Society, pp. 123-126, Jan. 1948.
Ducrocq et al., "Synthesis of 10-substituted 5H-pyrido[3', 4':4,5]pyrrolo[2,3-]isoquinolines," Journal of the Chemical Society, Perkin Transactions 1: Organic and Bio-Organic Chemistry (1972-1999), 1979, vol. 1, pp. 142-145.
Dudash et al., "Synthesis and Evaluation of 3-anilio-quinoxalinones as glycogen phosphorlyase inhibitors", Bioorganic & Medicinal Chemistry Letters, 15(21), p. 4790-4793, 2005.
Edwards et al., "Orf-I amd Orf-II-Encoded Proteins in HTLV-1 Infection and Persistence", Viruses, 2011, MDPI, vol. 3, pp. 861-885.
El-Sayed et al. "Synthesis of Some Novel Quinoline-3-Carboxylic Acids and Pyrimidoquinoline Derivatives as Potential Antimicrobial Agents". Archiv der Pharmize, vol. 335, No. 9, pp. 403-410, 2002.
Etukala et al., "A Short and Convenient Synthesis and Evaluation of the Antiinfective Properties of Indoloquinoline Alkaloids: 10H-Indolo[3,2-b]quinoline and 7H-Indolo[2,3-c]quinolines," Journal of Heterocyclic Chemistry, No. 45, Mar. 2008, pp. 507-511.
Ewing et al., "Analysis of Expressed Sequence Tags Indicates 35,000 Human Genes," Nature Genetics, 2000, vol. 25, pp. 232-234.
F. J. Leinweber, "Possible Physiological Roles of Carboxylic Ester Hydrolases," Drug Metabolism Reviews, vol. 18, No. 4, pp. 379-439, 1987.
Fangfang Jin et al. "Serum microRNA Profiles Serve as Novel Biomarkers for Autoimmune Diseases." Frontiers in Immunology, vol. 9, Oct. 2018, pp. 1-9.
Fengmao An et al. "MiR-124 acts as a target for Alzheimer's disease by regulating BACE1." Oncotarget, No. 69, vol. 8, 2017, pp. 114065-114071.
File Registry on STN, 101350-67-8, entered on Apr. 5, 1986.
File Registry on STN, 195876-33-6/RN, entered on Oct. 23, 1997.
File Registry on STN, 408510-56-5, entered on Apr. 29, 2002.
File Registry on STN, 55360-88-8, entered on Nov. 16, 1984.
File Registry on STN, 67412-46-8, entered on Nov. 16, 1984.
File Registry on STN, 70125-24-5/RN, entered on Nov. 16, 1984.
File Registry on STN, 92873-44-4, entered on Dec. 7, 1984.
File Registry on STN, 94541-69-2, entered on Feb. 3, 1985.
File Registry on STN, 97978-62-6, entered on Sep. 16, 1985.
Fong et al., "A Protein Farnesyltransferase Inhibitor Ameliorates Disease in a Mouse Model of Progeria," Science, 2006, vol. 311, pp. 1621-1623.
Fors et al., "An Efficient Process for Pd-Catalyzed C—N Cross-Coupling Reactions of Aryl Iodides: Insight Into Controlling Factors," J. Am. Chem. Soc., 2009, 131, 5766-5768.
G. Bhattancharjee et al. "Synthesis of physiologically important quinoxaline derivatives using conventional method and microwave irradiation." Indian Journal of Chemical Technology, Council of Scientific & Industrial Research, vol. 15, No. 1, Jan. 2008, pp. 72-74.
Georgios Koukos et al., "MicroRNA-124 Regulates STAT3 Expression and Is Down-regulated in Colon Tissues of Pediatric Patients With Ulcerative Colitis," Gastroenterology, vol. 145, No. 4, Oct. 2013, pp. 842-852.
Gordon et al., "Hutchinson-Gilford Progeria Syndrome," NCBI Bookshelf, 2003, accessed Http://www.ncbi.nlm.gov/books/NBK1121/ on Jan. 26, 2016,21 pages.
Graveley, "Sorting out the Complexity of SR Protein Functions," RNA, 2000, vol. 6, pp. 1197-1211.
Gritsenko et al., "Synthesis in Phenothiazines. XXXIX. Dimethylpyridophenothiazines," Khimiya Geterotsiklicheskikh Soedinenii, 1975, vol. 1, pp. 50-54.
Grout et al., "Polyazabenzo[a]pyrenes," Journal of the Chemical Society [Section] C: Organic, 1968, vol. 21, pp. 2689-2693.
Sep. 23, 2022 Office Action issued In U.S. Appl. No. 17/113,369.
Sep. 28, 2022 Office Action issued in U.S. Appl. No. 16/994,954.
Eugene D. Ponomarev et al., "MicroRNA-124 Promotes Microglia Quiescence and Suppresses EAE by Deactivating Macrophages via the C/EBP-?-PU.1 Pathway", Nature Medicine, vol. 17, No. 1, Jan. 2011, pp. 64-71.
Yang Sun et al., "MicroRNA-124 Mediates the Cholinergic Anti-Flammatory Action Throught Inhibiting the Production of Pro-Inflammatory Cytokines", Cell Research, vol. 23, No. 11, (2013), pp. 1270-1283.
Alsaidi H et al., "Convenient Synthesis of Heteroaryl Phenyl Ethers from Chloropyridines and Chloroquinolines Using Phase-Transfer Catalysis", Synthesis, Georg Thieme Verlag, Stuttgart, DE, No. 11, (1980), pp. 921-924.
A. Simacek et al. "Preparation and Reactivity of 3-Amino-2,4-dichloroquinoline." Synlett, vol. 23, 2012, pp. 2205-2208.
A.K. El-Damasy et al. "Novel 5-substituted-2-anilinoquinolines with 3-(morpholino or 4-methylpiperazin-1-yl)propoxy moiety as broad spectrum antiproliferative agents: Synthesis, cell based assays and kinase screening." Bioorganic & Medicinal Chemistry Letters, vol. 26, No. 14, May 2016, pp. 3307-3312.
A.L. Wilson et al. "New Trends in Anti-Cancer Therapy: Combining Conventional Chemotherapeutics with Novel Immunomodulators." Current Medicinal Chemistry, vol. 25, No. 36, Dec. 2018, pp. 4758-4784.
Altuvia, et al., "Clustering and conservation patterns of human microRNAs", Nucleic Acids Research, 2005, vol. 33, No. 8, pp. 2697-2706, 2005.
Andreassi et al., "Aclarubicin Treatment Restores SMN Levels to Cells Derived from Type 1 Spinal Muscular Atrophy Patients," Human Molecular Genetics, 2001, vol. 10, No. 24, pp. 2841-2849.
Antonella Amoruso et al. "Immune and central nervous system-related miRNAs expression profiling in monocytes of multiple sclerosis patients." Nautre: Scientific Reports, vol. 10, 2020, url: https://doi.org/10.1038/s41598-020-63282-3.
U.S. Appl. No. 14/761,674, filed Jul. 17, 2015 in the name of Tazi et al.
Audrey Vautrin et al. "Both anti-inflammatory and antiviral properties of novel drug candidate ABX464 are mediated by modulation of RNA splicing." Nautre: Scientific Reports, vol. 9, 2019, url: https://doi.org/10.1038/s41598-018-37813-y.

(56) References Cited

OTHER PUBLICATIONS

Bakkour et al., "Small-Molecule Inhibition of HIV pre-mRNA Splicing as a Novel Antiretroviral Therapy to Overcome Drug Resistance," PLOS Pathogens, 2007, vol. 3, issue 10, pp. 1530-1539.
Baklanov et al., "Photocyclization of (o-haloaryl)hetarylamines," Zhurnal Organicheskoi Khimii, 1991, vol. 27, No. 3, pp. 638-649.
Balkau et al., "Syntheis of Ellipticine Intermediates: 6-Amino-, 6-hydroxy-, and 6-Methoxy-5,8-Dimethylisoquinoline," Australian. J. Chem., 1969, vol. 22, pp. 2489-2492.
Bartel, et al., "MicroRNAs: Target Recognition and Regulatory Functions", Cell, vol. 136, No. 2, pp. 215-233, 2009.
Baskerville, et al., "Microarray profiling of microRNAs reveals frequent coexpression with neighboring miRNAs and host genes", RNA, vol. 11, No. 3, pp. 241-247, 2005.
Belikov, V.G. Pharmaceutical Chemistry. Moscow. MEDpress-inform, 2007, pp. 27-29.
Bisset et al., "Combined effect of zidovudine (ZDV), lamivudine (3TC) and abacavir (ABC) antiretoviral therapy in suppressing in vitro FIV replication," Antiviral Research, 2002, Elsevier, vol. 53 pp. 35-45.
Black, "Mechanisms of Alternative Pre-Messenger RNA Splicing," Annu. Rev. Biochem., 2003, vol. 72, pp. 291-336.
Boganyi et al., "Syntheses of New Quinoline-Containing Heterocyclic Scaffolds Using Inter- and Intramolecular Pd-Catalyzed Amination," Journal of Heterocyclic Chemistry, 2009, vol. 46, No. 1, pp. 33-38.
Brandt et al., "Uncoupling activity and physicochemical properties of derivatives of fluazinam," Biochimica et Biophysica Acta, Protein Structure and Molecular Enzymology, 1101(1): 41-7, 1992, abstract only CA 117:82915.
Brune et al., "Progeria: A New Kind of Laminopathy—Clinical and Molecular Update of the Hutchinson-Gilford Syndrome," 1st European Symposium, 2003.
Buchmann et al., "The Preparation and Reactivity of 4-hydroxy-7-chloroquinaldine," Journal fuer Praktische Chemie, 1962, vol. 17, pp. 135-146.
Bustin, "Absolute quantification of mRNA using real-time reverse transcription polymerase chain reaction assays", Journal of Molecular Endocrinology, vol. 25, pp. 169-193, 2000.
CAPLUS Record for Loriga et al., "Part 7." (Retrieved Nov. 2013).
CAPLUS Record for Loriga et al., "Part 8." (Retrieved Nov. 2013).
Cartegni et al., "Correction of Disease-associated Exon Skipping by Synthetic Exon-specific Activators," Nature Structural Biology, 2003, vol. 10, No. 2, pp. 120-125.
Cartegni et al., "Listening to Silence and Understanding Nonsense: Exonic Mutations that Affect Splicing," Nature Reviews—Genetics, Apr. 2002, vol. 3, pp. 285-298.
Carter et al., "Quinoxalines and related compounds-X-1", Tetrahedron, 34(7), p. 981-988, 1978.
CAS (Chemical Abstracts Service) Registry No. 1011408-51-7, American Chemical Society, added on STN on Apr. 1, 2008, 1 page.
CAS (Chemical Abstracts Service) Registry No. 92873-44-4, American Chemical Society, added on STN on Dec. 7, 1984, 1 page.
CAS (Chemical Abstracts Service) Registry No. 94541-69-2, American Chemical Society, added on STN on Feb. 3, 1985, 1 page.
CAS Registry No. 10562-04-6 added on STN on Nov. 16, 1984.
CAS Registry No. 138386-77-3 added on STN on Jan. 17, 1992.
CAS Registry No. 204851-25-2 added on STN on Apr. 30, 1998.
CAS Registry No. 208661-32-9 added on STN on Jul. 19, 1998.
CAS Registry No. 215589-34-7 added on STN on Dec. 15, 1998.
CAS Registry No. 294668-01-2 added on STN on Oct. 11, 2000.
CAS Registry No. 313266-85-2 added on STN on Jan. 9, 2001.
CAS Registry No. 324526-73-0 added on STN on Feb. 27, 2001.
CAS Registry No. 342653-87-6 added on STN on Jun. 20, 2001.
CAS Registry No. 449780-94-3 added on STN on Sep. 12, 2002.
CAS Registry No. 449780-95-4 added on STN on Sep. 12, 2002.
CAS Registry No. 5468-85-9 added on STN on Nov. 16, 1984.
CAS Registry No. 70682-97-2 added on STN on Nov. 16, 1984.
CAS Registry No. 1004363-48-7 added on STN on Feb. 19, 2008.
CAS Registry No. 1011408-51-7 added on STN on Apr. 1, 2008.
CAS Registry No. 1135230-99-7 added on STN on Apr. 16, 2009.
CAS Registry No. 330663-16-6 added on STN on Apr. 10, 2001.
CAS Registry No. 374598-11-5 added on STN on Dec. 10, 2001.
Pauwels. "Aspects of Successful Drug Discovery and Development". Antiviral Res. vol. 71, pp. 77-89, 2006.
Pendas et al. "Defective Prelamin a Processing and Muscular and Adipocyte Alterations in ZMPSTE24 Metalloproteinsase-Deficient Mice". Nature Genetics, vol. 31, pp. 94-99, 2002.
Perry et al. "AIDS dementia: a review of the literature". Alzheimer Dis. Assoc. Disord. 1, pp. 221-235, (PubMed Abstract 3331119), 1987.
Powell et. al., "Expression, characterisation and mutagensis of the aspartic proteinase from equine infections anaemia virus," European Journal of Biochemistry, 1996, FEBS, vol. 241, pp. 664-674.
Prostakov et al., "Schiff Bases in Syntheses of Substituted Naphthylamines, Napthyridines, Azophenanthrenes, and Benzocarbazole," Khimiya Geterotsiklicheskikh Soedinenii, 1972, vol. 10, pp. 1400-1403.
Rauws et al. "Synthesis of new tetracyclic azaheteroaromatic cores via auto-tandem Pd-catalyzed and one-pot Pd- and Cu-catalyzed double C—N bond formation." Tetrahedron, Elsevier, vol. 66, Jun. 2010. 6958-6964.
Respess et al., "Evaluation of an Ultrasensitive p24 Antigen Assay as a Potential Alternative to Human Immunodeficiency Virus Type 1 RNA Viral Load Assay in Resource-Limited Settings," Journal of Clinical Microbiology, vol. 43, No. 1, pp. 506-508, 2005.
Ricky Maung, et al., "Genetic Knockouts Suggest a Critical Role for HIV Co-Receptors in Models of HIV gp 120-Inducted Brain Injury," J. Neuroimmune Pharmacol, 7(2): 306-318, pp. 2-21, Jun. 2012.
Rolak, Clin Med Res, Jan. 2003, vol. 1 (1), 57-60, 2003.
Ruth M. Murray et al., "The Nitration of Some Aryloxy-2- and -4-methylquinoline. Syntheses of Substanes having possible Antimalarial Action," Journal of the Chemical Society, 1934, pp. 856-860.
S.-L. Tang et al. "MiR-124 regulates osteoblast differentiation through GSK-3? in ankylosing spondylitis." European Review for Medical and Pharmacological Sciences, vol. 22, 2018, pp. 6616-6624.
S.D. Carter et al. "Quinoxalines and Related Compounds—X: The Formation of Indolo[2,3-b]Quinoxalines and 2-p-Aminophenyl-3-Anilinoquinoxalines from 2-Anilinoquinoxalines." Tetrahedron, Pergamon Press, vol. 34, Issue No. 7, 1978, pp. 981-988.
Saari, R., et al. "Microwave-assisted synthesis of quinoline, isoquinoline, quinoxaline and quinazoline derivatives as CB2 receptor agonists." Bioorganic & Medicinal Chemistry. Elservier. vol. 19, Jan. 2011, pp. 939-950.
Sanchez-Martin et al. "Symmetrical Bis-Quinolinium Compounds: New Human Choline Kinase Inhibitors with Antiproliferative Activity against the HT-29 Cell Line". Journal of Medicinal Chemistry, vol. 48, No. 9, pp. 3354-3363, 2005.
Sazani et al. "Modulation of Alternative Splicing by Antisense Oligonucleotides". Prog. Mol. Subcell. Biol., vol. 31, pp. 217-239, 2003.
Sazani et al. "Systemically Delivered Antisense Oligomers Upregulate Gene Expression in Mouse Tissues". Nature Biotechnology, vol. 20, pp. 1228-1233, 2002.
Schmittel et al. "Two Novel Thermal Biradical Cyclizations in Theory and Experiment: New Synthetic Routes to 6H-Indolo[2,3-b]quinolines and 2-Amino-quinolines from Enyne-Carbodiimides." Angewandte Chemie International Edition, Wiley, vol. 37, No. 17, Dec. 1998, pp. 2371-2373.
Scott D. Kuduk et al., "Amiloride derived inhibitors of acid-sensing ion channel-3 (ASIC3)," Bioorganic & Medicinal Chemistry Letters, vol. 19, 2009, pp. 2514-2518.
Scott L. Letendre, et al., "The effects of hepatitis C, HIV, and methamphetamine dependence on neuropsychological performance: biological correlates of disease," AIDS 2005, 19 (suppl 3), pp. S72-S78.
Sharp. "Split Genes and RNA Splicing". Cell, vol. 77, pp. 805-815, 1994.
Silberg et al. "N-Acyl-N, N-Dipyridyl and N-Acyl-N-Pyridyl-N-Quinoyl Amine Based Palladium Complexes. Synthesis, X-Ray

(56) References Cited

OTHER PUBLICATIONS

Structures, Heterogenization and Use in Heck Couplings". Journal of Organmetallic Chemistry, vol. 622, pp. 6-18, 2001.
Bolekhova et al. "Reductive Amination of Quinoline N-Oxide With Aminopyridines and Their N-Tosyl Derivatives". Russian Journal of Organic Chemistry, vol. 38, No. 8, pp. 1192-1194, 2002.
STN Database Registration No. 374598-11-5, Chemical Abstracts Service, American Chemical Society, Registered Oct. 1, 2007, pp. 1-10.
STN Database Registration No. 397881-66-2, Chemical Abstracts Service, American Chemical Society, Registered Mar. 4, 2002, 1 page.
STN Database Registration No. 933238-11-0, Chemical Abstracts Service, American Chemical Society, Registered Apr. 29, 2007, pp. 1-4.
Talik et al., "2-Chloro-3, 5-dinitropyridine. 1. Exchange Reactions of the Chlorine Atom," Bulletin de L'Academie Polonaise des Sciences, Serie Des Sciences Chimiques, 1960, vol. 8, No. 5, pp. 219-222.
Tatyana Veremeyko et al. "IL-4/IL-13-Dependent and Independent Expression of miR-124 and Its Contribution to M2 Phenotype of Monocytic Cells in Normal Conditions and during Allergic Inflammation." Plos One, vol. 8, No. 12, 2013, 13 pages.
Tazi et al. "A Protein That Specifically Recognizes The 3' Splice Site of Mammalian Pre-MRNA Introns is Associated With a Small Nuclear Ribonucleoprotein" Cell, vol. 47, pp. 755-766, 1986.
Tazi et al. "The Spliceosome: A Novel Multi-Faceted Target for Therapy". Trends in Biochemical Sciences, vol. 30, No. 8, pp. 469-478, 2005.
Varela et al., "Combined Treatment with Statins and Aminobisphosphonates Extends Longevity in a Mouse Model of Human Premature Aging," Nature Medicine, 2008, vol. 14, No. 7, pp. 767-772.
Vulliamy et al., "Mutations in the Telomerase Component NHP2 Cause the Premature Ageing Syndrome Dyskeratosis Congenita," PNAS, 2008, vol. 105, No. 23, pp. 8073-8078.
Walker et al., "Rheumatic conditions in human immunodeficiency virus infection," (Rheumatology 2008;47:952-959). (Year: 2008).
Wang et al. "A Direct Intramolecular C—H Amination Reaction Cocatalyzed by Copper (II) and Iron (III) as Part of an Efficient Route for the Synthesis of Pyrido[1,2-a]benzimidazoles from N-Aryl-2-aminopyridines." Journal of the American Chemical Society, ACS Publications, vol. 132, Sep. 2010, pp. 13217-13219.
Wang et al. "Alternative Isoform Regulation in Human Tissue Transcriptomes". Nature, vol. 456, pp. 470-476, 2008.
Wang et al. "SC35 Plays a Role in T Cell Development and Alternative Splicing of CD45". Molecular Cell, vol. 7, pp. 331-342, 2001.
Wang, et al., "Quantitation of mRNA by the polymerase chain reaction", Proc. Natl. Acad. Sci., vol. 86, pp. 9717-9721, 1989.
Witwer, et al., "Relationships of PBMC microRNA expression, plasma viral load, and CD4+ T-cell count in HIV-1-infected elite suppressors and viremic patients", Retrovirology, vol. 9, No. 1, 2012.
Wong, et al., "Real-time PCR for mRNA quantitation", BioTechniques, vol. 39, No. 1, pp. 75-85, 2005.
Kueying Li et al. "Long non-coding RNA NEAT1 overexpression associates with increased exacerbation risk, severity, and inflammation, as well as decreased lung function through the interaction with microRNA-124 in asthma." Journal of Clinical Laboratory Analysis, vol. 34, No. 1, 2019, 9 pages.
Yang Sun et al., "MicroRNA-124 mediates the cholinergic anti-inflammatory action through inhibiting the production of pro-inflammatory cytokines," Cell Research, vol. 23, No. 11, Nov. 2013, pp. 1270-1283.
Yueyuan Xiao et al. "miR124-3p/FGFR2 axis inhibits human keratinocyte proliferation and migration and improve the inflammatory microenvironment in psoriasis." Molecular Immunology, vol. 122, 2020, pp. 89-98.

Zeng, et al., "Epigenetic regulation of miR-124 by Hepatitis C Virus core protein promotes migration and invasion of intrahepatic cholangiocarcinoma cells by targeting SMYD3", FEBS Letters, vol. 586, No. 19, pp. 3271-3278, 2012.
Zhen Qin et al. "miR-124, a potential therapeutic target in colorectal cancer." OncoTargets and Therapy, Dovepress, Dec. 2019, pp. 749-751.
Zhibo Yang et al. "MicroRNA-124 alleviates chronic skin inflammation in atopic eczema via suppressing innate immune responses in keratinocytes." Cellular Immunology, vol. 319, 2017, pp. 53-60.
U.S. Appl. No. 13/993,990, filed Jun. 13, 2013 in the name of Tazi et al.
U.S. Appl. No. 15/552,587, filed Aug. 22, 2017 in the name of Scherrer et al.
U.S. Appl. No. 16/787,471, filed Feb. 11, 2020 in the name of Tazi et al.
U.S. Appl. No. 17/113,369, filed Dec. 7, 2020 in the name of Tazi et al.
Chebli et al. "The Anti-HIV Candidate Abx464 Dampens Intestinal Inflammation by Trigerring IL-22 Production in Activated Macrophages." Scientific Reports, vol. 7, No. 4860, pp. 1-11. 2017.
"Abivax sets its course on colitis and Crohn's." Pharmaphorum, pp. 1-3. Sep. 4, 2018.
May 9, 2022 Office Action issued in U.S. Appl. No. 16/994,954.
May 9, 2022 Office Action issued in U.S. Appl. No. 17/113,369.
Guo, et al., "Haplotype Distribution and Evolutionary Pattern of miR-17 and miR-124 Families Based on Population Analysis", PLoS ONE, vol. 4, Issue 11, 2009.
Hernandez-Lopez et al., "Alternative splicing in human tumour viruses: a therapeutic target?" Biochemical Journal, 2012, Biochemical Society, vol. 445, pp. 145-156.
Hofmann et al., "Htra2-ß1 Stimulates an Exonic Splicing Enhancer and can Restore Full-length SMN Expression to Survival Motor Neuron 2 (SMN2)," PNAS, 2000, vol. 97, No. 17, pp. 9618-9623.
Hostyn et al. "Synthesis of ?- Carbolines Starting from 2,3-Dichloropyridines and Substituted Anilines." Advanced Synthesis & Catalysis, Wiley, vol. 350, Oct. 2008, pp. 2653-2660.
Houzet, et al., "MicroRNAs and human retroviruses," Biochimica et Biophysica Acta, 1809(11-12), pp. 686-693, 2011.
Huang-Kai Peng et al., "Synthesis and anti-HCV activity evaluation of anilinoquinoline derivatives," Bioorganic & Medicinal Chemistry Letters, vol. 22, 2012, pp. 1107-1110.
J. Tazi et al., "Alternative Splicing and Disease," Biochimica et Biophysica Acta, 1792 (2009), 14-26.
J. Wei et al., "miR-124 Inhibits STAT3 Signaling to Enhance T Cell-Mediated Immune Clearance of Glioma," Cancer Research, vol. 73, No. 13, Jul. 1, 2013, pp. 3913-3926.
J. Zugazagoitia et al. "Current Challenges in Cancer Treatment." Clinical Therapeutics, vol. 38, No. 7, May 2016, pp. 1551-1566.
Johnson et al., "Genome-Wide Survey of Human Alternative Pre-mRNA Splicing with Exon Junction Microarrays," Science, vol. 302, pp. 2141-2144, 2003.
Jonckers et al. "Selective Palladium-Catalyzed Aminations of Dicholoropyridines," Tetrahedron, 2001, vol. 57, pp. 7027-7034.
Kaczmarek et al. "Synthesis and Antineoplastic Properties of Some Benzoiso-.Alpha.-Carbolines". Archiv Der Pharmazie, Weinheim, Germany, vol. 321, No. 8, pp. 463-467, 1988.
Katoh et al. "Isolation of the intermediates and improved synthesis of pyrido[1',2':1 ,2]imidazo[4, 5b]pyrazines and -quinoxalines", Heterocycles, 1992, 34(10), p. 1965-1972.
Khalifa. "Hutchinson-Gilford Progeria Syndrome: Report of a Libyan Family and Evidence of Autosomal Recessive Inheritance". Clinical Genetics, vol. 35, pp. 125-132, 1989.
Kher Samir et al., "Microwave Mediated Dearylation of 2-Aryloxy-5-Nitropyridine," Research Journal of Chemical Sciences, vol. 1, No. 6, Sep. 2011, pp. 84-87.
Kim, et al., "Processing of intronic microRNAs", EMBO Journal, vol. 26, No. 3, pp. 775-783, 2007.
Klinck, et al., "Multiple Alternative Splicing Markers for Ovarian Cancer", Cancer Research, vol. 68, No. 3, pp. 657-663 , 2008.
Kondratenko et al. "Bactericidal Activity of Some Derivatives of N-Heteroaromatic Compounds". Mikrobiologichnii Zhurnal, 1934-1977, vol. 40, No. 3, pp. 368-370 (abstract only), 1978.

(56) References Cited

OTHER PUBLICATIONS

Labourier et al. "Recognition of Exonic Splicing Enhancer Sequences by the *Drosophila* Splicing Repressor RSF1". Nucleic Acids Research, vol. 27, No. 11, pp. 2377-2386, 1999.
Lai, et al., "Micro RNAs are complementary to 3' UTR sequence motifs that mediate negative post-transcriptional regulation", Nature Genetics, vol. 30, No. 4, pp. 363-364, 2002.
Lee, et al., "MicroRNA maturation: stepwise processing and subcellular localization", EMBO Journal, vol. 21, No. 17, pp. 4663-4670, 2002.
Lin Min et al., "Nonsense-mediated mRNA decay and tumors," Journal of International Pathology and Clinical Medicine, vol. 26, No. 4, pp. 291-294, Aug. 2016.
Lindow, et al., "Principles and Limitations of Computational MicroRNA Gene and Target Finding", DNA and Cell Biology, vol. 26, No. 5, pp. 339-351, 2007.
Litvickji, P.F. Pathophysiology. Moscow. GEOTAR-MED, vol. 1, 2003, pp. 142-144, 192-200.
Liu et al. "Partial Correction of Endogenous F508 CFTR in Human Cystic Fibrosis Airway Epithelia by Spliceosome-Mediated RNA Trans-Splicing". Nature Biotechnology, vol. 20, pp. 47-52, 2002.
Liu, et al., "The evolution and functional diversification of animal microRNA genes", Cell Research, vol. 18, No. 10, pp. 985-996, 2008.
Lombardino. "Some 3-Arylaminoquinoxaline-2-carboxylic Acids", Journal of Medicinal Chemistry, 9(5), p. 770-771, 1996.
Longping Yao et al. "MicroRNA-124 regulates the expression of MEKK3 in the inflammatory pathogenesis of Parkinson's disease." Journal of Neuroinflammation, vol. 15, No. 13, 2016, pp. 1-19.
Loones et al. "Examination of the Mechanism of the Intramolecular Amination of N-(3-Bromopyridin-2-yl)Azaheteroarylamines and N-(2-Chloropyridin-3-yl)Azaheteroarylamines: A Pd-Catalyzed Amination and/or a Base-Assisted Nucleophilic; Aromatic Substitution?". Tetrahedron, vol. 63, pp. 3818-3825, 2007.
Loones et al. "Synthesis of Pyrido[2, 1:2,3]Imidazo[4,5-B]Quinoline and Pyrido[1,2:1,2]Imidazo[4,5-B] Quinoline and Their Benzo and Aza Analogs via Tandem Catalysis". Tetrahedron, vol. 63, pp. 8954-8961, 2007.
Loriga et al. "Quinoxaline Chemistry. Part 7. 2-[Aminobenzoates]- and 2-[Aminobenzoylglutamate]-Quinoxalines as Classical Antifolate Agents. Synthesis and Evaluation of In Vitro Anticancer, Anti-HIV and Antifungal Activity." Farmaco, vol. 52, pp. 157-166, (PubMed Abstract No. 9212450), 1997.
Loriga et al. "Quinoxaline Chemistry. Part 8. 2-[Anilino]-3-[Carboxy]-6(7)-Substituted Quinoxalines as Non Classical Antifolate Agents. Synthesis and Evaluation of Invitro Anticancer, Anti-HIV and Antifungal Activity". Farmaco, vol. 52, pp. 531-537, 1997.
Maes et al. "The First Rapid Palladium-Catalyzed Aminations of (Azahetero)aryl Chlorides under Temperature-Controlled Microwave Heating." Synlett, Thieme Medical Publishers, No. 12, Sep. 2003, pp. 1822-1825.
Manley et al. "SR Proteins and Splicing Control". Genes & Development, vol. 10, pp. 1569-1579, 1996.
Marc Fakhoury et al. "Inflammatory bowel disease: clinical aspects and treatments." Journal of Inflammation Research, Dovepress, Jun. 2014, pp. 113-120.
MicroRNA-124 Deactivates Human HIV-1-Infected and Classically Activated Macrophages/microglia: Implication for Neurogenesis., J. Neuroimmune Pharmacol (2012), vol. 7, Suppl. 1, pp. S75-S76.
Molina et al., "C=C-Conjugated Carbodiimides as 2-Azadienes in Intramolecular [4+2] Cycloadditions. One-Pot Preparation of Quinoline, alpha-Carboline, and Quinindoline Derivatives," J. Org. Chem., 1992, vol. 57, pp. 929-939.

N.A. Lack et al. "Targeting the Binding Function 3 (BF3) Site of the Human Androgen Receptor through Virtual Screening." Journal of Medicinal Chemistry, vol. 54, No. 24, Dec. 2011, pp. 8563-8573.
Nair, et al., "Virus-encoded micro-RNAs: novel regulators of gene expression", TRENDS in Microbiology, vol. 14, No. 4, pp. 169-175, 2006.
Nguyen et al., "Synthesis and Biological Evaluation of Amino-Substituted Benzo [f]pyrido[4,3-b] and Pyrido [3,4-b] quinoxalines: a New Class of Antineoplastic Agents," Anti-Cancer Drug Design, 1995, vol. 10, No. 4, 277-97.
Nissim-Rafinia et al., "Cellular and Viral Splicing Factors Can Modify the Splicing Pattern of CFTR Transcripts Carrying Splicing Mutations," Human Molecular Genetics, 2000, vol. 9, No. 12, pp. 1771-1778.
Nolan, et al., "Quantification of mRNA using real-time RT-PCR", Nature Protocols, vol. 1, No. 3, pp. 1559-1582, 2006.
O.A. Yanborisova et al., "Derivatives of 2-aminocinchoninic acids: synthesis and antiinflammatory activity," Pharmaceutical Chemistry Journal, vol. 2B, No. 1, 1994, pp. 29-31.
O.A. Yanborisova et al., "Synthesis and antiinflammatory activity of 2-arylaminocinchoninic acids and amides of 1,2-dihydro-2-oxocinchoninic acid," Pharmaceutical Chemistry Journal, vol. 29, No. 6, Jun. 1995, pp. 32-33.
O.A. Yanborisova et al., "Synthesis and study of antiinflammatory and nd analgesic activity of 2-arylaminocinchoninic acid hydrazides and ß-(1-carboxyethylidene)hydrazides." Pharmaceutical Chemistry Journal, vol. 31, No. 6, Jun. 1997, pp. 309-310.
Organ et al. "Pd-Catalyzed Aryl Amination Mediated by Well Defined, N-Heterocyclic Carbene (NHC)-Pd Precatalysts, PEPPSI." Chemistry: A European Journal, Wiley, vol. 14, Feb. 2008, pp. 2443-2452.
Ozsolak, et al., "Chromatin structure analyses identify miRNA promoters", Genes and Development, vol. 22, No. 22, pp. 3172-3183, 2008.
Pacifici, et al., "Cerebrospinal fluid miRNA profile in HIV-encephalitis", Journal of Cellular Physiology, vol. 228, No. 5, pp. 1070-1075, 2013.
Pan et al., "Deep surveying of alternative splicing complexity in the human transcriptome by high-throughput sequencing," Nature Genetics, vol. 40, No. 12, pp. 1413-1415, Dec. 2008.
Park et al. "Efficient Palladium-Catalyzed Amination of Aryl Chlorides Using Dicyclo-Hexylamino[(2,6-Dimethyl)Morpholino]Phenylphosphine as a PN.SUB.2 Ligand". Synthesis, No. 5, pp. 0815-0823, 2009.
Oct. 26, 2021 Office Action issued in U.S. Appl. No. 17/113,369.
Oct. 29, 2021 Office Action issued in U.S. Appl. No. 16/994,954.
Ma et al., "*Mycobacterium bovis* BCG Triggered MyD88 Induces miR-124 Feedback Negatively Regulates Immune Response in Alveolar Epithelial Cells," PLOS ONE, vol. 9, Issue 4, e92419, Apr. 2014, pp. 1-12.
Wang et al., "MicroRNA-124 Controls the Proliferative, Migratory, and Inflammatory Phenotype of Pulmonary Vascular Fibroblasts," Cellular Biology, Circulation Research, Jan. 3, 2014, pp. 67-78.
Peng et al., "Expression Patterns of miR-124, miR-134, miR-132, and miR-21 in an Immature Rat Model and Children and Mesial Temporal Lobe Epilepsy," J Mol Neurosci (2013) 50:291-297.
Zhang, et al., "Expression profiles of miRNAs in polarized macrophages," Inlemational Journal of Molecular Medicine 31: 797-802, 2013.
Sep. 8, 2023 Office Action issued in U.S. Appl. No. 17/746,410.
Mar. 5, 2024 Office Action issued in U.S. Appl. No. 17/746,410.

\* cited by examiner

QUINOLINE DERIVATIVES FOR USE IN THE TREATMENT OF INFLAMMATION DISEASES

BACKGROUND OF THE INVENTION

Inflammation is a protective response by the immune system to tissue damage and infection. However, the inflammatory response, in some circumstances, can damage the body. In the acute phase, inflammation is characterized by pain, heat, redness, swelling and loss of function.

Inflammatory diseases include a wide range of conditions including, inflammatory disease associated with an autoimmune disease, a central nervous system (CNS) inflammatory disease, a joint inflammation disease, an inflammatory digestive tract disease, and inflammatory skin.

Some quinoline derivatives have been described in WO2010/143169, WO2012/080953, WO2016/009065 and WO2016/009066, the contents of which are incorporated herein by reference in their entireties.

SUMMARY OF THE INVENTION

It has now been found that compounds of the present invention, and pharmaceutically acceptable compositions thereof, are useful for the treatment and/or prevention of a variety of inflammatory diseases, disorders or conditions. In one aspect, the present invention provides a method for treating an inflammatory disease, disorder or condition comprising administering to a patient in need thereof a compound of Formula (I).

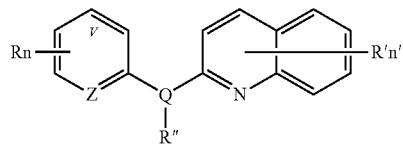

(I)

or a pharmaceutically acceptable salt thereof, wherein each variable is as defined and described herein.

DETAILED DESCRIPTION OF CERTAIN EMBODIMENTS

Figure 1:
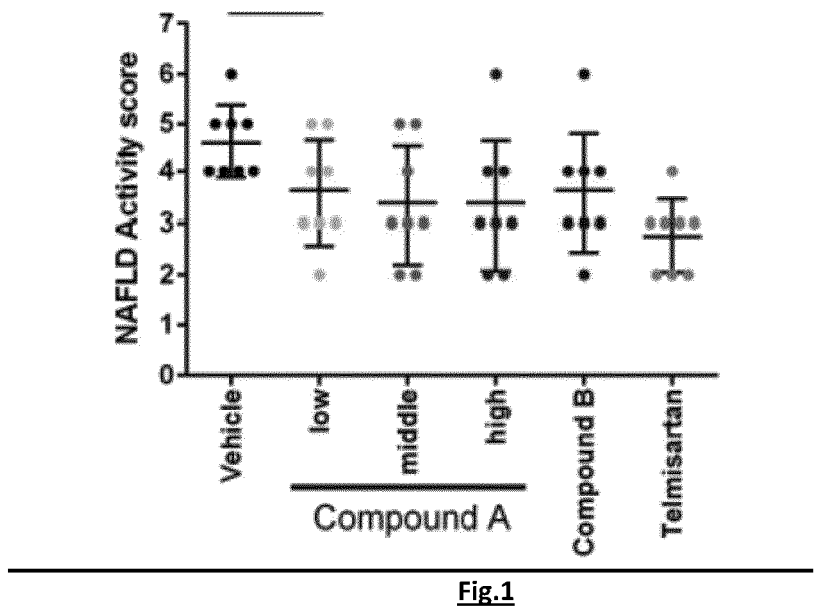
FIG. 1 depicts the NAFLD Activity Score in STAM Model of Non-alcoholic Steatohepatitis (NASH study)

General Description of Certain Embodiments of the Invention

Compounds of the present invention, and pharmaceutical compositions thereof, are useful for treating inflammatory diseases, disorders or conditions, such as those as described herein.

In one aspect, the present invention provides a method for treating an inflammatory disease, disorder or condition comprising administering to a patient in need thereof a compound of Formula (I):

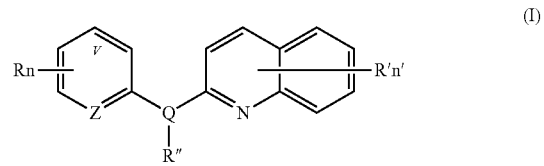

(I)

or a pharmaceutically acceptable salt thereof, wherein: Z is C or N;
V is C or N;

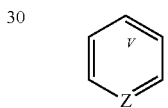

means an aromatic ring wherein V is C or N, and when V is N, V is ortho, meta or para relative to Z;

each R is independently hydrogen, halogen, —CN, hydroxyl, $(C_1$-$C_3)$fluoroalkyl, $(C_1$-$C_3)$fluoroalkoxy, $(C_3$-$C_6)$cycloalkyl, —$NO_2$, —$NR_1R_2$, $(C_1$-$C_4)$alkoxy, phenoxy, —$NR_1$—$SO_2$—$NR_1R_2$, —$NR_1$—$SO_2$—$R_1$, —$NR_1$—C(=O)—$R_1$, —$NR_1$—C(=O)—$NR_1R_2$, —$SO_2$—$NR_1R_2$, —$SO_3H$, —O—$SO_2$—$OR_3$, —O—P(=O)—($OR_3$)($OR_4$), —O—$CH_2$—$COOR_3$, $(C_1$-$C_3)$alkyl, said alkyl being optionally mono- or di-substituted by a hydroxyl group, a group of formula (IIa):

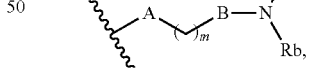

or a group of formula

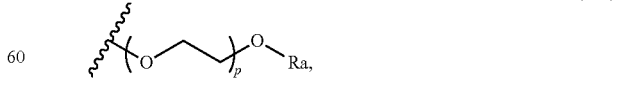

(IIIa)

Q is N or O, provided that R" does not exist when Q is O;
each of $R_1$ and $R_2$ is independently hydrogen or $(C_1$-$C_3)$alkyl;
each of $R_3$ and $R_4$ is independently hydrogen, $Li^+$, $Na^+$, $K^+$, $N^+(Ra)_4$ or benzyl; n is 1, 2 or 3;
n' is 1, 2 or 3;
each R' is independently hydrogen, $(C_1$-$C_3)$alkyl, hydroxyl, halogen, —$NO_2$, —$NR_1R_2$, morpholinyl, morpholino, N-methylpiperazinyl, $(C_1$-$C_3)$fluoroalkyl, $(C_1$-$C_4)$alkoxy, —O—P(=O)—(OR_3)(OR_4), —CN,
or a group of formula (IIa):

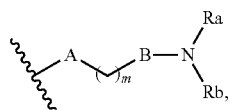

or a group of formula (IIIa):

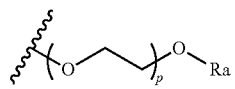

A is a covalent bond, oxygen, or NH;
B is a covalent bond or NH;
m is 1, 2, 3, 4 or 5;
p is 1, 2 or 3; each of Ra and Rb is independently hydrogen, $(C_1$-$C_5)$alkyl, or $(C_3$-$C_6)$cycloalkyl, or
Ra and Rb form together with the nitrogen atom to which they are attached a saturated 5- or 6-membered heterocycle, said heterocycle being optionally substituted by one or more Ra, provided that when R' is a group (IIa) or (IIIa), n' may be 2 or 3 only if other R' groups are different from said group (IIa) or (IIIa); and
R" is hydrogen, $(C_1$-$C_4)$alkyl, or a group of formula (IIa) as defined herein.

According to a further embodiment, the present invention concerns a compound of Formula (I):

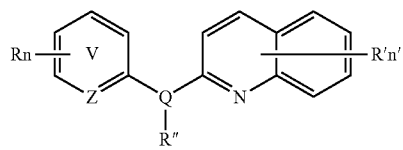

(I)

or anyone of its metabolites or a pharmaceutically acceptable salt thereof, for use for treating and/or preventing an inflammatory disease, disorder or condition wherein:
Z is C or N;
V is C or N;

means an aromatic ring wherein V is C or N, and when V is N, V is ortho, meta or para relative to Z;
each R is independently hydrogen, halogen, —CN, hydroxyl, $(C_1$-$C_3)$fluoroalkyl, $(C_1$-$C_3)$fluoroalkoxy, $(C_3$-$C_6)$cycloalkyl, —$NO_2$, —$NR_1R_2$, $(C_1$-$C_4)$alkoxy, phenoxy, —$NR_1$—$SO_2$—$NR_1R_2$, —$NR_1$—$SO_2$—$R_1$, —$NR_1$—C(=O)—$R_1$, —$NR_1$—C(=O)—$NR_1R_2$, —$SO_2$—$NR_1R_2$, —$SO_3H$, —O—$SO_2$—$OR_3$, —O—P(=O)—$(OR_3)(OR_4)$, —O—$CH_2$—$COOR_3$, $(C_1$-$C_3)$alkyl, said alkyl being optionally mono- or di-substituted by a hydroxyl group or a group of formula (IIa):

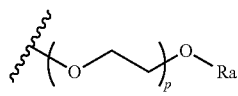

or a group of formula (IIIa):

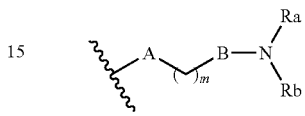

Q is N or O, provided that R" does not exist when Q is O;
each of $R_1$ and $R_2$ is independently hydrogen or $(C_1$-$C_3)$alkyl;
each of $R_3$ and $R_4$ is independently hydrogen, Li⁺, Na⁺, K⁺, N⁺$(Ra)_4$ or benzyl;
n is 1, 2 or 3;
n' is 1, 2 or 3;
each R' is independently hydrogen, $(C_1$-$C_3)$alkyl, hydroxyl, halogen, —$NO_2$, —$NR_1R_2$, morpholinyl, morpholino, N-methylpiperazinyl, $(C_1$-$C_3)$fluoroalkyl, $(C_1$-$C_4)$alkoxy, —O—P(=O)—$(OR_3)(OR_4)$, —CN, a —NH—$SO_2$—N$(CH_3)_2$ group, a group of formula (IIa):

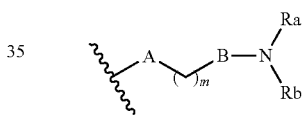

or a group of formula (IIIa):

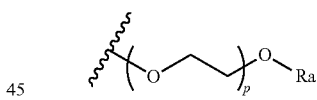

A is a covalent bond, oxygen, or NH; B is a covalent bond or NH;
m is 1, 2, 3, 4 or 5;
p is 1, 2 or 3;
each of Ra and Rb is independently hydrogen, $(C_1$-$C_5)$alkyl, or $(C_3$-$C_6)$cycloalkyl, or Ra and Rb form together with the nitrogen atom to which they are attached a saturated 5- or 6-membered heterocycle, said heterocycle optionally containing a further heteroatom chosen among N, O, S, said heterocycle being optionally substituted by one or more Ra, provided that when R' is a group (IIa) or (IIIa), n' may be 2 or 3 only if other R' groups are different from said group (IIa) or (IIIa); and
R" is hydrogen, $(C_1$-$C_4)$alkyl, or a group of formula (IIa) as defined herein, wherein the inflammatory disease, disorder or condition is selected from:
(a) an inflammatory disease, disorder, or condition in the pancreas selected from diabetes type-1, diabetes type-2, acute and chronic pancreatitis;

(b) an inflammatory disease, disorder, or condition in the kidney selected from glomerulosclerosis, glomerulonephritis, nephritis, acute kidney injury, Berger's disease, Goodpasture's syndrome, Wegener's granulomatosis and kidney transplant acute or chronic rejection;
(c) an inflammatory disease, disorder, or condition in the liver selected from nonalcoholic steatohepatitis (NASH), non-alcoholic fatty liver disease (NAFLD), cholestatic liver disease, sclerosing cholangitis and liver transplant acute or chronic rejection;
(d) an inflammatory disease, disorder, or condition in the lung or heart selected from chronic obstructive pulmonary disease (COPD), pulmonary fibrosis, pulmonary hypertension, sarcoidosis, myocarditis, pericarditis and lung or heart transplant acute or chronic rejection;
(e) an inflammatory disease, disorder, or condition in the skin selected from contact dermatitits, atopic dermatitis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, acnea, keloid scar, and other inflammatory or allergic conditions of the skin;
(f) an inflammatory disease, disorder, or condition in the vessel/blood selected from Behcet's disease, vasculitis, sepsis, tumor angiogenesis, proliferative vascular disease and restenosis;
(g) an inflammatory disease, disorder, or condition in the eye selected from conjunctivitis, scleritis, episcleritis, panuveitis, choroiditis, chorioretinitis, neuroretinitis, uveitis, orbital inflammatory disease, and optical neuritis;
(h) an inflammatory disease, disorder, or condition in the central or peripheral nervous system selected from non-viral and viral encephalitis and meningitis, depression, neuropathic pain, including chronic pain, traumatic brain injury, including stroke, Parkinson disease, Myelitis, Charcot-Marie-Tooth disease type 1 (including CMT1A and CMT1B), Amyotrophic lateral sclerosis (ALS), Creutzfeldt-Jakob disease, demyelinating polyneuropathy and peripheral neuropathy;
(i) an autoimmune disease, disorder, or condition selected from Lupus, including in the skin and kidney, Guillain-Barre syndrome, Myasthenia gravis, Hashimoto's thyroiditis, idiopathic purpura, aplastic anemia, Graves disease, and Myocarditis;
(k) an inflammatory disease, disorder, or condition in the reproductive system selected from endometriosis, uterine fibroma, prostate dysplasia or growth, and cervix dysplasia; and
(l) an inflammatory disease, disorder, or condition in the bone and/or joints selected from juvenile idiopathic arthritis, psoriatic arthritis, periodontitis, and hand, foot, ankle, knee, hip, shoulder, elbow or spine arthritis and/or demineralization.

The present invention moreover relates to a method of preventing, inhibiting or treating said inflammatory diseases as defined above, which comprises at least one step consisting in administering to a patient suffering therefrom an effective amount of a compound as defined in formulas (I), (Ib), (Ib'), (IV), (IVb) or (IVb') below or a pharmaceutically acceptable salt thereof.

Compounds and Definitions

In the framework of the present invention, the following definitions may be given:

effective amount: amount of a pharmaceutical compound which produces an effect on the tumour treated and/or to an amount of a compound of the present invention which is effective in preventing, reducing, eliminating, treating or controlling the symptoms of the herein-described diseases and conditions. The term "effective amount" includes "prophylaxis-effective amount" as well as "treatment-effective amount"; The term "prophylaxis-effective amount" refers to a concentration of compound of this invention that is effective in inhibiting, preventing, decreasing the likelihood of an inflammatory disease;

The term "patient," as used herein, means an animal, preferably a mammal, and most preferably a human;

In the context of the invention, the term "treating" or "treatment", as used herein, means reversing, alleviating, inhibiting the progress of, or preventing inflammatory disease.

The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment.

The term "preventing", as used herein, means reducing the risk of onset or slowing the occurrence of a given phenomenon, namely in the present invention, an inflammatory disease. As used herein, «preventing» also encompasses «reducing the likelihood of occurrence» or «reducing the likelihood of reoccurrence».

The compounds of the invention may exist in the form of free bases or of addition salts with pharmaceutically acceptable acids. Suitable physiologically acceptable acid addition salts of compounds of the present invention include sulfate, hydrobromide, citrate, trifluoroacetate, ascorbate, hydrochloride, tartrate, triflate, maleate, mesylate, formate, acetate, fumarate and sulfonate, in particular alkylsufonate or arylsulfonate, and more particularly mesylate, triflate, edisylate, besylate and tosylate.

The compounds of the present invention and or salts thereof may form solvates or hydrates and the invention includes all such solvates and hydrates. The terms "hydrates" and "solvates" simply mean that the compounds according to the invention can be in the form of a hydrate or solvate, i.e. combined or associated with one or more water or solvent molecules. This is only a chemical characteristic of such compounds, which can be applied for all organic compounds of this type.

The compounds of the present invention can comprise one or more asymmetric carbon atoms. They can thus exist in the form of enantiomers or of diastereoisomers. These enantiomers, diastereoisomers and their mixtures, including the racemic mixtures, are encompassed within the scope of the present invention.

In the context of the present invention, the term:
"halogen" is understood to mean chlorine, fluorine, bromine, or iodine, and in particular denotes chlorine, fluorine or bromine,
"$(C_1-C_5)$alkyl" as used herein respectively refers to $C_1-C_5$ normal, secondary or tertiary saturated hydrocarbon. Examples are, but are not limited to, methyl, ethyl, 1-propyl, 2-propyl, butyl, pentyl,
"$(C_3-C_6)$cycloalkyl" as used herein respectively refers to cyclic saturated hydrocarbon.
Examples are, but are not limited to cyclopropyl, cyclobutyl, cyclopentyl, cyclohexyl, "(C$_1$-C$_4$)alkoxy" as used herein respectively refers to O—(C$_1$-C$_4$)alkyl moiety, wherein alkyl is as defined above. Examples are, but are not limited to, methoxy, ethoxy, 1-propoxy, 2-propoxy, butoxy, "fluoroalkyl group" and "fluoroalkoxy group" refers respectively to alkyl group and alkoxy group as above-defined, said groups being substituted by at least one fluorine atom. Examples are perfluoroalkyl groups, such as trifluoromethyl or perfluoropropyl, "saturated 5- or 6-membered heterocycle" as used herein respectively refers to a saturated cycle comprising at least one heteroatom. Examples are, but are not limited to, morpholine, piperazine, thiomorpholine, piperidine, pyrrolidine.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases.

Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

DESCRIPTION OF EXEMPLARY EMBODIMENTS

In one aspect, the present invention provides a method for treating an inflammatory disease, disorder or condition comprising administering to a patient in need thereof a compound of Formula (I):

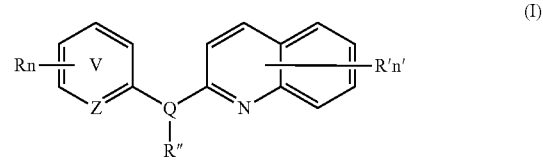

or a pharmaceutically acceptable salt thereof, wherein:
Z is C or N;
V is C or N

means an aromatic ring wherein V is C or N and when V is N, V is ortho, meta or para relative to Z;

each R is independently hydrogen, halogen, —CN, hydroxyl, (C$_1$-C$_3$)fluoroalkyl, (C$_1$-C$_3$)fluoroalkoxy, (C$_3$-C$_6$) cycloalkyl, —NO$_2$, —NR$_1$R$_2$, (C$_1$-C$_4$)alkoxy, phenoxy, —NR$_1$—SO$_2$—NR$_1$R$_2$, —NR$_1$—SO$_2$—R$_1$, —NR$_1$—C(=O)—R$_1$, —NR$_1$—C(=O)—NR$_1$R$_2$, —SO$_2$—NR$_1$R$_2$, —SO$_3$H, —O—SO$_2$—OR$_3$, —O—P(=O)—(OR$_3$)(OR$_4$), —O—CH$_2$—COOR$_3$, (C$_1$-C$_3$)alkyl, said alkyl being optionally mono- or di-substituted by a hydroxyl group, a group of formula (IIa); or a group of formula or a group of formula (IIIa); P

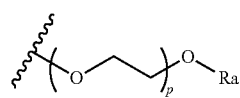

Q is N or O, provided that R" does not exist when Q is O;
each of R$_1$ and R$_2$ is independently hydrogen or (C$_1$-C$_3$) alkyl;
each of R$_3$ and R$_4$ is independently hydrogen, Li$^+$, Na$^+$, K$^+$, N$^+$(Ra)$_4$, or benzyl;
n is 1, 2 or 3;
n' is 1, 2 or 3;

each R' is independently hydrogen, $(C_1-C_3)$alkyl, hydroxyl, halogen, $-NO_2$, $-NR_1R_2$, morpholinyl, morpholino, N-methylpiperazinyl, $(C_1-C_3)$fluoroalkyl, $(C_1-C_4)$alkoxy, $-O-P(=O)-(OR_3)(OR_4)$, $-CN$, a group of formula (IIa):

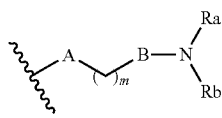

or a group of formula (IIIa): Om R

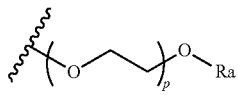

A is a covalent bond, oxygen, or NH;
B is a covalent bond or NH;
m is 1, 2, 3, 4 or 5;
p is 1, 2 or 3;
each of Ra and Rb is independently hydrogen, $(C_1-C_5)$alkyl, or $(C_3-C_6)$cycloalkyl, or
Ra and Rb form together with the nitrogen atom to which they are attached a saturated 5- or 6-membered heterocycle, said heterocycle being optionally substituted by one or more Ra, provided that when R' is a group (IIa) or (IIIa), n' may be 2 or 3 only if other R' groups are different from said group (IIa) or (IIIa); and
R" is hydrogen, $(C_1-C_4)$alkyl, or a group of formula (IIa) as defined above.

As defined generally above, Z is C or N.
In some embodiments, Z is C. In some embodiments, Z is N.
In some embodiments, Z is selected from those depicted in Tables 1-3, below.
As defined generally above, V is C or N.
In some embodiments, V is C. In some embodiments, V is N.
In some embodiments, V is selected from those depicted in Tables 1-3, below.
As defined generally above,

means an aromatic ring wherein V is C or N and when V is N, V is ortho, meta or para relative to Z.
In some embodiments,

means an aromatic ring wherein V is C.

In some embodiments,

means an aromatic ring wherein V is N, and V is ortho, meta or para relative to Z.
In some embodiments, V is N, and V is ortho relative to Z. In some embodiments, V is N, and V is meta relative to Z. In some embodiments, V is N, and V is para relative to Z.
In some embodiments,

is phenyl.
In some embodiments,

is pyridine.
In some embodiments,

is pyridazine.
In some embodiments,

is pyrimidine.
In some embodiments,

is pyrazine.
In some embodiments,

is selected from those depicted in Tables 1-3, below.

As described generally above, each R is independently hydrogen, halogen, —CN, hydroxyl, $(C_1-C_3)$fluoroalkyl, $(C_1-C_3)$fluoroalkoxy, $(C_3-C_6)$cycloalkyl, —$NO_2$, —$NR_1R_2$, $(C_1-C_4)$alkoxy, phenoxy, —$NR_1$—$SO_2$—$NR_1R_2$, —$NR_1$—$SO_2$—$R_1$, —$NR_1$—C(=O)—$R_1$, —$NR_1$—C(=O)—$NR_1R_2$, —$SO_2$—$NR_1R_2$, —$SO_3H$, —O—$SO_2$—$OR_3$, —O—P(=O)—$(OR_3)(OR_4)$, —O—$CH_2$—$COOR_3$, $(C_1-C_3)$alkyl, said alkyl being optionally mono- or di-substituted by a hydroxyl group or a group of formula (IIa):

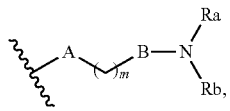

or a group of formula (IIIa):

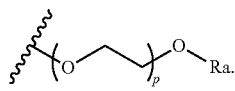

In some embodiments, R is hydrogen. In some embodiments, R is halogen. In some embodiments, R is —CN. In some embodiments, R is hydroxyl. In some embodiments, R is $(C_1-C_3)$fluoroalkyl, said alkyl being optionally mono- or di-substituted by hydroxyl. In some embodiments, R is $(C_1-C_3)$fluoroalkoxy. In some embodiments, R is $(C_3-C_6)$cycloalkyl. In some embodiments, R is —$NO_2$. In some embodiments, R is —$NR_1R_2$. In some embodiments, R is $(C_1-C_4)$alkoxy. In some embodiments, R is phenoxy. In some embodiments, R is —$NR_1$—$SO_2$—$NR_1R_2$. In some embodiments, R is —$NR_1$—$SO_2$—$R_1$. In some embodiments, R is —$NR_1$—C(=O)—$R_1$. In some embodiments, R is —$NR_1$—C(=O)—$NR_1R_2$. In some embodiments, R is —$SO_2$—$NR_1R_2$. In some embodiments, R is —$SO_3H$. In some embodiments, R is —O—$SO_2$—$OR_3$. In some embodiments, R is —O—P(=O)—$(OR_3)(OR_4)$. In some embodiments, R is —O—$CH_2$—$COOR_3$. In some embodiments, R is $(C_1-C_3)$alkyl, said alkyl being optionally mono- or di-substituted by hydroxyl.

In some embodiments, each R is independently halogen, $(C_1-C_3)$fluoroalkyl, $(C_1-C_3)$fluoroalkoxy, —$NR_1R_2$, $(C_1-C_4)$alkoxy, or $(C_1-C_3)$alkyl.

In some embodiments, each R is independently hydrogen, methyl, methoxy, trifluoromethyl, trifluoromethoxy, amino, halogen, or —O—P(=O)—$(OR_3)(OR_4)$. In some embodiments, R is methyl. In some embodiments, R is methoxy. In some embodiments, R is trifluoromethyl. In some embodiments, R is trifluoromethoxy. In some embodiments, R is amino. In some embodiments, R is —O—P(=O)—$(OR_3)(OR_4)$.

In some embodiments, each R is independently methyl, methoxy, trifluoromethyl, halogen, trifluoromethoxy, or amino.

In some embodiments, R is selected from those depicted in Tables 1-3, below.

As described generally above, Q is N or O, provided that R" does not exist when Q is O.

In some embodiments, Q is N. In some embodiments, Q is O, and R" does not exist.

In some embodiments, Q is selected from those depicted in Tables 1-3, below.

As described generally above, each of $R_1$ and $R_2$ is independently hydrogen or $(C_1-C_3)$alkyl.

In some embodiments, $R_1$ is hydrogen. In some embodiments, $R_1$ is $(C_1-C_3)$alkyl. In some embodiments, $R_2$ is hydrogen. In some embodiments, $R_2$ is $(C_1-C_3)$alkyl.

In some embodiments, each of $R_1$ and $R_2$ is independently selected from those depicted in Tables 1-3, below.

As described generally above, each of $R_3$ and $R_4$ is independently hydrogen, $Li^+$, $Na^+$, $K^+$, $N^+(Ra)_4$ or benzyl.

In some embodiments, $R_3$ is hydrogen. In some embodiments, $R_3$ is $Li^+$. In some embodiments, $R_3$ is $Na^+$. In some embodiments, $R_3$ is $K^+$. In some embodiments, $R_3$ is $N^+(Ra)_4$. In some embodiments, $R_3$ is benzyl. In some embodiments, $R_4$ is hydrogen. In some embodiments, $R_4$ is $Li^+$. In some embodiments, $R_4$ is $Na^+$. In some embodiments, $R_4$ is $K^+$. In some embodiments, $R_4$ is $N^+(Ra)_4$. In some embodiments, $R_4$ is benzyl.

In some embodiments, each of $R_3$ and $R_4$ is independently selected from those depicted in Tables 1-3, below.

As described generally above, n is 1, 2 or 3.

In some embodiments, n is 1 or 2. In some embodiments, n is 1. In some embodiments, n is 2. In some embodiments, n is 3.

In some embodiments, n is selected from those depicted in Tables 1-3, below.

As described generally above, n' is 1, 2 or 3.

In some embodiments, n' is 1 or 2. In some embodiments, n' is 1. In some embodiments, n' is 2. In some embodiments, n' is 3.

In some embodiments, n' is selected from those depicted in Tables 1-3, below.

As described generally above, each R' is independently hydrogen, $(C_1-C_3)$alkyl, hydroxyl, halogen, —$NO_2$, —$NR_1R_2$, morpholinyl, morpholino, N-methylpiperazinyl, $(C_1-C_3)$fluoroalkyl, $(C_1-C_4)$alkoxy, —O—P(=O)—$(OR_3)(OR_4)$, —CN, a group of formula (IIa):

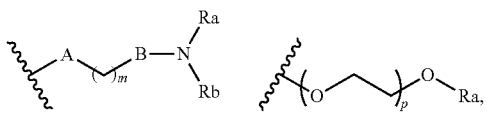

or a group of formula (IIIa):

In some embodiments, R' is hydrogen. In some embodiments, R' is $(C_1-C_3)$alkyl. In some embodiments, R' is Hydroxyl. In some embodiments, R' is halogen. In some embodiments, R' is —$NO_2$. In some embodiments, R' is —$NR_1R_2$. In some embodiments, R' is morpholinyl. In some embodiments, R' is morpholino. In some embodiments, R' is N-methylpiperazinyl. In some embodiments, R' is $(C_1-C_3)$fluoroalkyl. In some embodiments, R' is $(C_1-C_4)$alkoxy. In some embodiments, R' is —O—P(=O)—$(OR_3)(OR_4)$. In some embodiments, R' is —CN.

In some embodiments, R' is a group of formula (IIa):

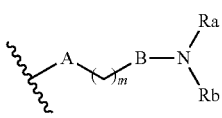

In some embodiments, R' is a group of formula (IIIa):

In some embodiments, R' is amino. In some embodiments, R' is methyl. In some embodiments, R' is a group of formula

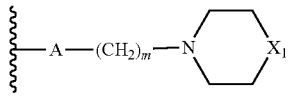

wherein A is O or NH, m is 2 or 3 and $X_1$ is O, $CH_2$ or N—$CH_3$, provided that when R' is such a group, n' is 1 or 2, and when n' is 2, the other R' group is different from said group.

In some embodiments, R' is a group of formula

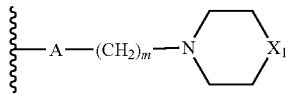

wherein A is O or NH, m is 2 and $X_1$ is O, $CH_2$ or N—$CH_3$, provided that when R' is such a group, n' is 1 or 2, and when n' is 2, the other R' group is different from said group.

In some embodiments, R' is a group of formula

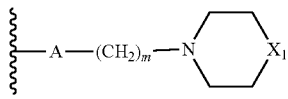

wherein A is O or NH, m is 3 and $X_1$ is O, $CH_2$ or N—$CH_3$, provided that when R' is such a group, n' is 1 or 2, and when n' is 2, the other R' group is different from said group.

In some embodiments, each R' is independently hydrogen, halogen, amino, methyl, —O—P(=O)—(OR$_3$)(OR$_4$), or a group of formula

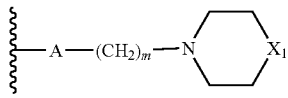

wherein A is O or NH, m is 2 or 3 and $X_1$ is O, $CH_2$ or N—$CH_3$, provided that when R' is such a group, n' is 1 or 2, and when n' is 2, the other R' group is different from said group.

In some embodiments each R' is independently hydrogen, halogen, methyl, or a group of formula

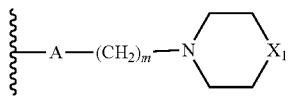

wherein A is O or NH, m is 2 and $X_1$ is O, $CH_2$ or N—$CH_3$, provided that when R' is such a group, n' is 1 or 2, and when n' is 2, the other R' group is different from said group.

In some embodiments, each R' is independently halogen, ($C_1$-$C_3$)alkyl, hydroxyl, —NR$_1$R$_2$, morpholinyl, morpholino, N-methylpiperazinyl, ($C_1$-$C_3$)fluoroalkyl, ($C_1$-$C_4$)alkoxy, or a group of formulas (IIa) or (IIIa) as described herein.

In some embodiments, R' is halogen or methyl.

In some embodiments, each R' is independently selected from those depicted in Tables 1-3, below.

As described generally above, A is a covalent bond, oxygen, or NH.

In some embodiments, A is a covalent bond. In some embodiments, A is oxygen. In some embodiments, A is NH.

In some embodiments, A is selected from those depicted in Tables 1-3, below.

As described generally above, B is a covalent bond or NH.

In some embodiments, B is a covalent bond. In some embodiments, B is NH.

In some embodiments, B is selected from those depicted in Tables 1-3, below.

As described generally above, m is 1, 2, 3, 4 or 5.

In some embodiments, m is 1. In some embodiments, m is 2. In some embodiments, m is 3. In some embodiments, m is 4. In some embodiments, m is 5.

In some embodiments, m is selected from those depicted in Tables 1-3, below.

As described generally above, p is 1, 2 or 3.

In some embodiments, p is 1. In some embodiments, p is 2. In some embodiments, p is 3. In some embodiments, p is 4. In some embodiments, p is 5.

In some embodiments, p is selected from those depicted in Tables 1-3, below.

As described generally above, each of Ra and Rb is independently hydrogen, ($C_1$-$C_5$)alkyl, or ($C_3$-$C_6$)cycloalkyl, or Ra and Rb form together with the nitrogen atom to which they are attached a saturated 5- or 6-membered heterocycle, said heterocycle being optionally substituted by one or more Ra, provided that when R' is a group (IIa) or (IIIa), n' may be 2 or 3 only if other R' groups are different from said group (IIa) or (IIIa).

In some embodiments, Ra is hydrogen. In some embodiments, Ra is ($C_1$-$C_5$)alkyl. In some embodiments, Ra is ($C_3$-$C_6$)cycloalkyl. In some embodiments, Rb is hydrogen. In some embodiments, Rb is ($C_1$-$C_5$)alkyl. In some embodiments, Rb is ($C_3$-$C_6$)cycloalkyl.

In some embodiments, Ra and Rb form together with the nitrogen atom to which they are attached a saturated 5- or 6-membered heterocycle, said heterocycle being optionally substituted by one or more Ra, provided that when R' is a group of formulas (IIa) or (IIIa), n' may be 2 or 3 only if other R' groups are different from said group of formulas (IIa) or (IIIa). In some embodiments, a saturated 5- or 6-membered heterocycle formed by Ra and Rb together with the nitrogen atom to which they are attached, as described above, optionally has an additional heteroatom selected from N, O and S.

In some embodiments, Ra and Rb form together with the nitrogen atom to which they are attached a saturated 5- or 6-membered heterocycle having an additional heteroatom selected from N, O and S, said heterocycle being substituted by one or more Ra, provided that when R' is a group of formulas (IIa) or (IIIa), n' may be 2 or 3 only if other R' groups are different from said group of formulas (IIa) or (IIIa).

In some embodiments, Ra and Rb form together with the nitrogen atom to which they are attached a saturated 5-membered heterocycle, provided that when R' is a group of formulas (IIa) or (IIIa), n' may be 2 or 3 only if other R' groups are different from said group of formulas (IIa) or (IIIa).

In some embodiments, Ra and Rb form together with the nitrogen atom to which they are attached a saturated 6-membered heterocycle, provided that when R' is a group of formulas (IIa) or (IIIa), n' may be 2 or 3 only if other R' groups are different from said group of formulas (IIa) or (IIIa).

In some embodiments, Ra and Rb form together with the nitrogen atom to which they are attached a saturated 5- or 6-membered heterocycle optionally having an additional heteroatom selected from N, O and S, said heterocycle being optionally substituted by one or more Ra, provided that when R' is a group (IIa) or (IIIa), n' may be 2 only if the other R' group is different from said group (IIa) or (IIIa).

In some embodiments, each of Ra and Rb is independently selected from those depicted in Tables 1-3, below.

As described generally above, R" is hydrogen, $(C_1-C_4)$ alkyl, or a group of formula (IIa) as defined above.

In some embodiments, R" is hydrogen or $(C_1-C_4)$alkyl. In some embodiments, R" is hydrogen. In some embodiments, R" is $(C_1-C_4)$alkyl. In some embodiments, R" is a group of formula (IIa) as described herein.

In some embodiments, R" is a group of formula

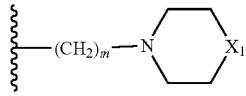

wherein m is 2 or 3, and $X_1$ is O, $CH_2$, or N—$CH_3$.

In some embodiments, n is 1; n' is 1 or 2; R" is H; R is selected from methyl, methoxy, trifluoromethyl, halogen, trifluoromethoxy, and amino; and each R' is independently halogen, methyl, or a group

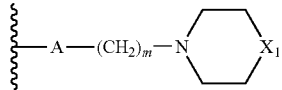

wherein A is O or NH, m is 2 or 3 and $X_1$ is O, $CH_2$ or N—$CH_3$, provided that when n' is 2, the other R' group is different from said group.

In some embodiments, n is 1; n' is 1; R" is H; R is selected from methyl, methoxy, trifluoromethyl, halogen, and trifluoromethoxy; and R' is halogen or methyl.

In some embodiments, the present invention provides a method for treating an inflammatory disease, disorder or condition comprising administering to a patient in need thereof a compound of formula (Ia):

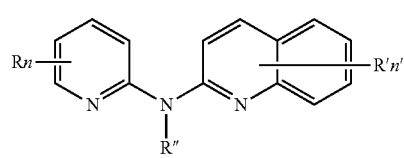

(Ia)

or a pharmaceutically acceptable salt thereof, wherein each of variables R, R', R", n, and n' is independently as defined above and described in embodiments In some embodiments, the present invention provides a method for treating an inflammatory disease, disorder or condition comprising administering to a patient in need thereof a compound of formula (Ib):

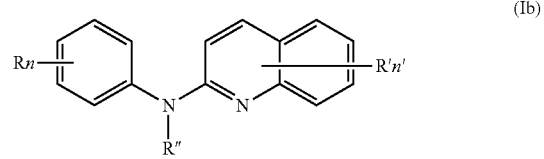

(Ib)

or a pharmaceutically acceptable salt thereof, wherein each of variables R, R', R", n, and n' is independently as defined above and described in embodiments herein, both singly and in combination.

In some embodiments, the present invention provides the compound for use as defined above, wherein the compound is of formula (Ib):

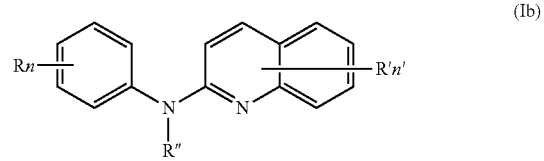

(Ib)

or anyone of its metabolites or a pharmaceutically acceptable salt thereof, wherein R, R' and R" are as defined above.

In some embodiments, the present invention provides a method for treating an inflammatory disease, disorder or condition comprising administering to a patient in need thereof a compound of formula (Ic):

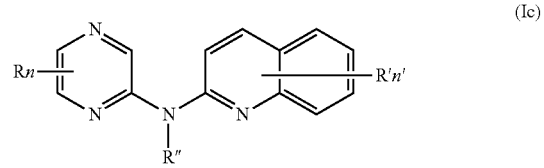

(Ic)

or a pharmaceutically acceptable salt thereof, wherein each of variables R, R', R", n, and n' is independently as defined above and described in embodiments herein, both singly and in combination.

In some embodiments, the present invention provides a method for treating an inflammatory disease, disorder or condition comprising administering to a patient in need thereof a compound of formula (Id):

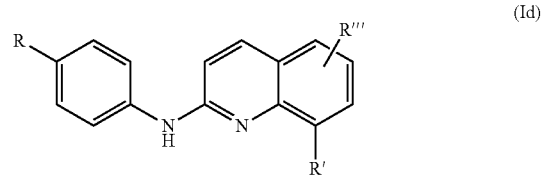

(Id)

or a pharmaceutically acceptable salt thereof, wherein each of R and R' is independently as defined above and described in embodiments herein, both singly and in combination, and R''' is hydrogen or a group

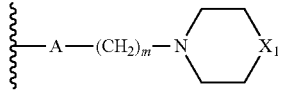

wherein A is O or NH, m is 2 or 3, and $X_1$ is O, $CH_2$ or N—$CH_3$.

In some embodiments, the present invention provides a method for treating an inflammatory disease, disorder or condition comprising administering to a patient in need thereof a compound of formula (Id), or a pharmaceutically acceptable salt thereof, wherein R is methyl, methoxy, trifluoromethyl, halogen, trifluoromethoxy, or amino; R' is halogen or methyl, and R''' is hydrogen or a group

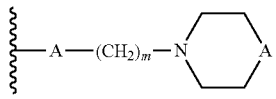

wherein A is O or NH, m is 2 or 3, and X, is O, $CH_2$ or N—$CH_3$.

In some embodiments, R''' is a group

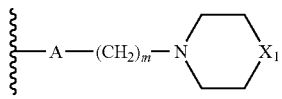

wherein A is O or NH, m is 2 or 3, and $X_1$ is O, $CH_2$ or N—$CH_3$. In some embodiments, R''' is a group

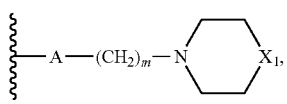

wherein A is O, m is 2 or 3, and $X_1$ is O, $CH_2$ or N—$CH_3$. In some embodiments, R''' is a group

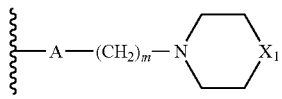

wherein A is NH, m is 2 or 3, and $X_1$ is O, $CH_2$ or N—$CH_3$. In some embodiments, the present invention provides a method for treating an inflammatory disease, disorder or condition comprising administering to a patient in need thereof a compound of formula (Ib'):

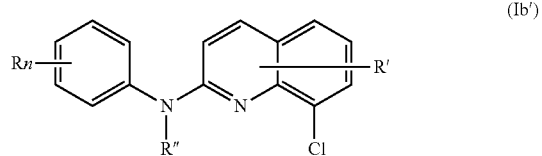

(Ib')

or a pharmaceutically acceptable salt thereof, wherein each of variables R, R', R'', and n is independently as defined above and described in embodiments herein, both singly and in combination. In some embodiments, the present invention provides a method for treating an inflammatory disease, disorder or condition comprising administering to a patient in need thereof a compound of formula (Ib), or a pharmaceutically acceptable salt thereof, wherein: each R is independently halogen, ($C_1$-$C_3$)fluoroalkyl, ($C_1$-$C_3$)fluoroalkoxy, —$NR_1R_2$, ($C_1$-$C_4$)alkoxy, or ($C_1$-$C_3$)alkyl, said alkyl being optionally mono- or di-substituted by a hydroxyl group; n is 1 or 2; n' is 1 or 2;
each of $R_1$ and $R_2$ is independently hydrogen or ($C_1$-$C_3$) alkyl;
each of R' is independently halogen, ($C_1$-$C_3$)alkyl, hydroxyl, —$NR_1R_2$, morpholinyl, morpholino, N-methylpiperazinyl, ($C_1$-$C_3$)fluoroalkyl, ($C_1$-$C_4$)alkoxy, or a group of formulas (IIa) or (IIIa) as described herein;
A is a covalent bond, oxygen, or NH; B is a covalent bond or NH;
m is 1, 2, 3, 4 or 5;
p is 1, 2 or 3;
each of Ra and Rb is independently hydrogen, ($C_1$-$C_5$)alkyl, or ($C_3$-$C_6$)cycloalkyl, or Ra and Rb form together with the nitrogen atom to which they are attached a saturated 5- or 6-membered heterocycle optionally having an additional heteroatom selected from N, O and S, said heterocycle being optionally substituted by one or more Ra, provided that when R' is a group (IIa) or (IIIa), n' may be 2 only if the other R' group is different from said group (IIa) or (IIIa); and R'' is hydrogen or ($C_1$-$C_4$)alkyl.

In some embodiments, the present invention provides a method for treating an inflammatory disease, disorder or condition comprising administering to a patient in need thereof a compound of formula (Ib), or a pharmaceutically acceptable salt thereof, wherein each R' is independently hydrogen, halogen, ($C_1$-$C_3$)alkyl, or a ($C_1$-$C_4$)alkoxy group, said alkyl being optionally mono- or di-substituted by a hydroxyl group; R'' is hydrogen or ($C_1$-$C_4$)alkyl; n is 1 or 2; n' is 1 or 2; when n is 1, R is ($C_1$-$C_3$) fluoroalkoxy, $NR_1R_2$, or phenoxy, wherein each of $R_1$ and $R_2$ is independently ($C_1$-$C_3$)alkyl; and when n is 2, one of the two R groups is ($C_1$-$C_3$) fluoroalkoxy and the other R group is ($C_1$-$C_3$)alkyl.

In some embodiments, the present invention provides a method for treating an inflammatory disease, disorder or condition comprising administering to a patient in need thereof a compound of formula (Ib), or a pharmaceutically acceptable salt thereof, wherein each R is independently ($C_1$-$C_3$)fluoroalkoxy; each R' is independently hydrogen, halogen, ($C_1$-$C_3$)alkyl, or ($C_1$-$C_4$)alkoxy; R'' is hydrogen or ($C_1$-$C_4$)alkyl; n is 1; and n' is 1 or 2.

In some embodiments, the present invention provides a method for treating an inflammatory disease, disorder or condition comprising administering to a patient in need thereof a compound of formula (Ib'), or a pharmaceutically acceptable salt thereof, wherein each R is independently hydrogen, halogen, ($C_1$-$C_3$)alkyl, —$NR_1R_2$, ($C_1$-$C_3$)fluoroalkoxy, —$NO_2$, phenoxy, or ($C_1$-$C_4$)alkoxy, said alkyl being optionally mono- or di-substituted by a hydroxyl group; each of $R_1$ and $R_2$ is independently hydrogen or $(C_1-C_3)$ alkyl; R' is hydrogen, halogen, $(C_1-C_3)$alkyl, or $(C_1-C_4)$ alkoxy, with the proviso that R' is different from a methyl group at position 4 of the quinoline group; R" is hydrogen or $(C_1-C_4)$alkyl; n is 1, 2, or 3; and n' is 1 or 2.

In some embodiment, the present invention provides the compound for use as defined above, wherein the compound is of formula (Ib'):

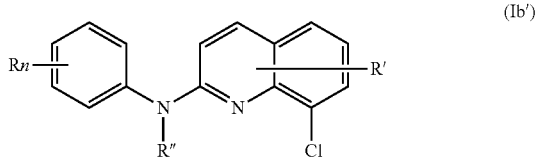

(Ib')

or anyone of its metabolites or a pharmaceutically acceptable salt thereof, wherein R, R' and R" are as defined above.

In some embodiments, the present invention provides the compound of formula (Ib') or anyone of its metabolites or a pharmaceutically acceptable salt thereof for use as defined above, wherein:
R independently represent a halogen atom or a group chosen among a $(C_1-C_3)$fluoroalkoxy group, a —$NR_1R_2$ group, a $(C_1-C_4)$alkoxy group, a —O—P(=O)(OR_3)(OR_4) group, a $(C_1-C_3)$alkyl group, a $NO_2$ group, a -A-$(CH_2)_m$—B— NRaRb group (formula IIa) and a —(O—$CH_2$—$CH_2)_p$— O—Ra group (formula IIIa),
n is 1 or 2,
R' represents a hydrogen atom, a halogen atom or a group chosen among a —$NR_1R_2$ group, a —O—P(=O)(OR_3) (OR_4) group, a —NH—$SO_2$—N(CH_3)_2 group, and a -A- $(CH_2)_m$—B—NRaRb group (IIa),
R" is a hydrogen atom, a $(C_1-C_4)$alkyl group or a -A-$(CH_2)_m$ —B—NRaRb group (formula IIa),
$R_1$ and $R_2$ are independently a hydrogen atom or a $(C_1-C_3)$ alkyl group,
$R_3$ and $R_4$ are independently hydrogen, $Li^+$, $Na^+$, $K^+$, $N^+(Ra)_4$ or benzyl,
A is a covalent bond, an oxygen atom or NH,
B is a covalent bond,
m is 2, 3 or 4,
p is 1, 2 or 3,
Ra and Rb independently represent a hydrogen atom or a $(C_1-C_5)$alkyl group, Ra and Rb can further form together with the nitrogen atom to which they are attached a saturated 5- or 6-membered heterocycle optionally containing a further heteroatom chosen among N, O and S, said heterocycle being optionally substituted by one or more Ra.

According to an even more particular embodiment, the invention provides the compound of formula (Ib') or anyone of its metabolites or a pharmaceutically acceptable salt thereof for use as defined above, wherein: R independently represent F, Cl, —$NH_2$, —$N(CH_3)_2$, —$OCH_3$, —O—$(CH_2)_3$ —$CH_3$, —$OCF_3$, —$CH_3$, —O—$(CH_2)_2$—OH, —O— $(CH_2)_2$ —O—$(CH_2)_2$—$OCH_3$, a —$NO_2$ group, a —O—P (=O)(OH)(OH) group,
a —O—$(CH_2)_2$-morpholino group or a —O—$(CH_2)_2$-piperidino group,
n is 1 or 2,
R' represents a hydrogen atom, Cl, —$CH_2$—$CH_2$—$CH_3$, a —O—$(CH_2)_2$-morpholino group, a —O—$(CH_2)_2$-piperidino group, a —O—$(CH_2)_3$-piperidino group, a —N—$(CH_2)_3$-morpholino group, a —NH— $SO_2$—$N(CH_3)_2$ group, $NH_2$, or a —O—P(=O)(OH)(OH) group, and
R" is a hydrogen atom, —$CH_3$, a —$(CH_2)_3$-piperidino group, a —$(CH_2)_2$-morpholino group,
a —$(CH_2)_4$-morpholino group or a —$(CH_2)_2$-pyrrolidino group.

In an embodiment, the present invention provides the compound of formula (Ib') or anyone of its metabolites or a pharmaceutically acceptable salt thereof for use as defined above, wherein said compound is chosen among: compounds 96, 98, 108, 109, 111, 115, 122, 125, 128, 129, 130, 132, 133, 135, 138 to 141, 143, and 145 to 164 as listed herein after.

In some embodiments, the present invention provides a method for treating an inflammatory disease, disorder or condition comprising administering to a patient in need thereof a compound of formula:

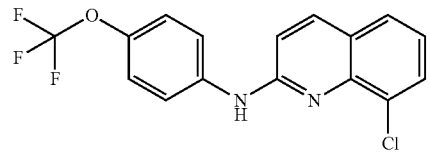 [SMILES: FC(F)(F)Oc1ccc(Nc2ccc3cccc(Cl)c3n2)cc1]

("ABX464"), or a pharmaceutically acceptable salt thereof.

In some embodiments, the present invention provides the compound of formula (Ib') or anyone of its metabolites or a pharmaceutically acceptable salt thereof for use as defined above, wherein said compound is 8-Chloro-N-(4-(trifluoromethoxy)phenyl)quinolin-2-amine.

In some embodiments, the compound ABX464, or a pharmaceutically acceptable salt thereof, is under an amorphous form. In some embodiments, the compound ABX464, or a pharmaceutically acceptable salt thereof, is under a crystallized form. In some embodiments, a crystallized form of the compound ABX464, or a pharmaceutically acceptable salt thereof, has a melting point at 120.5° C. (±2° C.).

In some embodiments, a crystallized form of the compound ABX464, or a pharmaceutically acceptable salt thereof, shows peaks in an x-ray powder diffractogram (XRPD) at angles 7.3, 14.6, 18.4, and 24.9. In some embodiments, a crystallized form of the compound ABX464, or a pharmaceutically acceptable salt thereof, shows one or more XRPD peaks at angles selected from 18.0, 24.2, 28.3, and 29.5. In some embodiments, a crystallized form of the compound ABX464, or a pharmaceutically acceptable salt thereof, shows one or more XRPD peaks at angles selected from 18.6, 22.3, 23.0, and 23.5.

According to a particular embodiment, the crystalline polymorphic form of 8-Chloro-N-(4-(trifluoromethoxy)phenyl)quinolin-2-amine is characterized by the following main peaks expressed as degree 2-Theta angles by a XRPD analysis: 7.3, 14.6, 23.5, and 28.4 (each time ±0.2) and may further show the following additional peaks expressed as degree 2-Theta angles: 12.1, 17.3, 18.4, 23.0; 24.2, 24.9, 27.4 and 29.1 (each time+0.2) and even optionally further the following additional peaks expressed as degree 2-Theta angles: 13.7, 16.3, 16.9, 18.1, 22.4, and 29.6 (each time ±0.2).

In some embodiments, the present invention provides a method for treating an inflammatory disease, disorder or condition comprising administering to a patient in need thereof a compound selected from Table 1:

TABLE 1
(compounds of formula Ia as defined above)
1 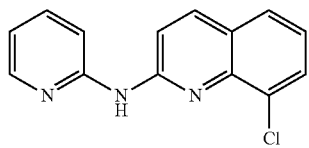 [SMILES: Clc1cccc2ccc(Nc3ccccn3)nc12]
2 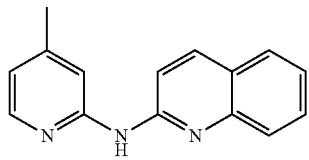 [SMILES: Cc1ccnc(Nc2ccc3ccccc3n2)c1]
3 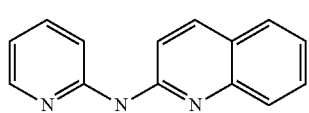
4 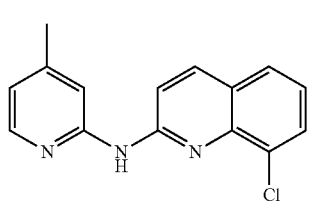 [SMILES: Cc1ccnc(Nc2ccc3cccc(Cl)c3n2)c1]
5 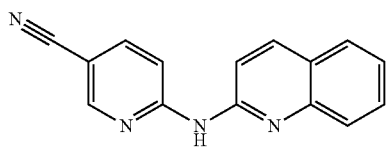 [SMILES: N#Cc1ccc(Nc2ccc3ccccc3n2)nc1]
6 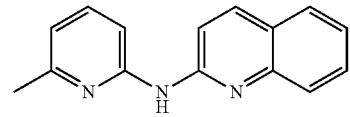 [SMILES: Cc1cccc(Nc2ccc3ccccc3n2)n1]
7 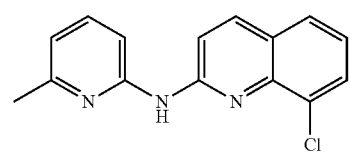 [SMILES: Cc1cccc(Nc2ccc3cccc(Cl)c3n2)n1]
8 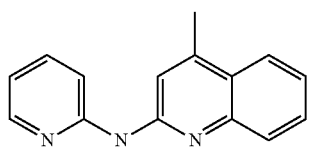
9 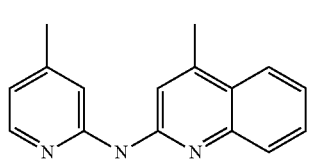
10 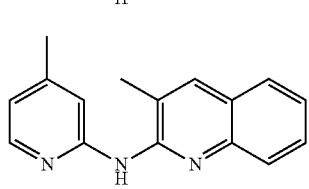
TABLE 1-continued
(compounds of formula Ia as defined above)
11 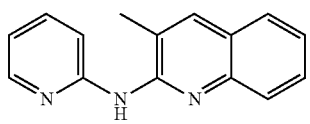 [SMILES: Cc1cc2ccccc2nc1Nc1ccccn1]
12 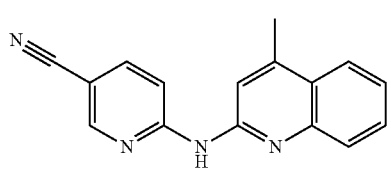 [SMILES: Cc1cc(Nc2ccc(C#N)cn2)nc2ccccc12]
13 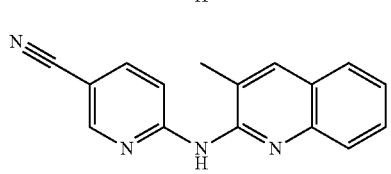
14 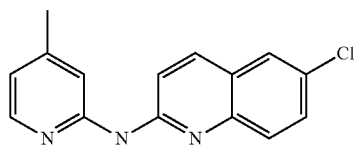
15 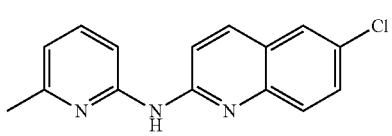 [SMILES: Cc1cccc(Nc2ccc3cc(Cl)ccc3n2)n1]
16 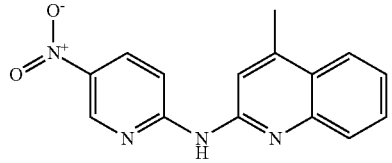 [SMILES: Cc1cc(Nc2ccc([N+](=O)[O-])cn2)nc2ccccc12]
17 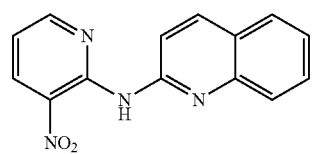 [SMILES: O=[N+]([O-])c1cccnc1Nc1ccc2ccccc2n1]
18 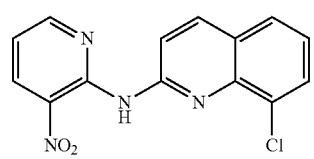 [SMILES: O=[N+]([O-])c1cccnc1Nc1ccc2cccc(Cl)c2n1]
19 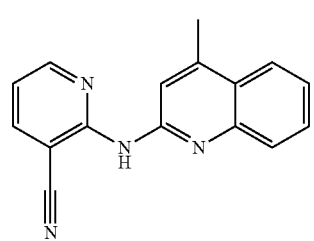 [SMILES: Cc1cc(Nc2ncccc2C#N)nc2ccccc12]

TABLE 1-continued (compounds of formula Ia as defined above)

| # | Structure |
|---|---|
| 20 | 3-methylpyridin-2-yl-NH-quinolin-2-yl |
| 21 | 5-methylpyridin-2-yl-NH-quinolin-2-yl |
| 22 | 4-cyanopyridin-2-yl-NH-quinolin-2-yl |
| 23 | 5-trifluoromethylpyridin-2-yl-NH-quinolin-2-yl |
| 24 | 3-methylpyridin-2-yl-NH-(8-chloroquinolin-2-yl) |
| 25 | 5-methylpyridin-2-yl-NH-(8-chloroquinolin-2-yl) |
| 26 | 5-trifluoromethylpyridin-2-yl-NH-(8-chloroquinolin-2-yl) |
| 27 | 3-methoxypyridin-2-yl-NH-quinolin-2-yl |
| 28 | 5-nitropyridin-2-yl-NH-quinolin-2-yl |
| 29 | 5-cyanopyridin-2-yl-NH-(8-chloroquinolin-2-yl) |
| 30 | 5-fluoropyridin-2-yl-NH-quinolin-2-yl |
| 31 | 6-trifluoromethylpyridin-2-yl-NH-quinolin-2-yl |
| 32 | 5-fluoropyridin-2-yl-NH-(8-chloroquinolin-2-yl) |
| 33 | 6-methylpyridin-2-yl-NH-(4-methylquinolin-2-yl) |
| 34 | 6-methylpyridin-2-yl-NH-(3-methylquinolin-2-yl) |
| 35 | 5-cyanopyridinium-2-yl-NH-quinolin-2-yl chloride |
| 36 | 4-methylpyridinium-2-yl-NH-(8-chloroquinolin-2-yl) chloride |
| 37 | 4-ethylpyridin-2-yl-NH-(8-chloroquinolin-2-yl) |

TABLE 1-continued
(compounds of formula Ia as defined above)
38 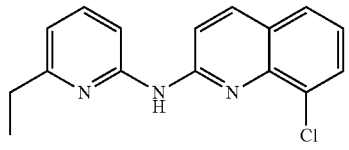 [SMILES: CCc1cccc(Nc2ccc3cccc(Cl)c3n2)n1]
39 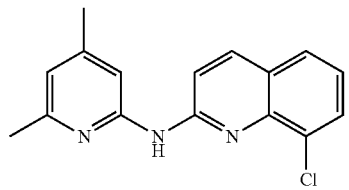 [SMILES: Cc1cc(C)nc(Nc2ccc3cccc(Cl)c3n2)c1]
40 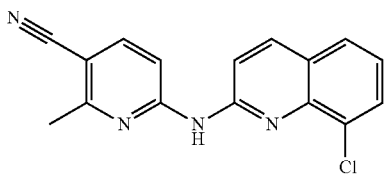 [SMILES: Cc1nc(Nc2ccc3cccc(Cl)c3n2)ccc1C#N]
41 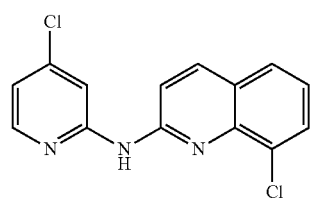 [SMILES: Clc1ccnc(Nc2ccc3cccc(Cl)c3n2)c1]
42 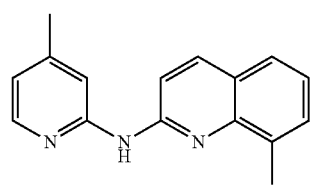 [SMILES: Cc1ccnc(Nc2ccc3cccc(C)c3n2)c1]
43 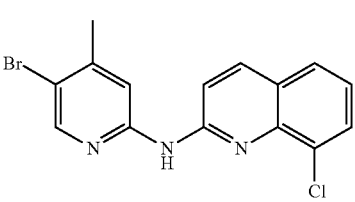 [SMILES: Cc1cc(Nc2ccc3cccc(Cl)c3n2)ncc1Br]
44 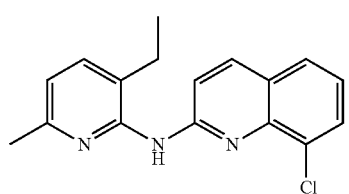 [SMILES: CCc1ccc(C)nc1Nc1ccc2cccc(Cl)c2n1]
45 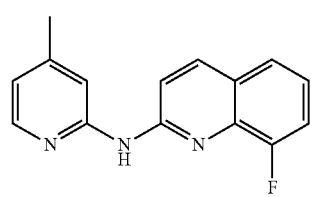 [SMILES: Cc1ccnc(Nc2ccc3cccc(F)c3n2)c1]
TABLE 1-continued
(compounds of formula Ia as defined above)
46 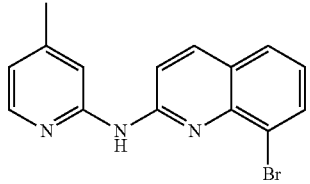 [SMILES: Cc1ccnc(Nc2ccc3cccc(Br)c3n2)c1]
47 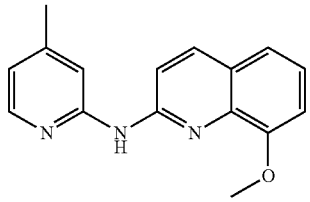 [SMILES: COc1cccc2ccc(Nc3cc(C)ccn3)nc12]
48 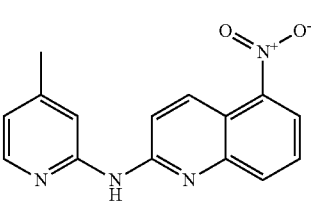 [SMILES: Cc1ccnc(Nc2ccc3c([N+](=O)[O-])cccc3n2)c1]
49 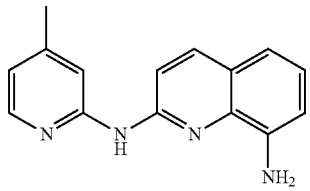 [SMILES: Cc1ccnc(Nc2ccc3cccc(N)c3n2)c1]
50 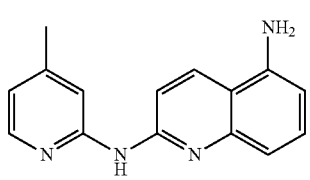 [SMILES: Cc1ccnc(Nc2ccc3c(N)cccc3n2)c1]
51 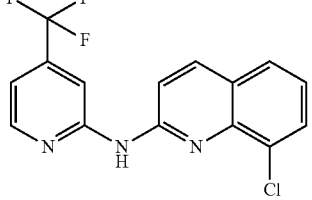
52 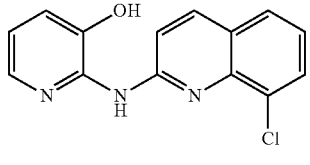 [SMILES: Oc1cccnc1Nc1ccc2cccc(Cl)c2n1]
53 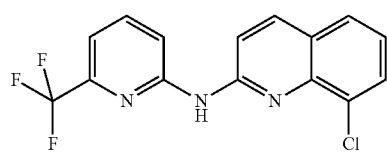 [SMILES: FC(F)(F)c1cccc(Nc2ccc3cccc(Cl)c3n2)n1]

TABLE 1-continued
(compounds of formula Ia as defined above)
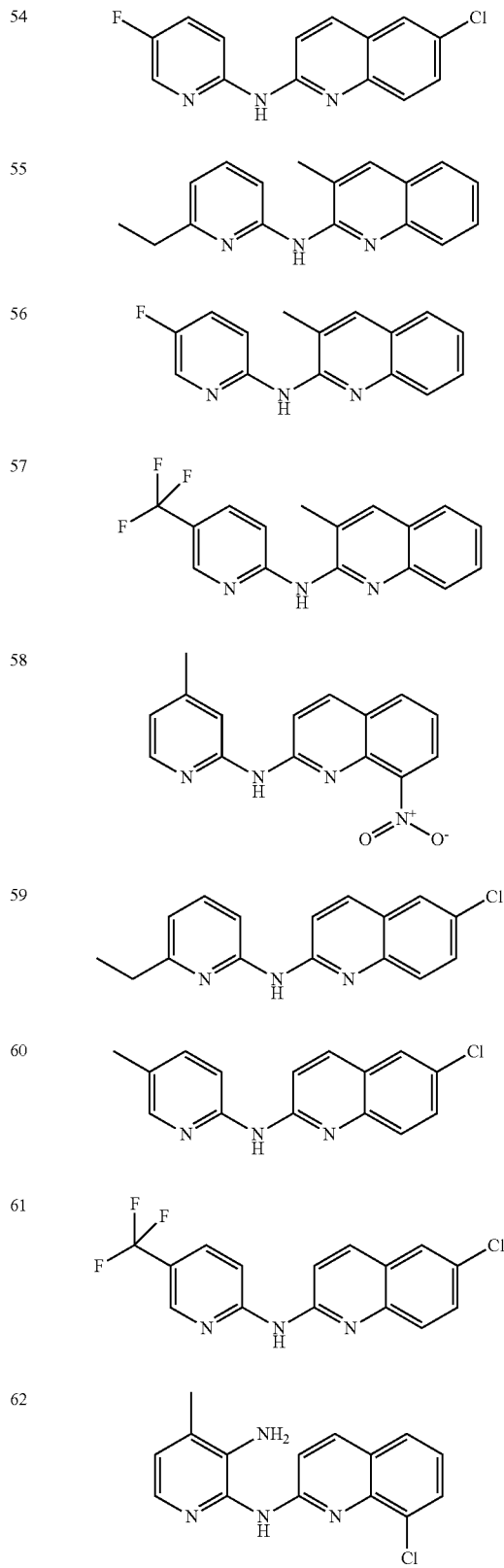
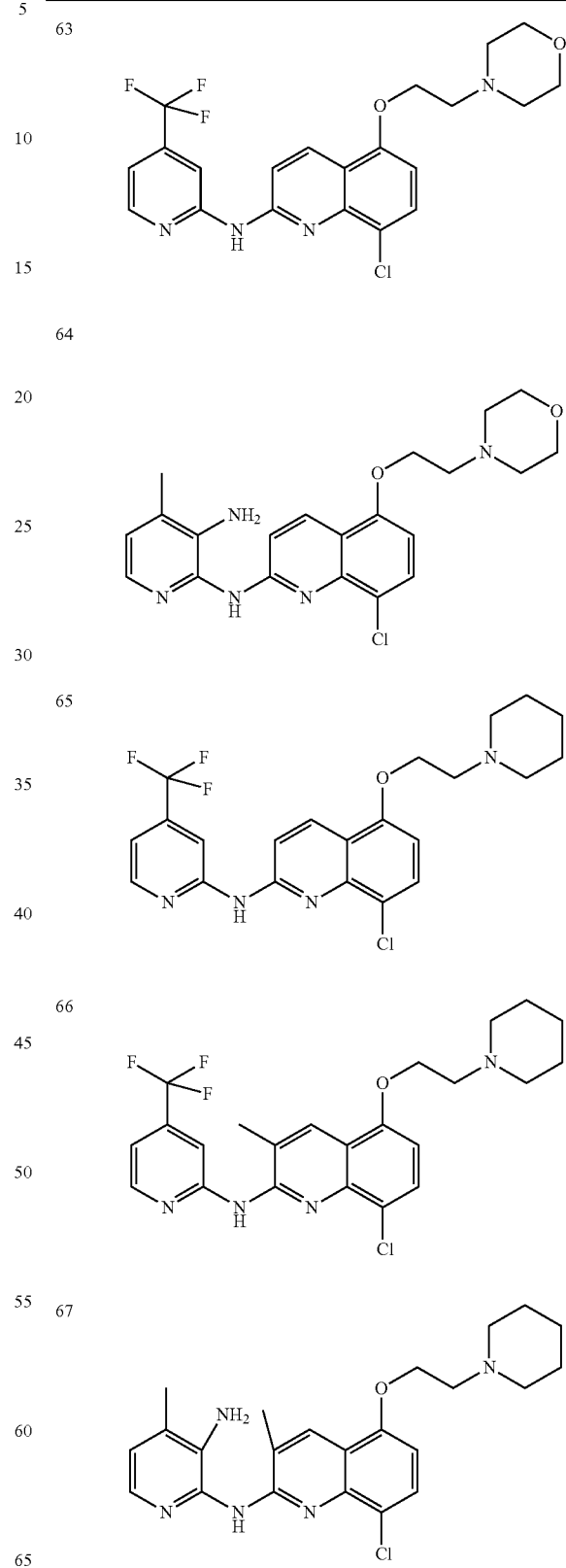

TABLE 1-continued
(compounds of formula Ia as defined above)
68 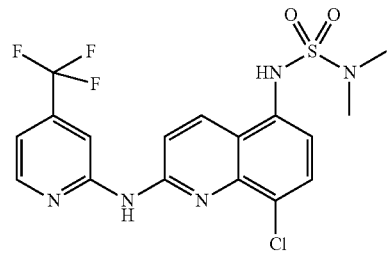 [SMILES: CN(C)S(=O)(=O)Nc1ccc(Cl)c2nc(Nc3cc(C(F)(F)F)ccn3)ccc12]
69 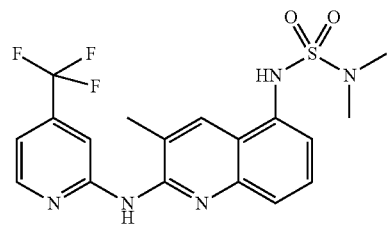 [SMILES: Cc1cc2c(NS(=O)(=O)N(C)C)cccc2nc1Nc1cc(C(F)(F)F)ccn1]
70 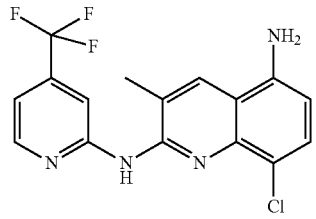
71 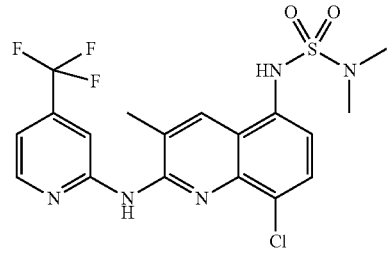 [SMILES: Cc1cc2c(NS(=O)(=O)N(C)C)ccc(Cl)c2nc1Nc1cc(C(F)(F)F)ccn1]
72 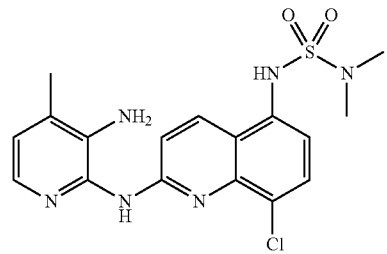 [SMILES: Cc1ccnc(Nc2ccc3c(NS(=O)(=O)N(C)C)ccc(Cl)c3n2)c1N]
73 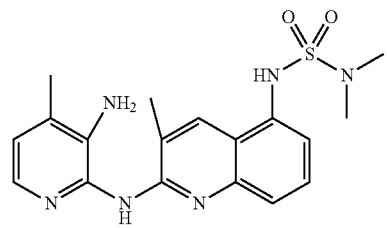 [SMILES: Cc1cc2c(NS(=O)(=O)N(C)C)cccc2nc1Nc1nccc(C)c1N]
TABLE 1-continued
(compounds of formula Ia as defined above)
74 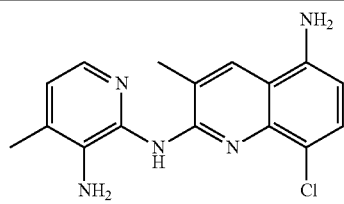
75 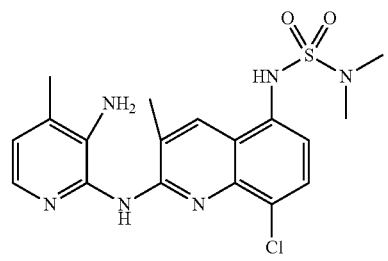 [SMILES: Cc1cc2c(NS(=O)(=O)N(C)C)ccc(Cl)c2nc1Nc1nccc(C)c1N]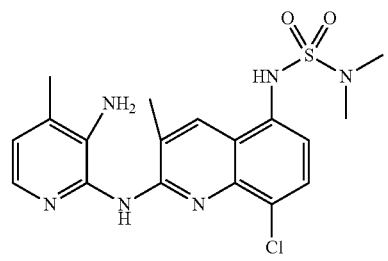 [SMILES: Cc1cc2c(NS(=O)(=O)N(C)C)ccc(Cl)c2nc1Nc1nccc(C)c1N]
76 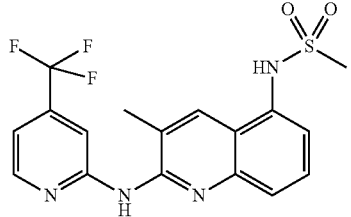 [SMILES: Cc1cc2c(NS(C)(=O)=O)cccc2nc1Nc1cc(C(F)(F)F)ccn1]
77 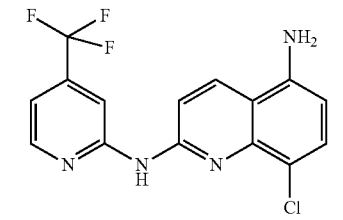 [SMILES: Nc1ccc(Cl)c2nc(Nc3cc(C(F)(F)F)ccn3)ccc12]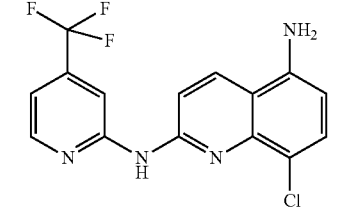
78 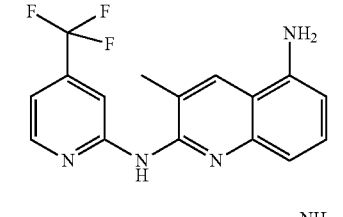
79 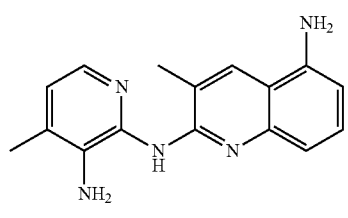 [SMILES: Cc1cc2c(N)cccc2nc1Nc1nccc(C)c1N]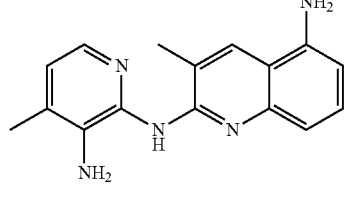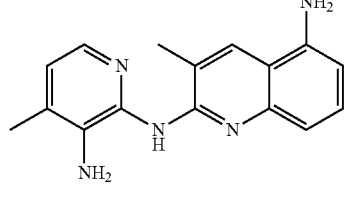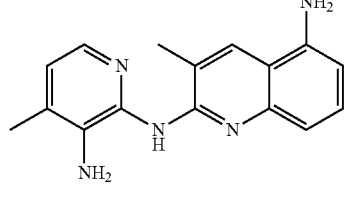
80 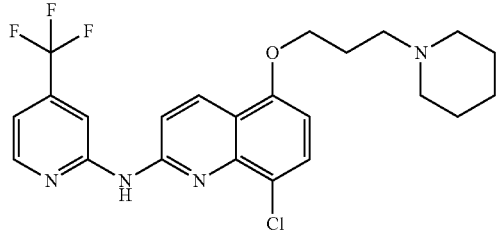 [SMILES: FC(F)(F)c1ccnc(Nc2ccc3c(OCCCN4CCCCC4)ccc(Cl)c3n2)c1]

TABLE 1-continued
(compounds of formula Ia as defined above)
81 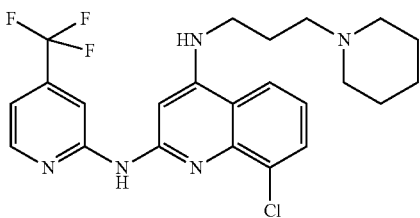 [SMILES: FC(F)(F)c1ccnc(Nc2cc(NCCCN3CCCCC3)c3cccc(Cl)c3n2)c1]
82 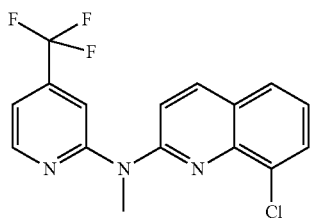 [SMILES: CN(c1cc(C(F)(F)F)ccn1)c1ccc2cccc(Cl)c2n1]
83 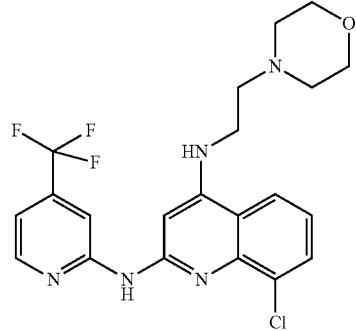 [SMILES: FC(F)(F)c1ccnc(Nc2cc(NCCN3CCOCC3)c3cccc(Cl)c3n2)c1]
84 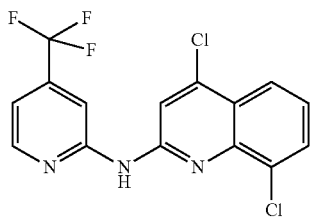 [SMILES: FC(F)(F)c1ccnc(Nc2cc(Cl)c3cccc(Cl)c3n2)c1]
85 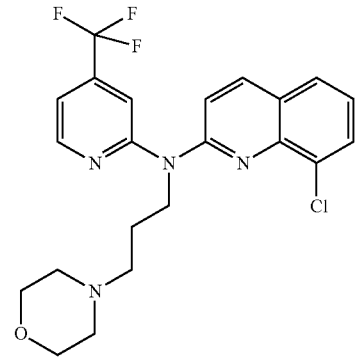 [SMILES: FC(F)(F)c1ccnc(N(CCCN2CCOCC2)c2ccc3cccc(Cl)c3n2)c1]
TABLE 1-continued
(compounds of formula Ia as defined above)
86 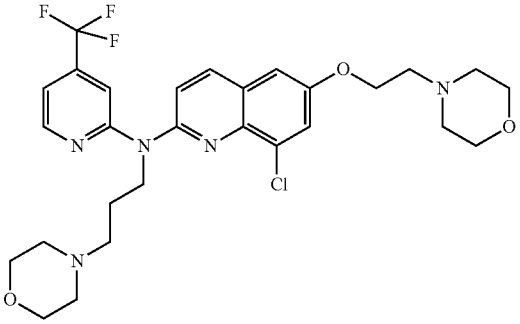 [SMILES: FC(F)(F)c1ccnc(N(CCCN2CCOCC2)c2ccc3cc(OCCN4CCOCC4)cc(Cl)c3n2)c1]
87 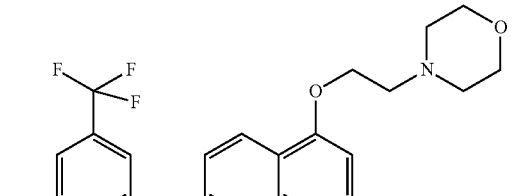
88 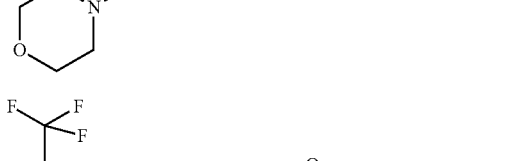
89 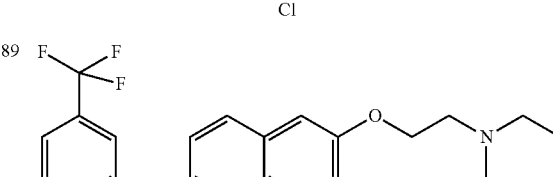
90 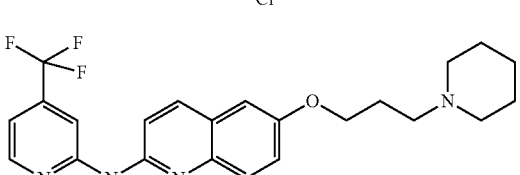
91 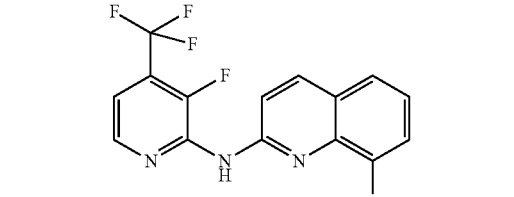

TABLE 1-continued (compounds of formula Ia as defined above)

92 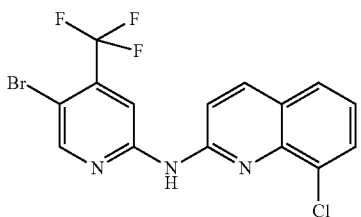 [SMILES: FC(F)(F)c1cc(Nc2ccc3cccc(Cl)c3n2)ncc1Br]

93 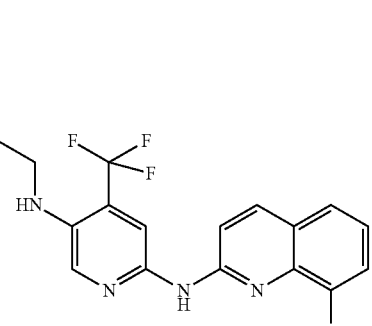

94 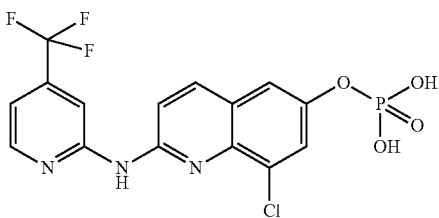 [SMILES: O=P(O)(O)Oc1cc(Cl)c2nc(Nc3cc(C(F)(F)F)ccn3)ccc2c1]

or a pharmaceutically acceptable salt thereof.

In some embodiments, the present invention provides a method for treating an inflammatory disease, disorder or condition comprising administering to a patient in need thereof a compound selected from Table 2:

TABLE 2

(compounds of formula (Ib) as defined above)

95 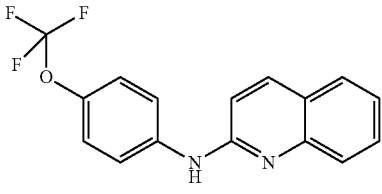 [SMILES: FC(F)(F)Oc1ccc(Nc2ccc3ccccc3n2)cc1]

96 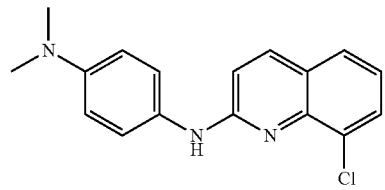 [SMILES: CN(C)c1ccc(Nc2ccc3cccc(Cl)c3n2)cc1]

97 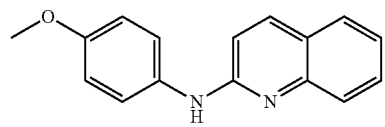 [SMILES: COc1ccc(Nc2ccc3ccccc3n2)cc1]

TABLE 2-continued (compounds of formula (Ib) as defined above)

98 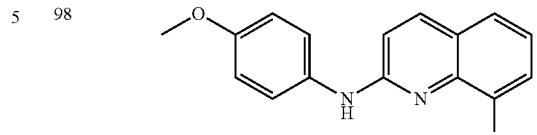

99 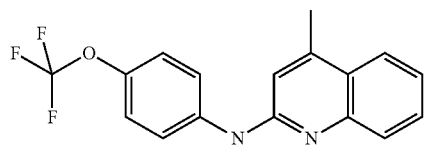

100 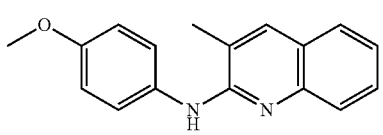 [SMILES: COc1ccc(Nc2nc3ccccc3cc2C)cc1]

101 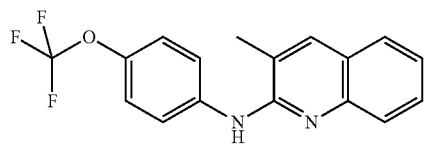 [SMILES: Cc1cc2ccccc2nc1Nc1ccc(OC(F)(F)F)cc1]

102 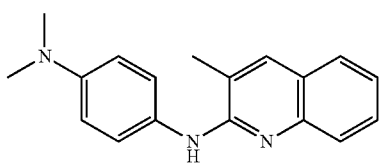 [SMILES: Cc1cc2ccccc2nc1Nc1ccc(N(C)C)cc1]

103 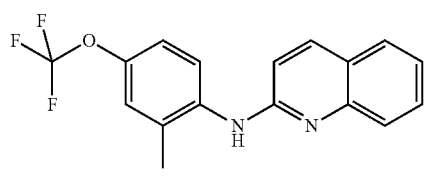 [SMILES: Cc1cc(OC(F)(F)F)ccc1Nc1ccc2ccccc2n1]

104 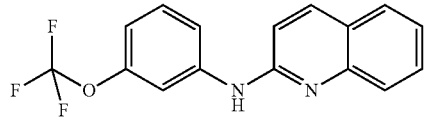 [SMILES: FC(F)(F)Oc1cccc(Nc2ccc3ccccc3n2)c1]

105 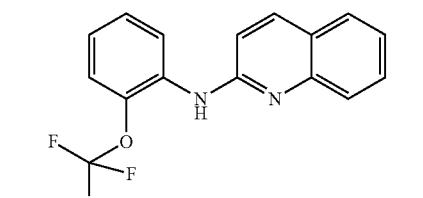

106 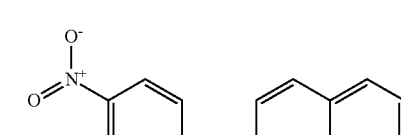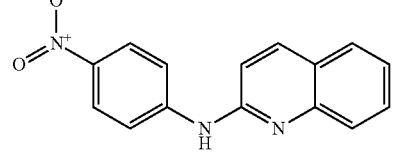

TABLE 2-continued
(compounds of formula (Ib) as defined above)
107 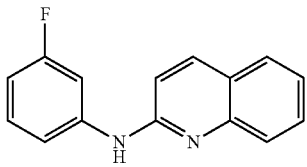 [SMILES: Fc1cccc(Nc2ccc3ccccc3n2)c1]
108 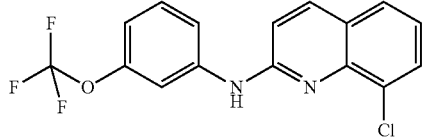 [SMILES: FC(F)(F)Oc1cccc(Nc2ccc3cccc(Cl)c3n2)c1]
109 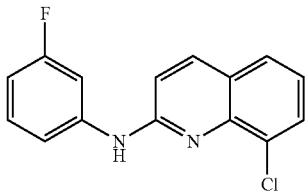 [SMILES: Fc1cccc(Nc2ccc3cccc(Cl)c3n2)c1]
110 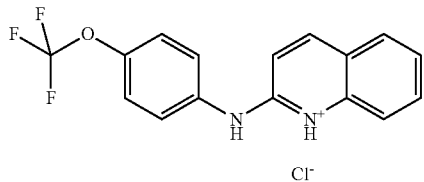
111 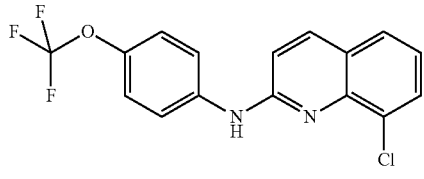 [SMILES: FC(F)(F)Oc1ccc(Nc2ccc3cccc(Cl)c3n2)cc1]
112 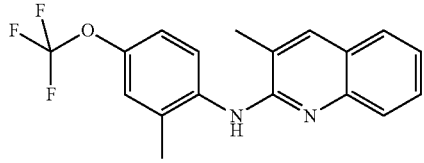 [SMILES: Cc1cc(OC(F)(F)F)ccc1Nc1nc2ccccc2cc1C]
113 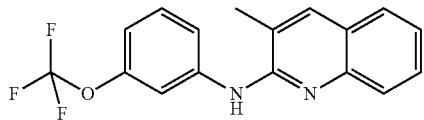 [SMILES: Cc1cc2ccccc2nc1Nc1cccc(OC(F)(F)F)c1]
114 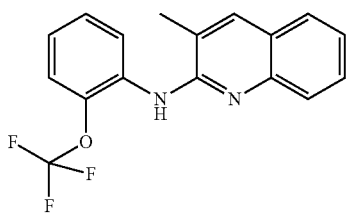 [SMILES: Cc1cc2ccccc2nc1Nc1ccccc1OC(F)(F)F]
TABLE 2-continued
(compounds of formula (Ib) as defined above)
115 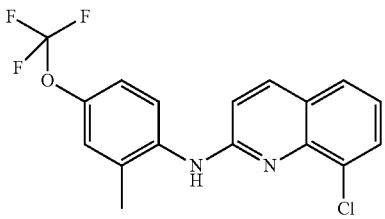 [SMILES: Cc1cc(OC(F)(F)F)ccc1Nc1ccc2cccc(Cl)c2n1]
116 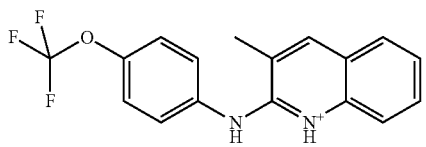
117 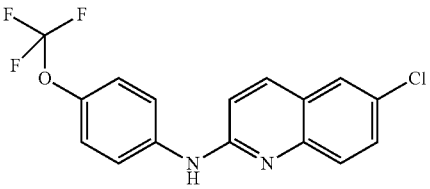 [SMILES: FC(F)(F)Oc1ccc(Nc2ccc3cc(Cl)ccc3n2)cc1]
118 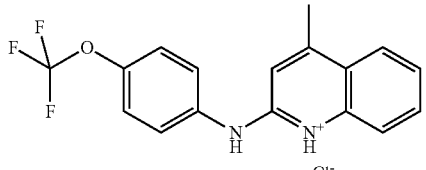
119 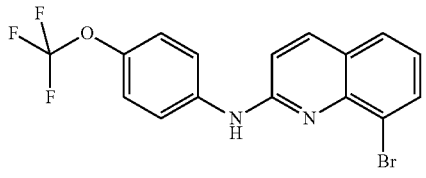 [SMILES: FC(F)(F)Oc1ccc(Nc2ccc3cccc(Br)c3n2)cc1]
120 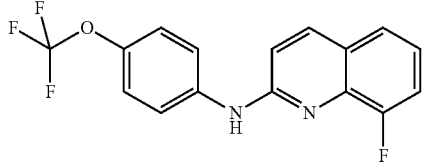 [SMILES: Fc1cccc2ccc(Nc3ccc(OC(F)(F)F)cc3)nc12]
121 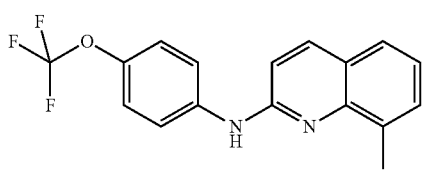 [SMILES: Cc1cccc2ccc(Nc3ccc(OC(F)(F)F)cc3)nc12]
122 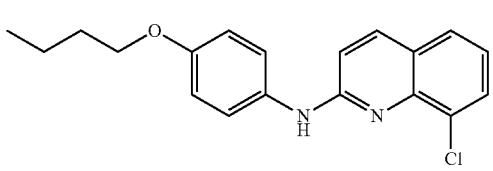 [SMILES: CCCCOc1ccc(Nc2ccc3cccc(Cl)c3n2)cc1]

TABLE 2-continued (compounds of formula (Ib) as defined above)

| # | Structure |
|---|---|
| 123 | |
| 124 | |
| 125 | |
| 126 | |
| 127 | |
| 128 | |
| 129 | |
| 130 | |
| 131 | |
| 132 | |
| 133 | |
| 134 | |
| 135 | |
| 136 | |

TABLE 2-continued (compounds of formula (Ib) as defined above)

TABLE 2-continued
(compounds of formula (Ib) as defined above)
152
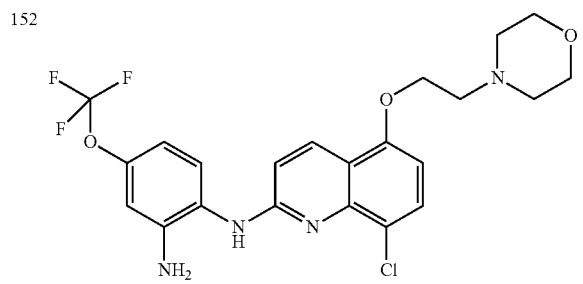
153
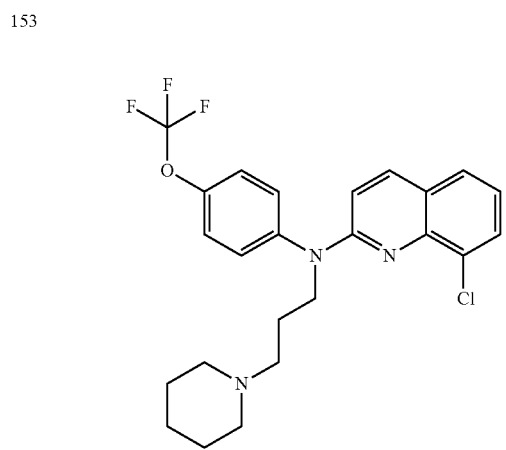
154
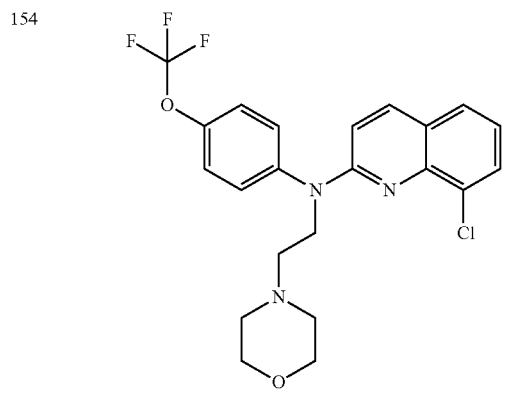
155
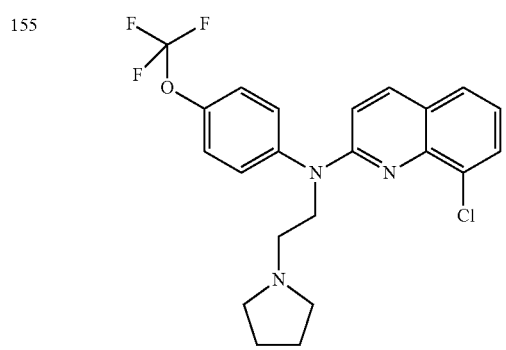
TABLE 2-continued
(compounds of formula (Ib) as defined above)
156
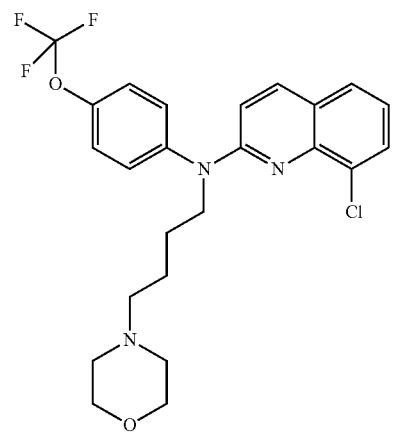 [SMILES: FC(F)(F)Oc1ccc(N(CCCCN2CCOCC2)c2ccc3cccc(Cl)c3n2)cc1]
157
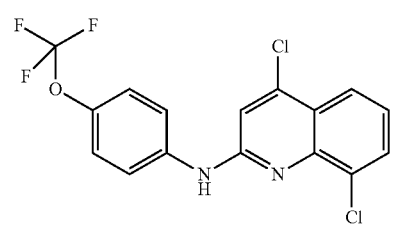 [SMILES: FC(F)(F)Oc1ccc(Nc2cc(Cl)c3cccc(Cl)c3n2)cc1]
158
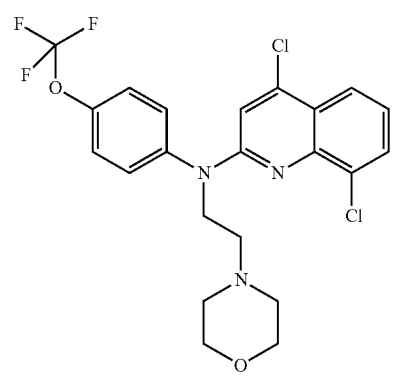 [SMILES: FC(F)(F)Oc1ccc(N(CCN2CCOCC2)c2cc(Cl)c3cccc(Cl)c3n2)cc1]
159
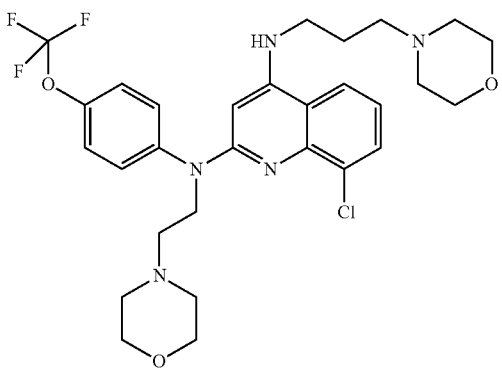 [SMILES: FC(F)(F)Oc1ccc(N(CCN2CCOCC2)c2cc(NCCCN3CCOCC3)c3cccc(Cl)c3n2)cc1]

TABLE 2-continued (compounds of formula (Ib) as defined above)

160 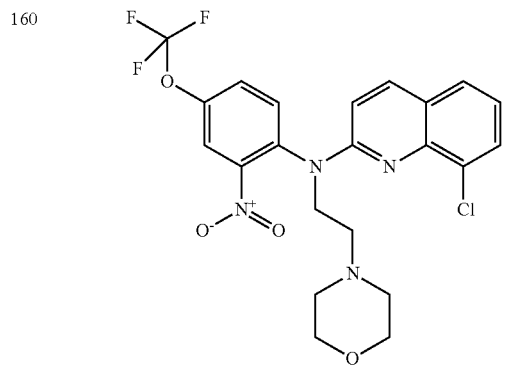

161 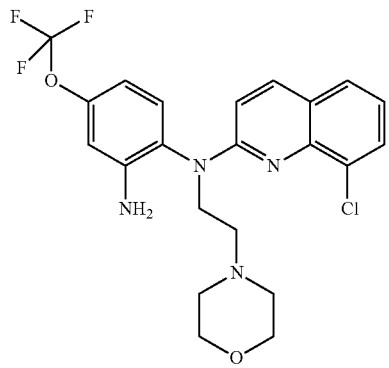 [SMILES: Nc1cc(OC(F)(F)F)ccc1N(CCN1CCOCC1)c1ccc2cccc(Cl)c2n1]

162 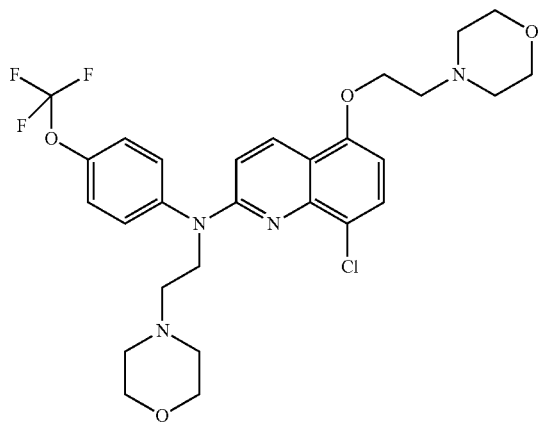 [SMILES: FC(F)(F)Oc1ccc(N(CCN2CCOCC2)c2ccc3c(OCCN4CCOCC4)ccc(Cl)c3n2)cc1]

163 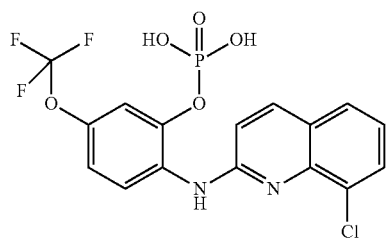 [SMILES: O=P(O)(O)Oc1cc(OC(F)(F)F)ccc1Nc1ccc2cccc(Cl)c2n1]

TABLE 2-continued (compounds of formula (Ib) as defined above)

164 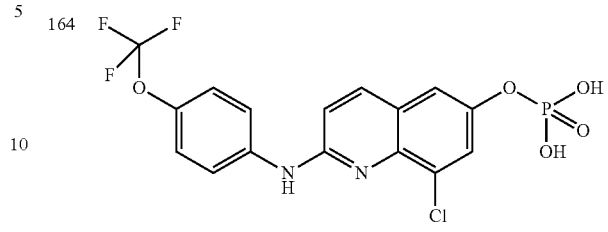

or a pharmaceutically acceptable salt thereof.

In some embodiments, the present invention provides a method for treating an inflammatory disease, disorder or condition comprising administering to a patient in need thereof a compound selected from Table 3:

TABLE 3

(compounds of formula (I) other that compounds (Ia) and (Ib))

165 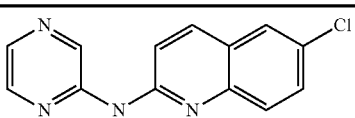

166 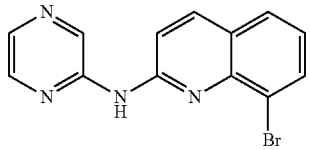 [SMILES: Brc1cccc2ccc(Nc3cnccn3)nc12]

167 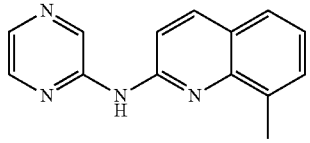 [SMILES: Cc1cccc2ccc(Nc3cnccn3)nc12]

168 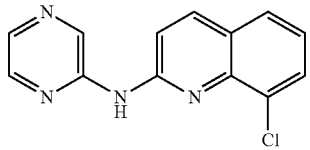 [SMILES: Clc1cccc2ccc(Nc3cnccn3)nc12]

169 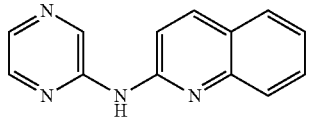 [SMILES: c1ccc2nc(Nc3cnccn3)ccc2c1]

170 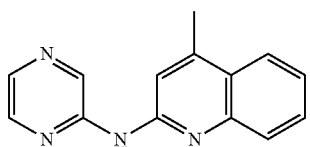

171 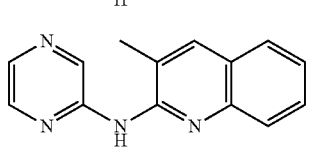

TABLE 3-continued (compounds of formula (I) other that compounds (Ia) and (Ib))

172 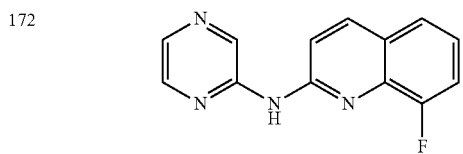

173 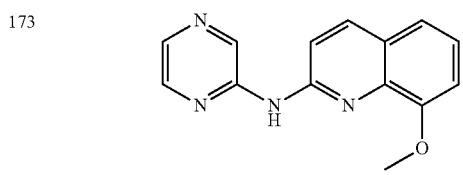

174 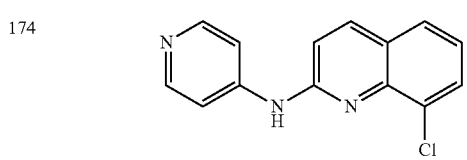

175 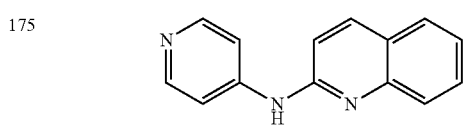

176 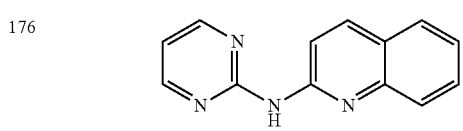

177 

178 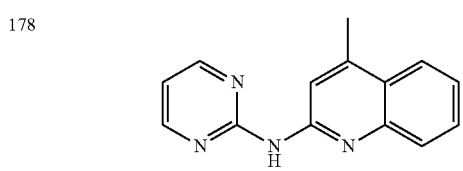

179 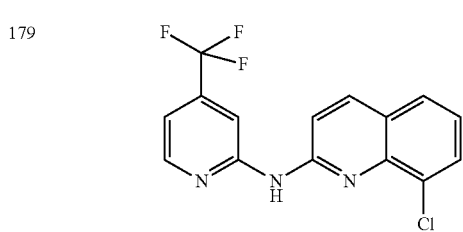

180 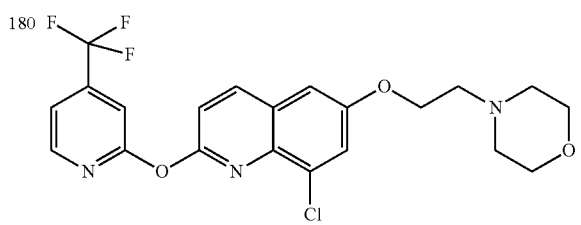

181 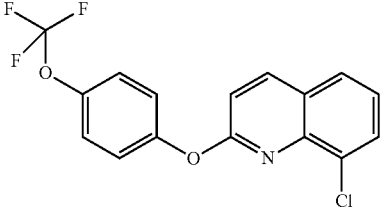 [SMILES: FC(F)(F)Oc1ccc(Oc2ccc3cccc(Cl)c3n2)cc1]

182 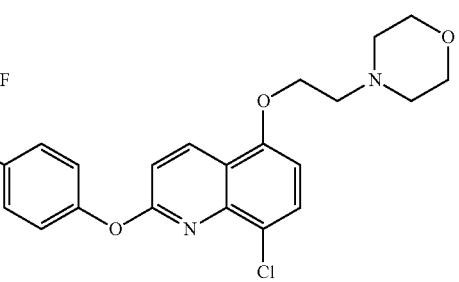

183 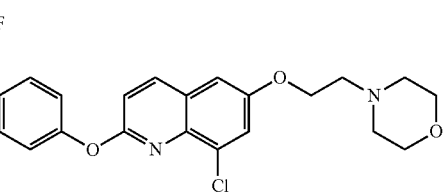

or a pharmaceutically acceptable salt thereof.

In some embodiments, a compound described herein is in a salt form selected from sulfate, hydrobromide, citrate, trifluoroacetate, ascorbate, hydrochloride, tartrate, triflate, maleate, mesylate, formate, acetate, fumarate, and sulfonate. In some embodiments, a compound described herein is in salt form as alkylsufonate or arylsulfonate. In some embodiments, a compound described herein is in salt form as mesylate, triflate, edisylate, besylate and tosylate.

In one aspect, the present invention provides a metabolite of a compound described herein. In some embodiments, the present invention provides a N-glucuronide metabolite of a compound described herein. In some embodiments, the present invention provides a method for treating an inflammatory disease, disorder or condition comprising administering to a patient in need thereof a N-glucuronide metabolite of a compound described herein.

In some embodiments, the present invention provides a compound of formula (IV):

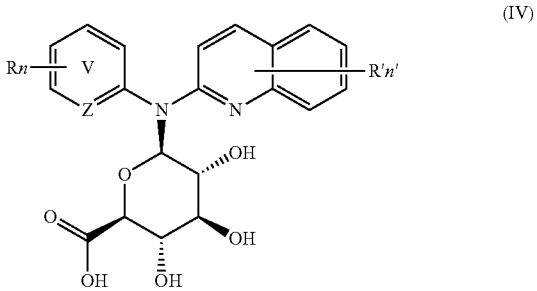

(IV)

or a pharmaceutically acceptable salt thereof, wherein each of variables V, Z, R, R', n, and n' is as defined above and described in embodiments herein, both singly or in combination, provided that the compound is not

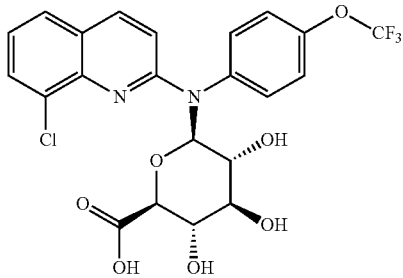 [SMILES: O=C(O)[C@H]1O[C@@H](N(c2ccc(OC(F)(F)F)cc2)c2ccc3cccc(Cl)c3n2)[C@H](O)[C@@H](O)[C@@H]1O]

In some embodiments, the present invention provides a compound of formula IVa:

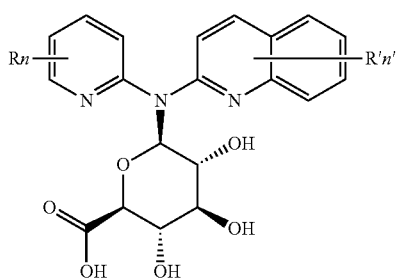

(IVa)

or a pharmaceutically acceptable salt thereof, wherein each of variables R, R', n, and n' is independently as defined above and described in embodiments herein, both singly and in combination.

In some embodiments, the present invention provides a compound of formula (IVb):

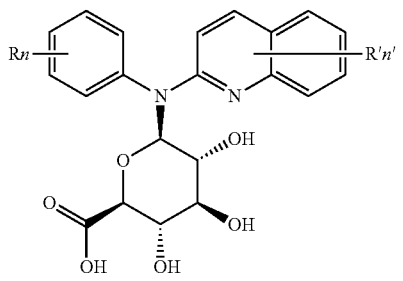

(IVb)

or a pharmaceutically acceptable salt thereof, wherein each of variables R, R', n, and n' is independently as defined above and described in embodiments herein, both singly and in combination, provided that the compound is not

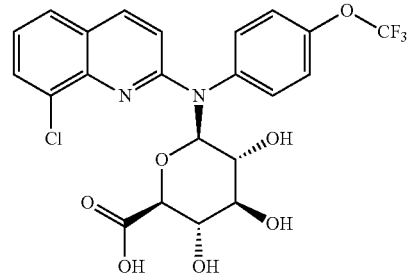 [SMILES: O=C(O)[C@H]1O[C@@H](N(c2ccc(OC(F)(F)F)cc2)c2ccc3cccc(Cl)c3n2)[C@H](O)[C@@H](O)[C@@H]1O]

In some embodiments, the present invention provides a compound of formula (IVc):

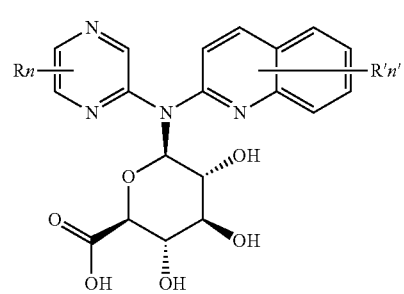

(IVc)

or a pharmaceutically acceptable salt thereof, wherein each of variables R, R', n, and n' is independently as defined above and described in embodiments herein, both singly and in combination.

In some embodiments, the present invention provides a compound of formula (IVb'):

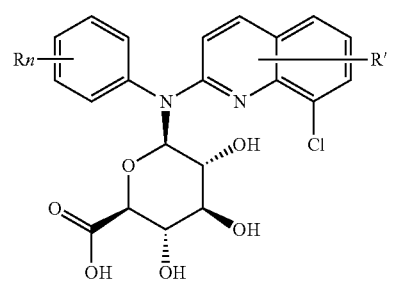

(IVb')

or a pharmaceutically acceptable salt thereof, wherein each of variables R, R', and n is independently as defined above and described in embodiments herein, both singly and in combination, provided that the compound is not

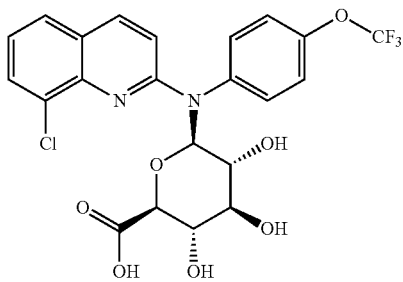 [SMILES: O=C(O)[C@H]1O[C@@H](N(c2ccc(OC(F)(F)F)cc2)c2ccc3cccc(Cl)c3n2)[C@H](O)[C@@H](O)[C@@H]1O]

In some embodiments, the present invention provides a compound of formula (IVd):

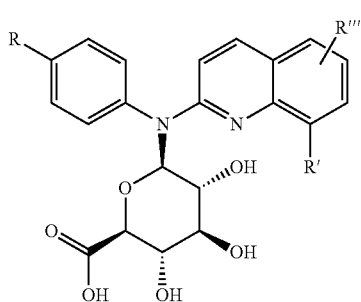

(IVd)

or a pharmaceutically acceptable salt thereof, wherein each of variables R, R', R''' is independently as defined above and described in embodiments herein, both singly and in combination, provided that the compound is not

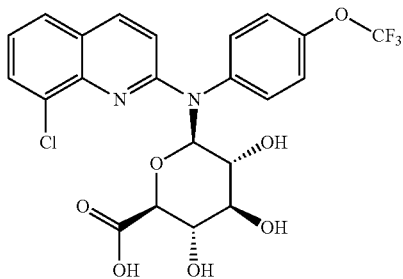 [SMILES: O=C(O)[C@H]1O[C@@H](N(c2ccc(OC(F)(F)F)cc2)c2ccc3cccc(Cl)c3n2)[C@H](O)[C@@H](O)[C@@H]1O]

In some embodiments, the present invention provides a method for treating an inflammatory disease, disorder or condition comprising administering to a patient in need thereof a compound of any one of formulas (IV), (IVa), (IVb), (IVc), (IVb') and (IVd), or a pharmaceutically acceptable salt thereof.

In some embodiments, the present invention provides a method for treating an inflammatory disease, disorder or condition comprising administering to a patient in need thereof a compound of formula:

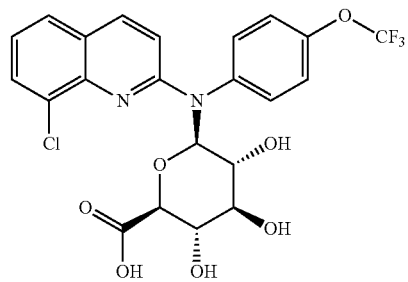 [SMILES: O=C(O)[C@H]1O[C@@H](N(c2ccc(OC(F)(F)F)cc2)c2ccc3cccc(Cl)c3n2)[C@H](O)[C@@H](O)[C@@H]1O]

or a pharmaceutically acceptable salt thereof.

In some embodiments, the present invention provides a compound of formula (IV):

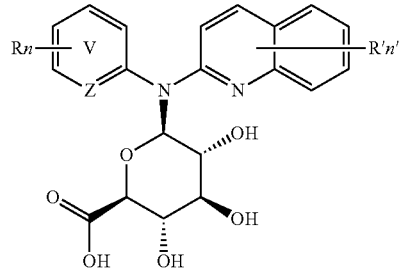

(IV)

or a pharmaceutically acceptable salt thereof, for use for treating and/or preventing an inflammatory disease, disorder or condition as defined above, wherein V, Z, R, R', n, and n' are as defined above.

The present invention further provides the compound of formula (IV) for use for treating and/or preventing an inflammatory disease, disorder or condition as defined above, wherein the compound is of formula (IVb):

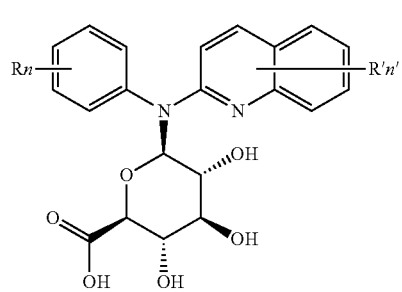

(IVb)

or a pharmaceutically acceptable salt thereof, wherein R, n, R', n' are as defined above.

Herein is further provided the compound of formula (IVb) for use for treating and/or preventing an inflammatory disease, disorder or condition as defined above, wherein the compound is of formula (IVb'):

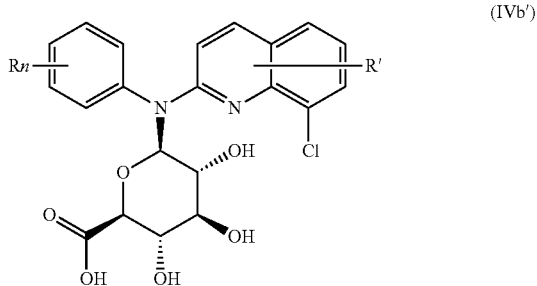

(IVb')

or a pharmaceutically acceptable salt thereof, wherein R, n, R', n' are as defined above.

Herein is further provided the compound of formula (IVb') for use for treating and/or preventing an inflammatory disease, disorder or condition as defined above, wherein said compound is

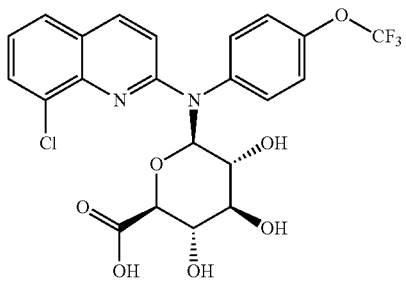 [SMILES: O=C(O)[C@H]1O[C@@H](N(c2ccc(OC(F)(F)F)cc2)c2ccc3cccc(Cl)c3n2)[C@H](O)[C@@H](O)[C@@H]1O]

or a pharmaceutically acceptable salt thereof.

In some embodiments, a method of the present invention for treating an inflammatory disease, disorder or condition further comprises measuring a level of a compound or a pharmaceutically acceptable salt thereof as described herein, or a metabolite thereof, in a patient. In some embodiments, a level of a compound or a pharmaceutically acceptable salt thereof as described herein, or a metabolite thereof, is measured in a patient's biological sample. In some embodiments, a patient's biological sample is a blood, plasma, tissue, saliva and/or serum sample.

In a further embodiment, the invention provides the compound (I), (Ib), (Ib'), (IV), (IVb) or (IVb') for use as defined above, for treating a patient, wherein the level of a compound of formula (I), (Ib), (Ib'), (IV), (IVb) or (IVb') as defined as defined above, or a pharmaceutically acceptable salt thereof, in a blood, plasma, tissue, saliva, and/or serum sample of the patient is measured during the use.

In some embodiments, a method of the present invention for treating an inflammatory disease, disorder or condition further comprises measuring a level of a compound of formula (I), (Ia), (Ib), (Ib'), (Ic), and (Id), or pharmaceutically acceptable salts thereof, in a patient. In some embodiments, a method of the present invention for treating an inflammatory disease, disorder or condition further comprises measuring a level of a compound of formulas (IV), (IVa), (IVb), (IVb'), (IVc), and (IVd), or pharmaceutically acceptable salts thereof, in a patient. In some embodiments, a method of the present invention for treating an inflammatory disease, disorder or condition further comprises measuring a total level of compounds of formulas (I) and (IV), or pharmaceutically acceptable salts thereof, in a patient. In some embodiments, a method of the present invention for treating an inflammatory disease, disorder or condition further comprises measuring a total level of compounds of formulas (I) and (IV), or pharmaceutically acceptable salts thereof, in a patient. In some embodiments, a method of the present invention for treating an inflammatory disease, disorder or condition further comprises measuring a total level of compounds of formulas (Ia) and (IVa), or pharmaceutically acceptable salts thereof, in a patient. In some embodiments, a method of the present invention for treating an inflammatory disease, disorder or condition further comprises measuring a total level of compounds of formulas (Ib) and (IVb), or pharmaceutically acceptable salts thereof, in a patient. In some embodiments, a method of the present invention for treating an inflammatory disease, disorder or condition further comprises measuring a total level of compounds of formulas (Ib') and (IVb'), or pharmaceutically acceptable salts thereof, in a patient. In some embodiments, a method of the present invention for treating an inflammatory disease, disorder or condition further comprises measuring a total level of compounds of formulas (Ic) and (IVc), or pharmaceutically acceptable salts thereof, in a patient. In some embodiments, a method of the present invention for treating an inflammatory disease, disorder or condition further comprises measuring a total level of compounds of formulas Id and (IVd), or pharmaceutically acceptable salts thereof, in a patient.

In some embodiments, a method of the present invention for treating an inflammatory disease, disorder or condition further comprises measuring and/or monitoring a presence and/or level of a biomarker in a patient. In some embodiments, a presence and/or level of a biomarker is measured in a patient's biological sample. In some embodiments, a patient's biological sample is a blood sample. In some embodiments, a patient's biological sample is a tissue sample. In some embodiments, a biomarker measured and/or monitored in a method of the present invention is miR-124, as described in WO 2014/111892, the entire content of which is incorporated herein by reference. In some embodiments, a method of the present invention for treating an inflammatory disease, disorder or condition further comprises measuring and/or monitoring a presence and/or expression level of miR-124 in a patient prior to administering a compound or a pharmaceutically acceptable salt or composition thereof as described herein. In some embodiments, a method of the present invention for treating an inflammatory disease, disorder or condition further comprises measuring and/or monitoring a presence and/or expression level of miR-124 in a patient during the course of a treatment with a compound or a pharmaceutically acceptable salt or composition thereof as described herein. In some embodiments, a method of the present invention for treating an inflammatory disease, disorder or condition further comprises selecting a patient for a treatment with a compound or a pharmaceutically acceptable salt or composition thereof as described herein, by measuring and/or monitoring a presence and/or expression level of miR-124 in the patient. In some embodiments, a method of the present invention for treating an inflammatory disease, disorder or condition further comprises excluding a patient from a treatment with a compound or a pharmaceutically acceptable salt or composition thereof as described herein, by measuring and/or monitoring a presence and/or expression level of miR-124 in the patient. In some embodiments, a method of the present invention for treating an inflammatory disease, disorder or condition further comprises adjusting (such as increasing or decreasing) dosage regimen (such as dose amount and/or dose schedule) of a compound or a pharmaceutically acceptable salt or composition thereof as described herein to be administered to a patient, by measuring and/or monitoring a presence and/or expression level of miR-124 in the patient.

In some embodiments, a method of the present invention for treating an inflammatory disease, disorder or condition comprises comparing a measured expression level of miR-124 in a patient to a control reference value. A control reference value to be used for comparing a measured expression level of miR-124 in a patient is obtained from a control sample. A control sample can be taken from various sources. In some embodiments, a control sample is taken from a patient prior to treatment or prior to the presence of a disease (such as an archival blood sample or tissue sample). In some embodiments, a control sample is taken from a set of normal, non-diseased members of a population. In some embodiments, a control sample is taken from a patient prior to treatment with a compound or a pharmaceutically acceptable salt or composition thereof as described herein. In some embodiments, a cell assay can be performed on a biological sample.

In some embodiments, a modulated presence and/or expression level of miR-124 in a patient compared to a control reference value indicates an inflammatory disease, disorder or condition. In some embodiments, a modulated presence and/or expression level of miR-124 in a patient compared to a control reference value indicates an efficacy of a treatment with a compound or a pharmaceutically acceptable salt or composition thereof as described herein, which is administered to the patient. The terms "modulation" or "modulated presence and/or expression level" means the presence or expression level of a biomarker is either induced or increased, or alternatively is suppressed or decreased.

In some embodiments, a measured reduced or suppressed presence, or a decreased expression level, of miR-124 relative to a control reference value indicates an inflammatory disease, disorder or condition. In some embodiments, a measured induced or increased presence, or an increased expression level, of miR-124 relative to a control reference value indicates an efficacy of a compound or a pharmaceutically acceptable salt or composition thereof as described herein. In some embodiments, a measured expression level of miR-124 in a patient treated with a compound or a pharmaceutically acceptable salt or composition thereof as described herein is a two-fold, four-fold, six-fold, eight-fold, or ten-fold increase relative to a control reference value.

Thus, according to a particular embodiment, the present invention further provides the compound of formula (I), (Ib), (Ib'), (IV), (IVb) or (IVb') for use as defined above, or pharmaceutically acceptable salts thereof, for treating a patient, wherein a presence and/or expression level of miR-124 in a blood and/or tissue sample of the patient is measured prior to and during the use.

In some embodiments, the present invention provides an algorithm that combines miR-124 level and the level of a cytokine or another biomarker, or levels of compounds of formulas (I) or (IV) or pharmaceutically acceptable salts thereof, to monitor severity of a disease, disorder, or condition, and/or to monitor efficacy of a treatment, including but not limited to a treatment as described herein. In some embodiments, a treatment method as described herein comprises using an algorithm that combines miR-124 level and the level of a cytokine or another biomarker, or levels of compounds of formulas (I) or (IV) or pharmaceutically acceptable salts thereof, to monitor severity of a disease, disorder, or condition, and/or to monitor efficacy of a treatment.

Herein is further provided the compound for use according to the present invention, wherein an algorithm that combines miR-124 level and the level of a cytokine or another biomarker, or levels of compounds of formulas (I) or (IV) as defined herein above or pharmaceutically acceptable salts thereof is used to monitor severity of a disease, disorder, or condition, and/or to monitor efficacy of the use or treatment.

Herein is further provided the compound for use according to the present invention, wherein an algorithm that combines miR-124 level and the level of a cytokine or another biomarker, or levels of compounds of formulas (I) or (IV) as defined herein above or pharmaceutically acceptable salts thereof is used to select patients for the use or treatment.

Herein is further provided an algorithm that combines miR-124 level and the level of a cytokine or another biomarker, or levels of compounds of formulas (I) or (IV) as defined above or pharmaceutically acceptable salts thereof to monitor severity of a disease, disorder, or condition, and/or to monitor efficacy of a treatment.

Thus, according to a particular embodiment, the present invention further provides the compound of formula (I), (Ib), (Ib'), (IV), (IVb) or (IVb') for use as defined above, wherein an algorithm that combines miR-124 level and the level of a cytokine or another biomarker, or levels of compounds of formulas the compound of formula (I), (Ib), (Ib'), (IV), (IVb) or (IVb'), or pharmaceutically acceptable salts thereof, is used to monitor severity of a disease, disorder, or condition, and/or to monitor efficacy of the use.

Uses, Formulation and Administration
Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an active metabolite or residue thereof.

A "biological sample" suitable for the present invention can be a biological fluid, such as a blood, a plasma, or a serum, a saliva, an interstitial, fluid, or a urine sample; a cell sample, such as a cell culture, a cell line, or a PBMC sample, a tissue biopsy, such as an oral tissue, a gastrointestinal tissue, a skin, an oral mucosa sample, or a plurality of samples from a clinical trial.

A biological sample can be a crude sample, or can be purified to various degrees prior to storage, processing, or measurement. In some embodiments, a biological sample is selected from the group consisting of a biological tissue sample, a whole blood sample, a swab sample, a plasma sample, a serum sample, a saliva sample, a vaginal fluid sample, a sperm sample, a pharyngeal fluid sample, a synovial sample, a bronchial or pleural fluid sample, a fecal fluid sample, a cerebrospinal fluid sample, a lacrymal fluid sample and a tissue culture supernatant sample.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers.

Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. Most preferably, pharmaceutically acceptable compositions of this invention are formulated for oral administration. Such formulations may be administered with or without food.

In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for treatment of an inflammatory disease, disorder or condition.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In some embodiments, the present invention provides a method for treating an inflammatory disease, disorder or condition comprising administering to a patient in need thereof a compound or composition as described herein.

Inflammatory Diseases, Disorders or Conditions

Compounds as described herein are useful in the treatment of inflammatory or obstructive airways diseases, resulting, for example, in reduction of tissue damage, airways inflammation, bronchial hyperreactivity, remodeling or disease progression. In some embodiments, an inflammatory disease, disorder, or condition is inflammatory or obstructive airways diseases including, but not limited to, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics.

Compounds as described herein are useful in the treatment of heteroimmune diseases. In some embodiments, an inflammatory disease, disorder, or condition is heteroimmune diseases including, but not limited to, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

Prophylactic efficacy in the treatment of asthma will be evidenced by reduced frequency or severity of symptomatic attack, e.g. of acute asthmatic or bronchoconstrictor attack, improvement in lung function or improved airways hyper-reactivity. It may further be evidenced by reduced requirement for other, symptomatic therapy, such as therapy for or intended to restrict or abort symptomatic attack when it occurs, for example anti-inflammatory or bronchodilatory. Prophylactic benefit in asthma may in particular be apparent in subjects prone to "morning dipping". "Morning dipping" is a recognized asthmatic syndrome, common to a substantial percentage of asthmatics and characterized by asthma attack, e.g. between the hours of about 4 to 6 am, i.e. at a time normally substantially distant form any previously administered symptomatic asthma therapy.

In some embodiments, an inflammatory disease, disorder, or condition is selected from acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. In some embodiments, an inflammatory disease, disorder, or condition is bronchitis, wherein the bronchitis is of whatever type or genesis including, but not limited to, acute, arachidic, catarrhal, croupus, chronic or phthinoid bronchitis. In some embodiments, an inflammatory disease, disorder, or condition is pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

In some embodiments, an inflammatory disease, disorder, or condition is an eosinophil related disorder, e.g. eosinophilia. In some embodiments, an eosinophil related disorder is an eosinophil related disorder of the airways (e.g. involving morbid eosinophilic infiltration of pulmonary tissues) including hypereosinophilia as it effects the airways and/or lungs as well as, for example, eosinophil-related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Compounds as described herein are also useful in the treatment of inflammatory or allergic conditions of the skin. In some embodiments, an inflammatory or allergic condition of the skin is selected from psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita, acne vulgaris, and other inflammatory or allergic conditions of the skin.

In some embodiments, an inflammatory disease, disorder, or condition is a disease or condition having an inflammatory component, for example, diseases and conditions of the eye such as ocular allergy, conjunctivitis, keratoconjunctivitis sicca, uveitis and vernal conjunctivitis, diseases and conditions affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca, uveitis, and vernal keratoconjunctivitis, interstitial lung fibrosis, psoriatic arthritis, systemic juvenile idiopathic arthritis, cryopyrin-associated periodic syndrome, Muckle-Wells syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, intestinal failure, hyperchlolesterolemia, heart disease, chronic heart failure, mesothelioma, anhidrotic ecodermal dysplasia, Behcet's disease, incontinentia pigmenti, Paget's disease, acute or chronic pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments, an inflammatory disease, disorder, or condition is acute or chronic graft rejection in kidney, liver, heart, pulmonary transplantation, or graft versus-host disease in bone marrow graft.

In some embodiments, an inflammatory disease, disorder, or condition is an inflammatory disease, disorder, or condition of the skin. In some embodiments, an inflammatory disease, disorder, or condition of the skin is selected from contact dermatitits, atopic dermatitis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, and other inflammatory or allergic conditions of the skin.

In some embodiments, an inflammatory disease, disorder, or condition is selected from acute and chronic gout, chronic gouty arthritis, psoriasis, psoriatic arthritis, rheumatoid arthritis, Juvenile rheumatoid arthritis, Systemic juvenile idiopathic arthritis (SJIA), Cryopyrin Associated Periodic Syndrome (CAPS), Muckle-Wells syndrome, and osteoarthritis.

In some embodiments, an inflammatory disease, disorder, or condition is a TH17 mediated disease. In some embodiments, a TH17 mediated disease is selected from Systemic lupus erythematosus, Multiple sclerosis, and inflammatory bowel disease (including Crohn's disease or ulcerative colitis).

In some embodiments, an inflammatory disease, disorder, or condition is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis.

In some embodiments, an inflammatory disease, disorder, or condition is associated with transplantation. In some embodiments, an inflammatory disease, disorder, or condition is associated with organ transplantation, organ transplant rejection, and/or graft versus host disease. In some embodiments, an inflammatory disease, disorder, or condition is an autoimmune disorder. In some embodiments an autoimmune disorder is type 1 diabetes, systemic lupus erythematosus, multiple sclerosis, psoriasis, Behçet's disease, POEMS syndrome, Crohn's disease, ulcerative colitis, ankylosing spondylitis, axial spondyloarthritis, primary biliary cirrhosis, autoimmune hepatitis, or inflammatory bowel disease.

In some embodiments, an inflammatory disease, disorder, or condition is an inflammatory disorder. In some embodiments, an inflammatory disorder is rheumatoid arthritis, asthma, chronic obstructive pulmonary disease, psoriasis, hepatomegaly, Crohn's disease, ulcerative colitis, ankylosing spondylitis, axial spondyloarthritis, primary biliary cirrhosis, polymyalgia rheumatica, giant cell arteritis, or inflammatory bowel disease.

In some embodiments, the present invention provides a method for treating an inflammatory disease, disorder, or condition in the pancreas. In some embodiments, an inflammatory disease, disorder, or condition in the pancreas is selected from diabetes type-1, diabetes type-2, acute and chronic pancreatitis.

In some embodiments, the present invention provides a method for treating an inflammatory disease, disorder, or condition in the kidney. In some embodiments, an inflammatory disease, disorder, or condition in the kidney is selected from glomerulosclerosis, glomerulonephritis, nephritis, acute kidney injury, Berger's disease, Goodpasture's syndrome, Wegener's granulomatosis, and kidney transplant acute or chronic rejection.

In some embodiments, the present invention provides a method for treating an inflammatory disease, disorder, or condition in the liver. In some embodiments, an inflammatory disease, disorder, or condition in the liver is selected from nonalcoholic steatohepatitis (NASH), non-alcoholic fatty liver disease (NAFLD), cholestatic liver disease, sclerosing cholangitis, and liver transplant acute or chronic rejection.

Herein is further provided the compound for formula (I), (Ib) or (Ib') as defined above, for use as defined above, wherein the inflammatory disease, disorder or condition is in the liver selected from nonalcoholic steatohepatitis (NASH), non-alcoholic fatty liver disease (NAFLD), cholestatic liver disease, sclerosing cholangitis and liver transplant acute or chronic rejection.

Nonalcoholic fatty liver disease (NAFLD) in fact encompasses various diseases extending from nonalcoholic fatty liver (NAFL) to nonalcoholic steatohepatitis (NASH). Diagnosis of said diseases nowadays implies a liver biopsy, which is invasive. In addition, there is a need for having suitable treatments.

NAFLD is characterized by predominantly macrovesicular steatosis and the presence of visible steatosis on >5% of hepatocytes is generally accepted as a working definition of fatty liver. NAFLD activity score (NAS) is generally used to define and quantify disease activity, from the evaluation of the severity of ongoing liver injury observed in a liver biopsy. NAS is thus one of the clinical endpoints for assessing the activity of NASH (Sanyal A J. et al., Hepatology, 2011; 54:344). Scoring is based on evaluation of the severity of steatosis (0-3), inflammation (0-3) and hepatocellular ballooning (0-2).

As apparent from example 2 herein after, 8-Chloro-N-(4-(trifluoromethoxy)phenyl)quinolin-2-amine and its metabolite of formula

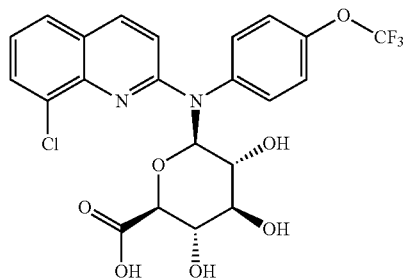 [SMILES: O=C(O)[C@H]1O[C@@H](N(c2ccc(OC(F)(F)F)cc2)c2ccc3cccc(Cl)c3n2)[C@H](O)[C@@H](O)[C@@H]1O]

were tested in STAM model of non-alcoholic steatohepatitis, a well-established model for assessing the activity of compounds in the treatment of NASH. Said compounds both showed a decreasing trend in NAS compared with the Vehicle group, predictive for their use in the treatment of cholestatic liver disease, sclerosing cholangitis and NAFLD, including NAFL and NASH.

Furthermore, still as demonstrated in example 2, points 4.3 and 4.4 herein after, 8-Chloro-N-(4-(trifluoromethoxy) phenyl)quinolin-2-amine decreases Alpha-SMA and decreased F4/80-positive area in the liver.

In some embodiments, the present invention provides a method for treating an inflammatory disease, disorder, or condition in the lung or heart. In some embodiments, an inflammatory disease, disorder, or condition in the lung is selected from chronic obstructive pulmonary disease (COPD), asthma, pulmonary fibrosis, pulmonary hypertension, sarcoidosis, myocarditis, pericarditis and lung or heart transplant acute or chronic rejection.

Herein is further provided the compound for formula (I), (Ib) or (Ib') as defined above, for use as defined above, wherein the inflammatory disease, disorder or condition is selected from chronic obstructive pulmonary disease (COPD), asthma, pulmonary fibrosis, pulmonary hypertension, sarcoidosis, myocarditis, pericarditis and lung or heart transplant acute or chronic rejection.

As apparent from example 3 herein after, 8-Chloro-N-(4-(trifluoromethoxy)phenyl)quinolin-2-amine showed a tendency to decrease mean pulmonary arterial pressure at 70 mg/kg when tested in the Sugen hypoxia model.

As apparent from example 4 herein after, 8-Chloro-N-(4-(trifluoromethoxy)phenyl)quinolin-2-amine reduces significantly the pulmonary pressure in female rat where pulmonary hypertension has been induced by monocrotaline in the rat monocrotaline model of pulmonary arterial hypertension.

All said results are predictive for their use in the treatment of pulmonary fibrosis, pulmonary hypertension, sarcoidosis, myocarditis and pericarditis.

In some embodiments, the present invention provides a method for treating an inflammatory disease, disorder, or condition in the skin. In some embodiments, an inflammatory disease, disorder, or condition in the skin is selected from contact dermatitits, atopic dermatitis, psoriasis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, acnea, keloid scar, and other inflammatory or allergic conditions of the skin.

In some embodiments, the present invention provides a method for treating an inflammatory disease, disorder, or condition in the vessel/blood. In some embodiments, an inflammatory disease, disorder, or condition in the vessel/blood is selected from Behcet's disease, vasculitis, sepsis, tumor angiogenesis, atherosclerosis, proliferative vascular disease, and restenosis.

In some embodiments, the present invention provides a method for treating an inflammatory disease, disorder, or condition in the eye. In some embodiments, an inflammatory disease, disorder, or condition in the eye is selected from conjunctivitis, scleritis, episcleritis, panuveitis, choroiditis, chorioretinitis, neuroretinitis, uveitis, orbital inflammatory disease, and optical neuritis.

In some embodiments, the present invention provides a method for treating an inflammatory disease, disorder, or condition in the central or peripheral nervous system. In some embodiments, an inflammatory disease, disorder, or condition in the central or peripheral nervous system is selected from non-viral and viral encephalitis and meningitis, depression, neuropathic pain, including chronic pain, traumatic brain injury, including stroke, Alzheimer disease, Parkinson disease, Myelitis, Charcot-Marie-Tooth disease type 1 (including CMT1A and CMT1B), Multiple sclerosis, Amyotrophic lateral sclerosis (ALS), Creutzfeldt-Jakob disease, demyelinating polyneuropathy and peripheral neuropathy.

In some embodiments, the present invention provides a method for treating an autoimmune disease, disorder, or condition. In some embodiments, an autoimmune disease, disorder, or condition is selected from Lupus, including in the skin and kidney, Guillain-Barre syndrome, Myasthenia gravis, Hashimoto's thyroiditis, idiopathic purpura, aplastic anemia, Graves disease, and Myocarditis.

In some embodiments, the present invention provides a method for treating an inflammatory disease, disorder, or condition in the intestine. In some embodiments, an inflammatory disease, disorder, or condition in the intestine is selected from intestinal failure, Ulcerative colitis, and Crohn's disease.

In some embodiments, the present invention provides a method for treating an inflammatory disease, disorder, or condition in the reproductive system. In some embodiments, an inflammatory disease, disorder, or condition in the reproductive system is selected from endometriosis, uterine fibroma, prostate dysplasia or growth, and cervix dysplasia.

In some embodiments, the present invention provides a method for treating an inflammatory disease, disorder, or condition in the bone and/or joints. In some embodiments, an inflammatory disease, disorder, or condition in the bone and/or joints is selected from juvenile idiopathic arthritis, psoriatic arthritis, periodontitis, and hand, foot, ankle, knee, hip, shoulder, elbow or spine arthritis and/or demineralization.

Combination Therapies

Depending upon the particular condition, or disease, to be treated, additional therapeutic agents, which are normally administered to treat that condition, may be administered in combination with compounds and compositions as described herein. As used herein, additional therapeutic agents that are normally administered to treat a particular disease, or condition, are known as "appropriate for the disease, or condition, being treated."

In certain embodiments, the present invention provides a method for treating an inflammatory disease, disorder, or condition, comprising administering to a patient in need thereof a compound or composition as described herein in combination with another therapeutic agent.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The combination may result in an additive, or in a synergistic effect, where lower doses of one or both of the compound may be used to obtain a similar efficacy, or where the same doses may result in a significantly improved efficacy.

In some embodiments, the present invention provides a composition comprising a compound as described herein and one or more additional therapeutic agents. The therapeutic agent may be administered together with a compound as described herein, or may be administered prior to or following administration of a compound as described herein. Suitable therapeutic agents are described in further detail below. In certain embodiments, a compound as described herein may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In certain embodiments, a compound as described herein may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In some embodiments, the present invention provides a method of treating an inflammatory disease, disorder or condition by administering to a patient in need thereof a compound as described herein and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®, Neoral®), tacrolimus, sirolimus, mycophenolate, leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), anti-T cell antibodies such as Thymoglobulin, IV Immunoglobulins (IVIg), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), anti-IL36 agents such as BI655130, Dihydroorotate dehydrogenase inhibitors such as IMU-838, anti-OX40 agents such as KHK-4083, microbiome agents such as RBX2660, SER-287, Narrow spectrum kinase inhibitors such as TOP-1288, anti-CD40 agents such as BI-655064 and FFP-104, guanylate cyclase agonists such as dolcanatide, sphingosine kinase inhibitors such as opaganib, anti-IL-12/IL-23 agents such as AK-101, Ubiquitin protein ligase complex inhibitors such as BBT-401, sphingosine receptors modulators such as BMS-986166, P38MAPK/PDE4 inhibitors such as CBS-3595, CCR9 antagonists such as CCX-507, FimH antagonists such as EB-8018, HIF-PH inhibitors such as FG-6874, HIF-1α stabilizer such as GB-004, MAP3K8 protein inhibitors such as GS-4875, LAG-3 antibodies such as GSK-2831781, RIP2 kinase inhibitors such as GSK-2983559, Farnesoid X receptor agonist such as MET-409, CCK2 antagonists such as PNB-001, IL-23 Receptor antagonists such as PTG-200, Purinergic P2X7 receptor antagonists such as SGM-1019, PDE4 inhibitors such as Apremilast, ICAM-1 inhibitors such as alicaforsen sodium, Anti-TL23 agents such as guselkumab, brazikumab and mirkizumab, ant-IL-15 agents such as AMG-714, TYK-2 inhibitors such as BMS-986165, NK Cells activators such as CNDO-201, RIP-1 kinase inhibitors such as GSK-2982772, anti-NKGD2 agents such as JNJ-4500, CXCL-10 antibodies such as JT-02, IL-22 receptor agonists such as RG-7880, GATA-3 antagonists such as SB-012 and Colony-stimulating factor-1 receptor inhibitors such as edicotinib or any combination(s) thereof.

In another embodiment, the present invention provides a method of treating gout comprising administering to a patient in need thereof a compound as described herein and one or more additional therapeutic agents selected from non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol and febuxostat (Uloric®).

In another embodiment, the present invention provides a method of treating rheumatoid arthritis comprising administering to a patient in need thereof a compound as described herein and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound as described herein and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating lupus comprising administering to a patient in need thereof a compound as described herein and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating Crohn's disease, ulcerative colitis, or inflammatory bowel disease comprising administering to a patient in need thereof a compound as described herein and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound as described herein and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-bid®, Uniphyl®, Theo-24®) and aminophylline, and IgE antibodies such as omalizumab (Xolair®).

In some embodiments, the present invention provides a method of treating COPD comprising administering to a patient in need thereof a compound as described herein and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®.

In some embodiments, the present invention provides a method of treating HIV comprising administering to a patient in need thereof a compound as described herein and one or more additional therapeutic agents selected from nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), and combinations thereof.

In some embodiments, the present invention provides a method of treating organ transplant rejection or graft vs. host disease comprising administering to a patient in need thereof a compound as described herein and one or more additional therapeutic agents selected from a steroid, cyclosporin, FK506, rapamycin, a hedgehog signaling inhibitor, a BTK inhibitor, a JAK/pan-JAK inhibitor, a TYK2 inhibitor, a PI3K inhibitor, and a SYK inhibitor.

The compounds and compositions, according to the method of the present invention, may be administered using any amount and any route of administration effective for treating or lessening the severity of an inflammatory disease, disorder or condition. The exact amount required will vary from subject to subject, depending on the species, age, and general condition of the subject, the severity of the disease or condition, the particular agent, its mode of administration, and the like. Compounds as described herein are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds as described herein with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular eight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch.

Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches.

The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, $CGSO_{25019}C$, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-5 351591 (Schering-Plough), Arofylline (Almirall Prodesfarma), PD189659/PD168787 (ParkeDavis), AWD-12-281 (Asta Medica), CDC-801 (Celgene), SeICID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-

(4-methylphenyl)-5H-benzo-cyclohepten-8-yl]carbonyl] amino]phenyl]-methyl]tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refer to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both a compound as described herein and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

In addition to the prevention and/or treatment methods as described above, the present invention also provides the corresponding use for preventing and/or treating a disease, disorder, or condition as described herein. In some embodiments, the present invention provides a use of a compound or a pharmaceutically acceptable salt thereof, as described herein, for preventing and/or treating an inflammatory disease, disorder, or condition as described herein. In some embodiments, a use for preventing and/or treating an inflammatory disease, disorder, or condition as provided by the invention, is intended for a patient whose presence and/or expression level of miR-124 is measured and/or monitored by the methods as described herein.

Herein is further provided a compound of formulas (I), (Ia), (Ib), (Ib'), (Ic), (Id), (IV), (IVa), (IVb), (IVb'), (IVc), or (IVd) as defined above, or a pharmaceutically acceptable salt thereof, for use for treating or preventing an inflammatory disease, disorder or condition in a patient in need thereof, wherein the inflammatory disease, disorder or condition is selected from:

(a) an inflammatory disease, disorder, or condition in the pancreas selected from diabetes type-1, diabetes type-2, acute and chronic pancreatitis;

(b) an inflammatory disease, disorder, or condition in the kidney selected from glomerulosclerosis, glomerulonephritis, nephritis, acute kidney injury, Berger's disease, Goodpasture's syndrome, Wegener's granulomatosis and kidney transplant acute or chronic rejection;

(c) an inflammatory disease, disorder, or condition in the liver selected from nonalcoholic steatohepatitis (NASH), non-alcoholic fatty liver disease (NAFLD), cholestatic liver disease, sclerosing cholangitis and liver transplant acute or chronic rejection;

(d) an inflammatory disease, disorder, or condition in the lung or heart selected from chronic obstructive pulmonary disease (COPD), asthma, pulmonary fibrosis, pulmonary hypertension, sarcoidosis, myocarditis, pericarditis and lung or heart transplant acute or chronic rejection;

(e) an inflammatory disease, disorder, or condition in the skin selected from contact dermatitits, atopic dermatitis, psoriasis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, acnea, keloid scar, and other inflammatory or allergic conditions of the skin;

(f) an inflammatory disease, disorder, or condition in the vessel/blood selected from Behcet's disease, vasculitis, sepsis, tumor angiogenesis, atherosclerosis, proliferative vascular disease and restenosis;

(g) an inflammatory disease, disorder, or condition in the eye selected from conjunctivitis, scleritis, episcleritis, panuveitis, choroiditis, chorioretinitis, neuroretinitis, uveitis, orbital inflammatory disease, and optical neuritis;

(h) an inflammatory disease, disorder, or condition in the central or peripheral nervous system selected from non-viral and viral encephalitis and meningitis, depression, neuropathic pain, including chronic pain, traumatic brain injury, including stroke, Alzheimer disease, Parkinson disease, Myelitis, Charcot-Marie-Tooth disease type 1 (including CMT1A and CMT1B), Multiple sclerosis, Amyotrophic lateral sclerosis (ALS), Creutzfeldt-Jakob disease, demyelinating polyneuropathy and peripheral neuropathy;

(i) an autoimmune disease, disorder, or condition selected from Lupus, including in the skin and kidney, Guillain-Barre syndrome, Myasthenia gravis, Hashimoto's thyroiditis, idiopathic purpura, aplastic anemia, Graves disease, and Myocarditis;

(j) an inflammatory disease, disorder, or condition in the intestine selected from intestinal failure, Ulcerative colitis and Crohn's disease;

(k) an inflammatory disease, disorder, or condition in the reproductive system selected from endometriosis, uterine fibroma, prostate dysplasia or growth, and cervix dysplasia; and (l) an inflammatory disease, disorder, or condition in the bone and/or joints selected from juvenile idiopathic arthritis, psoriatic arthritis, periodontitis, and hand, foot, ankle, knee, hip, shoulder, elbow or spine arthritis and/or demineralization.

Herein is further provided a compound of formulas (I), (Ia), (Ib), (Ib'), (Ic), (Id), (IV), (IVa), (IVb), (IVb'), (IVc), or (IVd) as defined above, or a pharmaceutically acceptable salt thereof, for use as an anti-inflammatory agent intended for patients whose presence and/or expression level of miR-124 is monitored in a blood and/or tissue sample of said patient, prior to and/or during the course of said use of the anti-inflammatory agent.

Animal preclinical models may be used to assess the anti-inflammatory activities of 8-Chloro-N-(4-(trifluoromethoxy)phenyl)quinolin-2-amine and its metabolites under any form or one of its pharmaceutically acceptable salt.

Example 1

For example, in the model of mouse IMQ-Induced psoriasis. Psoriasis may be induced by daily dosing of IMQ, for example for 0 to 9 days, and treatment may be administered daily, for example from day 0 to day 9. Anti-inflammatory activities may be assessed, for example by measuring psoriasis score.

For example, in the MPTP-induced mouse model of Parkinson's Disease where mice may receive for example 4 intraperitoneal (IP) injections of 20 mg/ml MPTP at 2 hours intervals on day 0. Treatment may be administered daily for example from day 0 to day 7. Anti-inflammatory activities may be assessed for example by TH immunoreactive analysis at the level of the Substantia Nigra pars compacta (SNpc).

For example, in the MOG-induced Murine Model of Experimental Autoimmune Encephalomyelitis EAE). EAE may be induced for example by injections of the MOG/CFA inoculation over the paralumbar regions on study day 0. And in order to increase the permeability of the blood-brain barrier (BBB), all animals may be subjected for example to supplemental immunostimulation by Pertussis Toxin (PT) via intraperitoneal injections on study days 0 and 2. Treatment may be administered daily, for example from day 0, day 3 or day 10 and anti-inflammatories activities may be measured, for example by clinical score or/and Histological assessment of spinal cord via H&E staining to evaluate cell infiltration and demyelination and/or CNS/Pain parameters evaluation. For example, in the NOD Spontaneous model of Diabetes in Mice. The treatment may be administered daily and anti-inflammatory activities may be assessed, for example by blood glucose level and/or oral glucose tolerance test.

In the following examples, Compound A is 8-Chloro-N-(4-(trifluoromethoxy)phenyl)quinolin-2-amine or ABX464 and compound B is its metabolite of formula

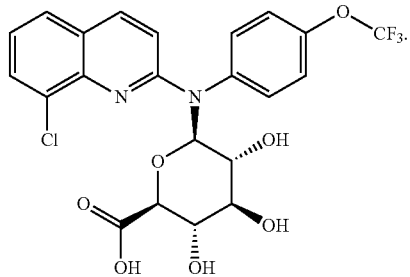 [SMILES: O=C(O)[C@H]1O[C@@H](N(c2ccc(OC(F)(F)F)cc2)c2ccc3cccc(Cl)c3n2)[C@H](O)[C@@H](O)[C@@H]1O]

Example 2: In Vivo Efficacy Study of Compounds in STAM Model of Non-Alcoholic Steatohepatitis (NASH Study)

A. Materials and Methods

1. Test Substances

To prepare dosing solution, Compound A and B were weighed and suspended in Vehicle which was composed of 20% of Vehicle-A1 and 80% of Vehicle-A2. Vehicle-A1 was composed of 0.5% (w/v) Carboxymethyl cellulose (CMC) 400-800 centipoises in water for injection+2.5% (w/v) Tween 80. Vehicle-A2 was composed of 0.5% (w/v) Carboxymethyl cellulose (CMC) 400-800 centipoises in water for injection. Telmisartan (Micardis®) was purchased from Boehringer Ingelheim GmbH (Germany) and dissolved in pure water.

2. Induction of NASH

NASH was induced in 48 male mice by a single subcutaneous injection of 200 μg streptozotocin (STZ, Sigma-Aldrich, USA) solution 2 days after birth and feeding with high fat diet (HFD, 57 kcal % fat, Cat #HFD32, CLEA Japan, Inc., Japan) after 4 weeks of age.

3. Route of Drug Administration

Compound A and B, and Telmisartan were administered orally in a volume of 10 mL/kg.

4. Treatment Doses

Compound A was administered at 3 dose levels of 10, 20 and 40 mg/kg once daily from 6 to 9 weeks of age. Compound B was administered at a dose of 40 mg/kg once daily from 6 to 9 weeks of age. Telmisartan was administered at a dose of 10 mg/kg once daily from 6 to 9 weeks of age.

5. Animals

C57BL/6 mice (14-day-pregnant female) were obtained from Japan SLC, Inc. (Japan). All animals used in the study were housed and cared for in accordance with the Japanese Pharmacological Society Guidelines for Animal Use.

The animals were maintained in a SPF facility under controlled conditions of temperature (23±3° C.), humidity (50±20%), lighting (12-hour artificial light and dark cycles; light from 8:00 to 20:00) and air exchange. A high pressure was maintained in the experimental room to prevent contamination of the facility.

The animals were housed in TPX cages (CLEA Japan) with a maximum of 4 mice per cage. Sterilized Palmas-µ (Material Research Center, Japan) was used for bedding and replaced once a week.

Sterilized solid HFD was provided ad libitum, being placed in a metal lid on the top of the cage. Pure water was provided ad libitum from a water bottle equipped with a rubber stopper and a sipper tube. Water bottles were replaced once a week, cleaned, and sterilized in an autoclave and reused.

Mice were identified by ear punch. Each cage was labeled with a specific identification code.

6. Measurement of Plasma Biochemistry

For plasma biochemistry, non-fasting blood was collected in polypropylene tubes with anticoagulant (Novo-Heparin, Mochida Pharmaceutical Co. Ltd., Japan) and centrifuged at 1,000×g for 15 minutes at 4° C. The supernatant was collected and stored at −80° C. until use. Plasma ALT was measured by FUJI DRI-CHEM 7000 (Fujifilm, Japan).

7. Measurement of Liver Triglyceride Content

Liver total lipid-extracts were obtained by Folch's method (Folch J. et al., J. Biol. Chem. 1957; 226: 497). Liver samples were homogenized in chloroform-methanol (2:1, v/v) and incubated overnight at room temperature. After washing with chloroform-methanol-water (8:4:3, v/v/v), the extracts were evaporated to dryness, and dissolved in isopropanol. Liver triglyceride content was measured by Triglyceride E-test (FUJIFILM Wako Pure Chemical Corporation, Japan).

8. Histological Analyses

For HE staining, sections were cut from paraffin blocks of liver tissue prefixed in Bouin's solution and stained with Lillie-Mayer's Hematoxylin (Muto Pure Chemicals Co., Ltd., Japan) and eosin solution (FUJIFILM Wako Pure Chemical Corporation). NAFLD Activity score (NAS) was calculated according to the criteria of Kleiner (Kleiner D E. et al., Hepatology, 2005; 41:1313). To visualize collagen deposition, Bouin's fixed liver sections were stained using picro-Sirius red solution (Waldeck, Germany). For quantitative analysis of fibrosis area, bright field images of Sirius red-stained sections were captured around the central vein using a digital camera (DFC295; Leica, Germany) at 200-fold magnification, and the positive areas in 5 fields/section were measured using ImageJ software (National Institute of Health, USA).

9. Sample Collection

For plasma samples, non-fasting blood was collected in polypropylene tubes with anticoagulant (Novo-Heparin) and centrifuged at 1,000×g for 15 minutes at 4° C. The 20 µL of supernatant was collected and stored at −80° C. for biochemistry. The remaining plasma was collected and stored at −80° C. for shipping.

For frozen liver samples, left lateral lobe was collected and cut into 6 pieces. Two pieces of left lateral lobe, left and right medial lobes, and caudate lobe were snap frozen in liquid nitrogen and stored at −80° C. for shipping. The other 2 pieces of left lateral lobe were fixed in Bouin's solution and then embedded in paraffin. Paraffin blocks were stored at room temperature for histology. The remaining pieces of left lateral lobe were embedded in O.C.T. compound and quick frozen in liquid nitrogen. Samples were stored at −80° C. Right lobe was snap frozen in liquid nitrogen and stored at −80° C. for liver biochemistry.

10. Statistical Tests

Statistical analyses were performed using Bonferroni Multiple Comparison Test on GraphPad Prism 6 (GraphPad Software Inc., USA). P values <0.05 were considered statistically significant. A trend or tendency was demonstrated when a one-tailed t-test returned P values <0.1. Results were expressed as mean±SD.

B. Experimental Design and Treatment

1. Study Groups

Group 1: Vehicle Eight NASH mice were orally administered vehicle [20% of Vehicle-A1 and 80% of Vehicle-A2] in a volume of 10 mL/kg once daily from 6 to 9 weeks of age.

Group 2: Compound A Low

Eight NASH mice were orally administered vehicle supplemented with Compound A at a dose of 10 mg/kg once daily from 6 to 9 weeks of age.

Group 3: Compound A Middle

Eight NASH mice were orally administered vehicle supplemented with Compound A at a dose of 20 mg/kg once daily from 6 to 9 weeks of age.

Group 4: Compound A High

Eight NASH mice were orally administered vehicle supplemented with Compound A at a dose of 40 mg/kg once daily from 6 to 9 weeks of age.

Group 5: Compound B

Eight NASH mice were orally administered vehicle supplemented with Compound B at a dose of 40 mg/kg once daily from 6 to 9 weeks of age.

Group 6: Telmisartan

Eight NASH mice were orally administered pure water supplemented with Telmisartan at a dose of 10 mg/kg once daily from 6 to 9 weeks of age.

The table 4 below summarizes the treatment schedule:

TABLE 4

| Group | No. mice | Mice | Test substance | Dose (mg/kg) | Volume (mL/kg) | Regimen | Sacrifice (wks) |
|---|---|---|---|---|---|---|---|
| 1 | 8 | STAM | Vehicle | — | 10 | PO, QD, 6-9 wks | 9 |
| 2 | 8 | STAM | Compound A | 10 | 10 | PO, QD, 6-9 wks | 9 |
| 3 | 8 | STAM | Compound A | 20 | 10 | PO, QD, 6-9 wks | 9 |
| 4 | 8 | STAM | Compound A | 40 | 10 | PO, QD, 6-9 wks | 9 |
| 5 | 8 | STAM | Compound B | 40 | 10 | PO, QD, 6-9 wks | 9 |
| 6 | 8 | STAM | Telmisartan | 10 | 10 | PO, QD, 6-9 wks | 9 |

Animal Monitoring and Sacrifice

The viability, clinical signs and behavior were monitored daily. Body weight was recorded before the treatment. Mice were observed for significant clinical signs of toxicity, moribundity and mortality approximately 60 minutes after each administration. The animals were sacrificed at 9 weeks of age by exsanguination through direct cardiac puncture under isoflurane anesthesia (Pfizer Inc.).

C. Results

1. Body Weight Changes and General Condition

Mean body weight of the Telmisartan group was significantly lower than that of the Vehicle group from Day 9 to Day 21. There were no significant changes in mean body weight at any day during the treatment period between the Vehicle group and the other treatment groups. There were no dead animals in all groups during the treatment period. In the present study, none of the animals showed deterioration in general condition.

2. Body Weight on the Day of Sacrifice and Liver Weight 2.1. Body Weight on the Day of Sacrifice (Table 5)

The Telmisartan group showed a significant decrease in mean body weight on the day of sacrifice compared with the Vehicle group. There were no significant differences in mean body weight on the day of sacrifice between the Vehicle group and the other treatment groups.

2.2. Liver Weight and Liver-to-Body Weight Ratio (Table 5)

The Telmisartan group showed a significant decrease in mean liver weight compared with the Vehicle group. The Compound A low group showed a significant increase in mean liver weight compared with the Vehicle group. Mean liver weight in the Compound A high and Compound B groups tended to increase compared with the Vehicle group. There was no significant difference in mean liver weight between the Vehicle group and the Compound A middle group.

Mean liver-to-body weight ratio in the Telmisartan group tended to decrease compared with the Vehicle group. Mean liver-to-body weight ratio in the Compound A low, middle and high, and Compound B groups tended to increase compared with the Vehicle group.

TABLE 5

Body weight and liver weigh

| Parameter (mean ± SD) | Vehicle (n = 8) | Compound A low (n = 8) | Compound A middle (n = 8) | Compound A high (n = 8) | Compound B (n = 8) | Telmisartan (n = 8) |
|---|---|---|---|---|---|---|
| Body weight (g) | 20.2 ± 1.5 | 20.1 ± 1.8 | 19.7 ± 1.4 | 19.7 ± 1.8 | 20.0 ± 1.8 | 17.7 ± 1.4 |
| Liver weight (mg) | 1428 ± 177 | 1662 ± 254 | 1500 ± 77 | 1654 ± 145 | 1606 ± 227 | 1115 ± 78 |
| Liver-to-body weight ratio (%) | 7.1 ± 0.9 | 8.4 ± 1.8 | 7.6 ± 0.4 | 8.5 ± 1.1 | 8.1 ± 1.1 | 6.5 ± 0.4 |

Figure 3:
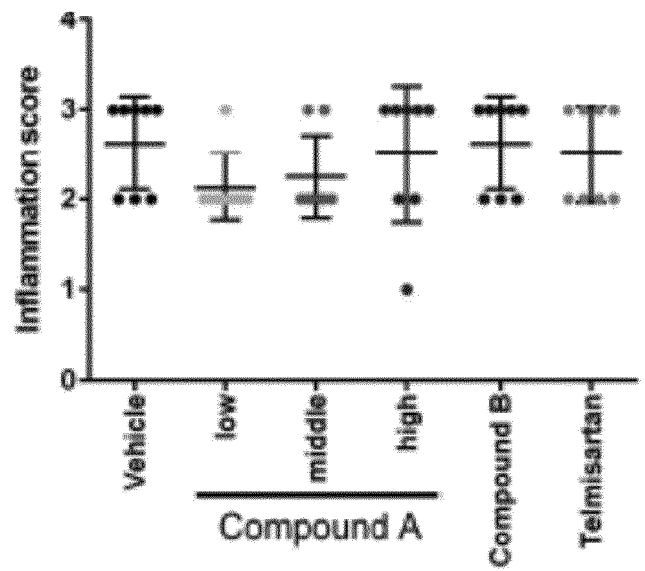
FIG. 3 depicts the Inflammation Score in STAM Model of Non-alcoholic Steatohepatitis (NASH study) performed on ABX464 and its glucuronide metabolite (example 2).

3. Biochemistry 3.1. Plasma ALT (FIG. 3.1 and Table 6)

The Compound A high group showed a significant increase in plasma ALT level compared with the Vehicle group. Plasma ALT level in the Compound A low and middle, and Compound B groups tended to increase compared with the Vehicle group. There was no significant difference in plasma ALT level between the Vehicle group and the Telmisartan group.

3.2. Liver Triglyceride (FIG. 3.2 and Table 2)

Liver triglyceride content in the Telmisartan group tended to decrease compared with the Vehicle group. Liver triglyceride content in the Compound B group tended to increase compared with the Vehicle group. There were no significant differences in liver triglyceride content between the Vehicle group and the other treatment groups.

TABLE 6

Biochemistry

| Parameter (mean ± SD) | Vehicle (n = 8) | Compound A low (n = 8) | Compound A middle (n = 8) | Compound A high (n = 8) | Compound B (n = 8) | Telmisartan (n = 8) |
|---|---|---|---|---|---|---|
| Plasma ALT (U/L) | 55 ± 16 | 75 ± 31 | 91 ± 15 | 133 ± 100 | 72 ± 24 | 56 ± 14 |
| Liver triglyceride (mg/g liver) | 55.3 ± 23.5 | 64.9 ± 27.6 | 63.1 ± 21.2 | 66.6 ± 25.6 | 82.9 ± 32.6 | 41.5 ± 16.9 |

4. Histological Analyses
4.1. HE staining and NAFLD Activity score (Table 7 and FIGS. 1, 2, 3 and 4)

Figure 2:
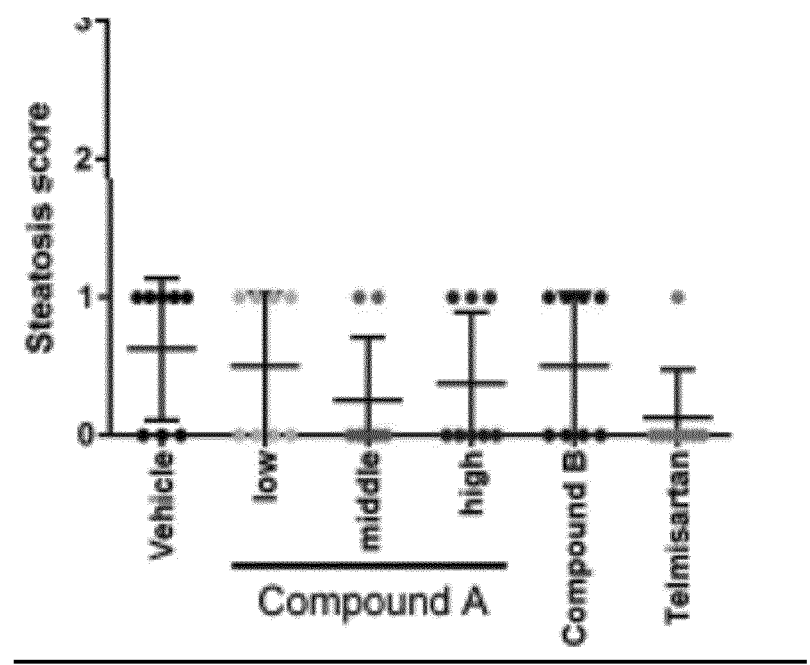
FIG. 2 depicts the Steatosis score in STAM Model of Non-alcoholic Steatohepatitis (NASH study) performed on ABX464 and its glucuronide metabolite (example 2).
Figure 4:
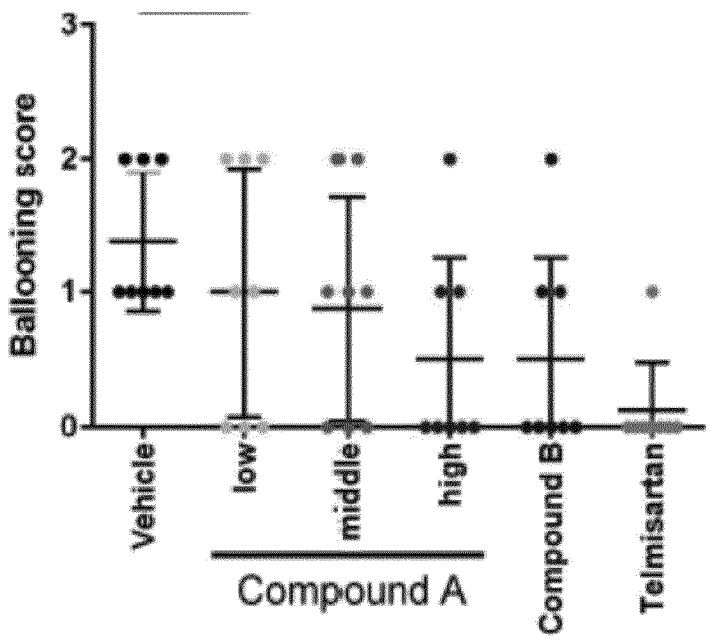
FIG. 4 depicts the Ballooning Score in STAM Model of Non-alcoholic Steatohepatitis (NASH study) performed on ABX464 and its glucuronide metabolite (example 2).

Representative photomicrographs of HE-stained liver sections were analyzed. FIG. 1 represents the NAFLD Activity Score, FIG. 2 represents the Steatosis score, FIG. 3 represents the Inflammation Score and FIG. 4 represents the Ballooning Score.

Liver sections from the Vehicle group exhibited micro- and macrovesicular fat deposition, hepatocellular ballooning and inflammatory cell infiltration. The Telmisartan group showed a significant decrease in NAS compared with the Vehicle group. NAS in the Compound A low, middle and high, and Compound B groups tended to decrease compared with the Vehicle group.

TABLE 7

NAFLD Activity score

| | | Steatosis | | | | Lobular inflammation | | | | Hepatocyte ballooning | | | NAFLD (mean ± SD) |
|---|---|---|---|---|---|---|---|---|---|---|---|---|---|
| Group | n | 0 | 1 | 2 | 3 | 0 | 1 | 2 | 3 | 0 | 1 | 2 | |
| vehicle | 8 | 3 | 5 | — | — | — | — | 3 | 5 | — | 5 | 3 | 4.6 ± 0.7 |
| Compound A low | 8 | 4 | 4 | — | — | — | — | 7 | 1 | 3 | 2 | 3 | 3.6 ± 1.1 |
| Compound A middle | 8 | 6 | 2 | — | — | — | — | 6 | 2 | 3 | 3 | 2 | 3.4 ± 1.2 |
| Compound A high | 8 | 5 | 3 | — | — | — | 1 | 2 | 5 | 5 | 2 | 1 | 3.4 ± 1.3 |
| Compound B | 8 | 4 | 4 | — | — | — | — | 3 | 5 | 5 | 2 | 1 | 3.6 ± 1.2 |
| Telmisartan | 8 | 7 | 1 | — | — | — | — | 4 | 4 | 7 | 1 | — | 2.8 ± 0.7 |

Definition of NAS Components

| Item | Score | Extent |
|---|---|---|
| Steatosis | 0 | <5% |
| | 1 | 5-33% |
| | 2 | >33-66% |
| | 3 | >66% |
| Lobular inflammation | 0 | No foci |
| | 1 | <2 foci/200× |
| | 2 | 2-4 foci/200× |
| | 3 | >4 foci/200× |
| Hepatocyte Ballooning | 0 | None |
| | 1 | Few balloon cells |
| | 2 | Many cells/prominent ballooning |

4.2. Sirius Red Staining and the Fibrosis Area (Table 8 and FIG. 5)

Figure 5:
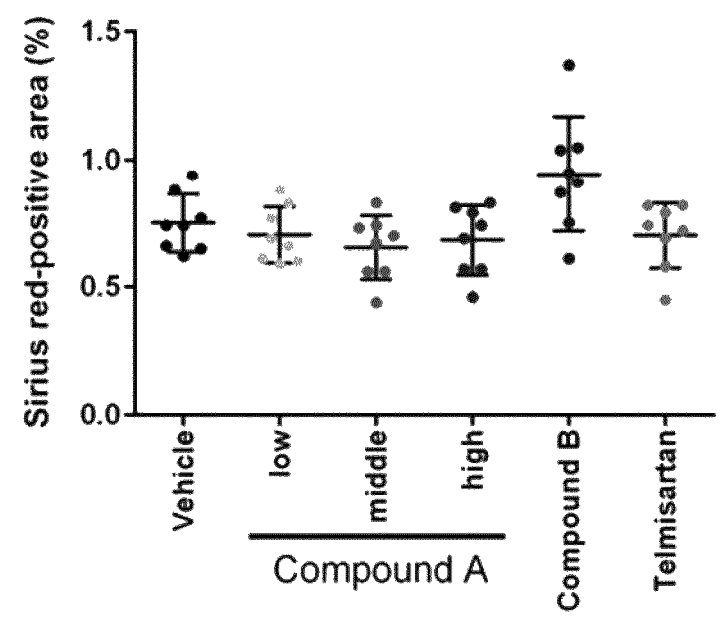
FIG. 5 depicts the Fibrosis area in histological analysis in STAM Model of Non-alcoholic Steatohepatitis (NASH study) performed on ABX464 and its glucuronide metabolite (example 2).

Representative photomicrographs of Sirius red-stained liver sections were analyzed. FIG. 5 represents the Fibrosis area.

Liver sections from the Vehicle group showed increased collagen deposition in the pericentral region of liver lobule. The fibrosis area (Sirius red-positive area) in the Compound A middle group tended to decrease compared with the Vehicle group. The fibrosis area in the Compound B group tended to increase compared with the Vehicle group. There were no significant differences in the fibrosis area between the Vehicle group and the other treatment groups.

TABLE 8

Fibrosis area

| Parameter (mean ± SD) | Vehicle (n = 8) | Compound A low (n = 8) | Compound A middle (n = 8) | Compound A high (n = 8) | Compound B (n = 8) | Telmisartan (n = 8) |
|---|---|---|---|---|---|---|
| Sirius red-positive area (%) | 0.75 ± 0.11 | 0.70 ± 0.11 | 0.65 ± 0.13 | 0.68 ± 0.14 | 0.94 ± 0.23 | 0.70 ± 0.13 |

4.3 Alpha-SMA Immunostaining and a-SMA-Positive Area

Alpha-SMA immunostaining of liver sections from the Vehicle group demonstrated accumulation of a-SMA-positive cells predominantly in zone 3. Alpha-SMA-positive area in the Compound A high and Telmisartan groups tended to decrease compared with the Vehicle group. (Table 9 herein after)

4.4 F4/80 Immunostaining

F4/80 immunostaining of liver sections from the Vehicle group demonstrated accumulation of F4/80-positive cells predominantly in zone 3.

Compound A high group showed significant decrease in F4/80-positive area compared with the Vehicle group. F4/80-positive area in the Compound A middle and Compound B groups tended to decrease compared with the Vehicle group. (Table 9)

TABLE 9

| Parameter (mean ± SD) | Vehicle (n = 8) | Compound A low (n = 8) | Compound A middle (n = 8) | Compound A high (n = 8=) | Compound B (n = 8) | Telmisartan (n = 8) |
|---|---|---|---|---|---|---|
| Alpha-SMA-positive area (%) | 1.31 ± 0.63 | 1.39 ± 1.25 | 0.91 ± 0.55 | 0.85 ± 0.41 | 1.17 ± 0.79 | 0.83 ± 0.26 |
| F4/80-positive area (%) | 2.76 ± 1.15 | 2.22 ± 0.46 | 1.88 ± 0.62 | 1.53 ± 0.77 | 1.90 ± 0.89 | 3.03 ± 0.95 |

Conclusion

Telmisartan

Treatment with Telmisartan showed a significant decrease in NAS compared with the Vehicle group, indicating the drug successfully worked as a positive control in the present study. Treatment with Telmisartan showed a decreasing trend in liver triglyceride content compared with the Vehicle group.

Compound A

Treatment with Compound A at a low dose showed a decreasing trend in NAS compared with the Vehicle group. Treatment with Compound A at a low dose showed an increasing trend in plasma ALT level compared with the Vehicle group.

Treatment with Compound A at a middle dose showed decreasing trends in NAS and the fibrosis area compared with the Vehicle group. Treatment with Compound A at a middle dose showed an increasing trend in plasma ALT level compared with the Vehicle group. Treatment with Compound A at a high dose showed a significant increase in plasma ALT level compared with the Vehicle group. Treatment with Compound A at a high dose showed a decreasing trend in NAS compared with the Vehicle group.

Compound B

Treatment with Compound B showed a decreasing trend in NAS compared with the Vehicle group. Treatment with Compound B showed increasing trends in plasma ALT level, liver triglyceride content and the fibrosis area compared with the Vehicle group.

In the present study, Compound A and B showed decreasing trends in NAS compared with the Vehicle group. In addition, Compound A showed a decreasing trend in the pathological deposition of collagen in the liver as demonstrated by Sirius red staining. Taken together, Compound A showed potential anti-NAS and anti-fibrosis effects and Compound B showed potential anti-NAS effect in this NASH model.

Example 3: In Vivo Efficacy Study of Compounds in the Rat Sugen Hypoxia Model of Pulmonary Arterial Hypertension (PAH)

Experimental Procedures

Study Design

Induction of PAH

The animals are randomized among treatment groups based on their body weight and the results of transthoracic echocardiography (at Day 21) by the Study Director. Animals within the same treatment group are pair-housed.

Animals from Groups 2 to 5 (see Table 10) receive a single subcutaneous injection of sugen (20 mg/kg in 2 mL/kg volume) solution (10 mg/mL) on Day 0 and returned to their cages. Animals from Group 1 receive one subcutaneous injection of DMSO at 2 mL/kg (vehicle for sugen) on Day 0 and returned to their respective cages.

Groups 2-5 are placed in cages for which the controlled air is adjusted to receive a $FiO_2$ equivalent to 0.10 (10%) using a mixture of nitrogen and ambient air controlled by the ventilated cage system. They are kept under these hypoxic conditions for 21 days. While in hypoxia, cages are cleaned and changed once a week, exposing the animals to ambient oxygen levels for less than 10 minutes. They are exposed to ambient oxygen levels from Day 22 to Day 56. Group 1 animals remain in cages exposed to ambient oxygen (normoxic) levels for 56 days. The animals are observed on a daily basis for any changes in their behaviour and general health status.

Treatment

Treatment with the compound A, sildenafil or vehicle is administered as of Day 22 (Groups 2-5) as scheduled and described in Table 10. The Groups 2-4 receives a single dose per day. The reference group 5 receives sildenafil twice a day. Food and water are given ad libitum. Daily observation of the behaviour and general health status of the animals is done. Weekly body weight is taken.

Echocardiogram

An echocardiogram monitoring of the progression of the disease is carried out on Day 0, Day 21 and on surgery day (Day 56) for all the animals.

Blood Sampling

Venous blood (0.5 ml, anticoagulated with EDTA) is sampled from all animals (including the normoxic controls) on day 0, just after administration of the first dose on Day 22 and 56. EDTA-anticoagulated whole blood is centrifuged to yield plasma, plasma decanted into clean tubes labeled at minimum with the animal number, group ID, and time point, and stored frozen at −80° C. until transfer to the Sponsor.

TABLE 10

Treatment Group Assignment and Treatment Information

| Group # | Group Description | Total Daily Treatment Dose | Route of Administration | Treatment Starting Day | Surgery Day | Group Size n |
|---|---|---|---|---|---|---|
| 1a | Male Normoxic Control | n/a | n/a | n/a | Day 56 | 5 |
| 1b | Female Normoxic Control | n/a | n/a | n/a | Day 56 | 5 |
| 2a | Male SuHx + vehicle | n/a | Gavage (qd) | Day 22 | Day 56 | 10* |
| 2b | Female SuHx + vehicle | n/a | Gavage (qd) | Day 22 | Day 56 | 10* |
| 3a | Male SuHx + Low Dose compound A#1 | 70 mg/kg | Gavage (qd) | Day 22 | Day 56 | 10* |
| 3b | Female SuHx + Low Dose compound A#1 | 70 mg/kg | Gavage (qd) | Day 22 | Day 56 | 10* |
| 4a | Male SuHx + High Dose compound A#2 | 120 mg/kg | Gavage (qd) | Day 22 | Day 56 | 10* |
| 4b | Female SuHx + High Dose compound A#2 | 120 mg/kg | Gavage (qd) | Day 22 | Day 56 | 10* |
| 5a | Male SuHx + Sildenafil | 50 mg/kg | Gavage (bid) | Day 22 | Day 56 | 10* |
| 5b | Female SuHx + Sildenafil | 50 mg/kg | Gavage (bid) | Day 22 | Day 56 | 10* |

*To have a group of n = 10, 12 animals is started to compensate for the mortality rate which is about 10-20% in this model.

Surgical Instrumentation and Measurement of Hemodynamic and Functional Parameters in Efficacy Study Animals 1. On the selected day of surgery, rats are anaesthetized with a mixture of 2 to 2.5% isoflurane USP (Abbot Laboratories, Montreal, Canada) in oxygen, and placed on a heating pad to maintain body temperature.
2. Rats are tracheotomized and immediately ventilated by means of a positive-pressure rodent respirator set at ≈10 ml/kg body weight at a frequency of 65-70 strokes/min.
3. Lead II ECG contact electrodes is placed on the rat to continuously monitor the ECG during the surgical procedure.
4. A cannula connected to a pressure transducer is inserted into the left femoral artery to measure the arterial blood pressure.
5. A cannula connected to a pressure transducer is inserted into the right atria through the right jugular vein to measure the right atria pressure.
6. The heart is exposed through a sternotomy and a 20GA 1.16 in Insyte is introduced into the right ventricle and rapidly hooked up to a saline filled PE-50 catheter connected to a transducer.
7. Following a few seconds of right ventricular pressure recording, the Insyte is further advanced into the pulmonary artery to allow PAP recording for an additional 60 seconds.
8. Hemodynamic parameters are recorded continuously for the duration of the procedure or until loss of PAP signal.
9. Following hemodynamic monitoring, chest cavity is further opened to expose the lung. The muscle over the trachea is dissected away to remove the lungs and heart. Harvested tissue is rinsed with PBS to remove any excess of blood before to be weighed.
10. For the histology and casting of the lungs, the process is as follows; 1) eight (8) rats per group is reserved to assess the histology of the left lung and is therefore be treated as described in point 12 of this section 8.2; 2) Two (2) rats per group serve to enable quantitative characterization of the three-dimensional vascular structure of the left lung and therefore is treated as described in section 8.3 for casting of the left lung.
11. For histology, the left lobe is inflated using a 10 mL syringe filled with fixative (10% NBF) with attached blunt tip needle (23 g). Needle tip is inserted into the trachea, held in place with tied suture while another syringe is tied to the pulmonary artery. The lung is inflated gently at physiological pressure (20-25 mmHg) until all lobes are fully, uniformly, and consistently expanded (not allowing fixative to ooze through lung surface). This provides optimal vascular and airway expansion without causing excessive tissue disruption. The needle is then removed, suture around trachea tied, and immersed in 10% NBF at a 1:20 tissue to fixative ratio. The tissues are kept in formalin for 24-48 hrs. They are then cut in three sections (upper, middle and lower). Sections are sent to the Institute for Research in Immunology and Cancer (IRIC) in Montreal (Quebec, Canada) to be embedded, sliced and stained with either Hematoxylin and Eosin (H&E) or von Willebrand Factor (VWF) for endothelial cell staining.
12. As part of the Fulton index, the heart is dissected to separate the right ventricle from the left ventricle with septum, and then weighed separately.

Pulmonary Arterial Casting Procedure

1. Following hemodynamic parameters recording, two out of the 10 rats have their lungs and heart harvested and process for the pulmonary arterial casting of the left lung.
2. A polyethylene (PE190) tube cut at a length of 40 cm, with one end connected to an 18-G needle and the other blunted with heat is used as a catheter into the right ventricle (RV). The catheter is advanced to the level of the main pulmonary artery (MPA), where it is secured in place. For casting of the right lungs, the catheter is advanced in the pulmonary artery (PA) of the right lung, where it is secured in place to avoid perfusion of the left lung.

3. The blood is flushed out of the PAs by pumping 2 ml of diluted heparin sodium (5 units/ml) (APP Pharmaceuticals, Inc., Schaumburg, IL, USA) using a continuous syringe pump set at 2 ml/min. A small incision is made in the left atrial appendage of the left ventricle to allow the solution to flow out the pulmonary artery circulation.
4. To ensure uniform filling especially in the lower lung segments, the lung is held in an upright position.
5. The silicone polymer casting compound, MV-yellow Microfil with a viscosity of 25 centipoise (cP; 0.01 gram per centimeter-second), is mixed with medium-viscosity (MV) diluent in a 5:4 (diluent:compound) volume ratio and added to 5% (by volume) curing agent. This freshly mixed silicone polymer casting material is then pumped through the catheter at 2 ml/min until the polymer reached the RV. The flow rate is reduced as the polymer entered the pulmonary circulation to 0.05 ml/min.
6. The pump is stopped when the polymer is uniformly visible on the lung surface. The PA irrigating the left lung is ligated before being excised from the heart-lung bloc.
7. The left lung with its PA ligated is then transferred in a small container and store at 4° C. for 24 hours to allow complete polymerization of the silicone polymer. In the case of the right lung casting, the right PA is ligated.
8. Once polymerized, 10% formalin is added to the container to submerge the left lung (or lobes of the right lung) with formalin and store at 4° C. for an additional 48 hours.
9. The left lung (or lobes of the right lung) is then shipped to the department of engineering of the University of Sherbrooke (Quebec, Canada) for the micro-CT imaging using the Skyscan from Bruker (Manning Park, MA, USA). Images are then transferred to Fluidda inc. for analysis.

Results:

| Mean pulmonary pressure in female | | |
| --- | --- | --- |
| Treatment | Mean Pulmonary Pressure (mmHg) | SEM |
| Normoxic Control | 14.7 | 0.60 |
| SuHx + Vehicle | 33.5 | 3.42 |
| SuHx + Compound A, 70 mg/kg QD | 24.1 | 3.35 |
| SuHx + compound A, 120 mg/kg QD | 34.4 | 4.22 |
| SuHx + Sildenafil, 50 mg/kg BID | 22.5 | 1.85 |

| Mean pulmonary pressure in male | | |
| --- | --- | --- |
| Treatment | Mean Pulmonary Pressure (mmHg) | SEM |
| Normoxic Control | 15.8 | 0.73 |
| SuHx + Vehicle | 41.7 | 3.29 |
| SuHx + compound A, 70 mg/kg QD | 26.8 | 2.87 |
| SuHx + compound A, 120 mg/kg QD | 33.6 | 6.71 |
| SuHx + Sildenafil, 50 mg/kg BID | 30.1 | 3.04 |

As a conclusion, treatment of rat with compound A in the Sugen hypoxia model show a tendency to decrease mean pulmonary arterial pressure at 70 mg/kg.

Example 4: In Vivo Efficacy Study of Compounds in the Rat Monocrotaline Model of Pulmonary Arterial Hypertension Experimental Systems
Acquisition System
A networked personal computer running Microsoft Windows XP Professional 2007 is used for data acquisition. The acquisition software is AxoScope10.2 using the interface Digidata by Axon Instrument. AxoScope 10.2 has been fully validated in the connected context in which it is used.
Analysis System
The analysis software is Clampfit 10.2.0.14 by Axon Instruments, installed on networked personal computers running Microsoft Windows XP Professional 2016. Clampfit 10.2.0.14 has been fully validated in the connected context in which it is used. The analysis software for graphs is Microsoft Office Excel 2016 installed on networked personal computers running Microsoft Windows 10 Famille.
Compiling the Experimental Data
1. The experimental trace to be analyzed is opened in Clampfit.
2. Right atria pressure is recorded for 1 minute
3. PAP recorded continuously for at least 1 minute or until loss of signal, is used to extract the mean, diastolic, and systolic pulmonary pressure.
4. The systemic arterial pressure (SAP) recorded continuously is used to extract the mean, diastolic and systolic arterial pressure.
5. At the end of the hemodynamic parameters recording, the right and left ventricle including the septum and the lung lobes is excised to determine wet weights.
6. Each parameter is compiled for each group and presented in bar graphs with appropriate statistical analysis.

| | |
| --- | --- |
| 1- | Mean Arterial Systemic Pressure |
| 2- | Mean Arterial Pulmonary Pressure |
| 3- | Diastolic Pulmonary Pressure |
| 4- | Systolic Pulmonary Pressure |
| 5- | Systolic Right Ventricular Pressure |
| 6- | Saturation ($SO_2$) |
| 7- | Weight Gain |
| 8- | Lung Weight |
| 9- | Fulton's Index |
| 10- | Heart Rate |
| 11- | Pulse Pressure |
| 12- | Right Atria Pressure |

Experimental Procedure:
Preparation of Monocrotaline Solution
The appropriate amount of monocrotaline is weighed and ⅓ of the correct volume of 1.0N HCl is added and mixed to ensure monocrotaline solubilisation. The solution is then neutralized with ⅓ of the correct volume of 1.0 N NaOH. The pH of the solution is checked with a pH indicator paper/strip or an electronic pH meter and adjusted to neutral as necessary; the final volume is completed with water for injection to obtain a solution of 20 mg/mL. The monocrotaline solution is injected subcutaneously, over the shoulders, into the loose skin over the neck, to each rat at 3 mL/kg of body weight (dose is 60 mg/kg).
Preparation of Compound a Solution
Compound A was administered as a suspension in the vehicle. To reach the required concentrations, compound A was grounded to a fine powder, using a mortar and pestle, and then mixed with 20% (final volume) of vehicle A1 until a suspension was achieved. 80% of vehicle A2 was then added to the suspension under magnetic stirring.
Vehicle A1: 0.5% (w/v) Carboxymethylcellulose (CMC) 400-800 centipoises in water for injection+2.5% (w/v) Tween 80
Vehicle A2: 0.5% (w/v) Carboxymethylcellulose (CMC) 400-800 centipoises in water for injection
Vehicle for dosing: 20% vehicle A1 with 80% vehicle A2

The control and compound A dose formulations were stirred at least 15 minutes before administration and maintained under continuous magnetic stirring throughout the dosing procedure.

TABLE 11

Concentration solution and administration volume of compound A

| Treatment Dose | Dosing Solution Concentration | Dosing volume |
|---|---|---|
| Low dose #70 mg/kg compound A | 14 mg/ml | 5 ml/kg/day |
| High dose #120 mg/kg compound A | 24 mg/ml | 5 ml/kg/day |

Preparation of Sildenafil

The appropriate amount of Sildenafil is weighed and appropriate volume of distilled water is added to obtain suspension at 5 mg/mL. The suspension is mixed with a stir bar for 30-60 minutes until a homogenous suspension is achieved. Care is taken to maintain a uniform suspension (stirring continuously) whilst doses are being drawn up into gavage syringes. One gavage syringe is filled at a time and administered before filling the next syringe. The solutions are stored refrigerated at 2 to 8° C. and protected from light. The expiration date is set at 7 days after preparation.

TABLE 12

Concentration solution and administration volume of Sildenafil

| Treatment Dose | Dosing Solution Concentration | Dosing volume |
|---|---|---|
| 50 mg/kg bid | 5 mg/mL | 10 mL/kg |

Experimental Procedures
Study Design
Induction of PAH

The animals is randomized among treatment groups based on their body weight and the results of transthoracic echocardiography (at Day 7) by the Study Director. Animals within the same treatment group is pair-housed.

Animals from Groups 2 to 5 (see Table 13) receive a single subcutaneous injection of monocrotaline (60 mg/kg) solution on Day 0 and returned to their cages. Animals from Group 1 receive one subcutaneous injection vehicle for MCT on Day 0 and returned to their respective cages.
Treatment Treatment with the compound A, sildenafil or vehicle is administered as of Day 7 (Groups 2-5) as scheduled and described in Table 13. The Groups 2-4 receive a single dose per day. The reference group 5 receives sildenafil twice a day. Food and water are given ad libitum. Daily observation of the behaviour and general health status of the animals is done. Weekly body weight is taken.
Echocardiogram An echocardiogram monitoring of the progression of the disease is carried out on Day 0, Day 7 and on surgery day (Day 28) for all the animals.

Blood Sampling

Venous blood (0.5 ml, anticoagulated with EDTA) is sampled from all animals (including the normoxic controls) on day 0, just after administration of the first dose on Day 7. On the day of terminal surgery, Day 28, after the hemodynamic measurement, cardiac puncture is performed on rats to collect 3 ml of blood. EDTA-anticoagulated whole blood is centrifuged to yield plasma, plasma decanted into clean tubes labeled at minimum with the animal number, group TD, and time point, and stored frozen at −80° C. until transfer to the Sponsor.

TABLE 13

Treatment Group Assignment and Treatment Information

| Group # | Group Description | Total Daily Treatment Dose | Route of Administration | Treatment Starting Day | Surgery Day | Group Size n |
|---|---|---|---|---|---|---|
| 1a | Male Normoxic Control | n/a | n/a | n/a | Day 28 | 5 |
| 1b | Female Normoxic Control | n/a | n/a | n/a | Day 28 | 5 |
| 2a | Male MCT + vehicle | n/a | Gavage (qd) | Day 7 | Day 28 | 10* |
| 2b | Female MCT + vehicle | n/a | Gavage (qd) | Day 7 | Day 28 | 10* |
| 3a | Male MCT +, Low Dose compound A#1 | 70 mg/kg | Gavage (qd) | Day 7 | Day 28 | 10* |
| 3b | Female MCT +, Low Dose compound A#1 | 70 mg/kg | Gavage (qd) | Day 7 | Day 28 | 10* |
| 4a | Male MCT +, High Dose compound A#2 | 120 mg/kg | Gavage (qd) | Day 7 | Day 28 | 10* |
| 4b | Female MCT +, High Dose compound A #2 | 120 mg/kg | Gavage (qd) | Day 7 | Day 28 | 10* |
| 5a | Male MCT + Sildenafil | 50 mg/kg | Gavage (bid) | Day 7 | Day 28 | 10* |
| 5b | Female MCT + Sildenafil | 50 mg/kg | Gavage (bid) | Day 7 | Day 28 | 10* |

*To have a group of n = 10, 12 animals are started to compensate for the mortality rate which is about 10-20% in this model.

Surgical Instrumentation and Measurement of Hemodynamic and Functional Parameters in Efficacy Study Animals
1. On the selected day of surgery, rats are anaesthetized with a mixture of 2 to 2.5% isoflurane USP (Abbot Laboratories, Montreal, Canada) in oxygen, and placed on a heating pad to maintain body temperature.
2. Rats are tracheotomized and immediately ventilated by means of a positive-pressure rodent respirator set at ≈10 ml/kg bodyweight at a frequency of 65-70 strokes/min.
3. Lead II ECG contact electrodes is placed on the rat to continuously monitor the ECG during the surgical procedure.
4. A cannula connected to a pressure transducer is inserted into the left femoral artery to measure the arterial blood pressure.
5. A cannula connected to a pressure transducer is inserted into the right atria through the right jugular vein to measure the right atria pressure.
6. The heart is exposed through a sternotomy and a 20GA 1.16 in Insyte is introduced into the right ventricle and rapidly hooked up to a saline filled PE-50 catheter connected to a transducer.

7. Following a few seconds of right ventricular pressure recording, the Insyte is further advanced into the pulmonary artery to allow PAP recording for an additional 60 seconds.
8. Hemodynamic parameters is recorded continuously for the duration of the procedure or until loss of PAP signal.
9. Following hemodynamic monitoring, chest cavity is further opened to expose the lung. The muscle over the trachea is dissected away to remove the lungs and heart. Harvested tissue is rinsed with PBS to remove any excess of blood before to be weighed.
10. The chest cavity is further opened to expose the lung. The muscle over the trachea is dissected away to remove the lungs and heart. Harvested tissue is rinsed with PBS to remove any excess of blood before to be weighed.
11. For the histology and casting of the lungs, the process is as follows; 1) eight (8) rats per group is reserved to assess the histology of the left lung and is therefore treated as described in point 12 of this section 8.2; 2) Tow (2) rats per group serve to enable quantitative characterization of the three-dimensional vascular structure of the left lung and therefore is treated as described in section 8.3 for casting of the left lung.
12. For histology, the left lobe is inflated using a 10 mL syringe filled with fixative (10% NBF) with attached blunt tip needle (23 g). Needle tip is inserted into the trachea, held in place with tied suture while another syringe is tied to the pulmonary artery. The lung is inflated gently at physiological pressure (20-25 mmHg) until all lobes are fully, uniformly, and consistently expanded (not allowing fixative to ooze through lung surface). This provides optimal vascular and airway expansion without causing excessive tissue disruption. The needle is then removed, suture around trachea tied, and immersed in 10% NBF at a 1:20 tissue to fixative ratio. The tissues is kept in formalin for 24-48 hrs. They are then cut in three sections (upper, middle and lower). Sections is sent to the Institute for Research in Immunology and Cancer (IRIC) in Montreal (Quebec, Canada) to be embedded, sliced and stained with either Hematoxylin and Eosin (H&E) and von Willebrand Factor (VWF) for endothelial cell staining.
13. As part of the Fulton index, the heart is dissected to separate the right ventricle from the left ventricle with septum, and then weighed separately.

Pulmonary Arterial Casting Procedure
1. Following hemodynamic parameters recording, two out of the 10 rats have their lungs and heart harvested and process for the pulmonary arterial casting of the left lung.
2. A polyethylene (PE190) tube cut at a length of 40 cm, with one end connected to an 18-G needle and the other blunted with heat is used as a catheter into the right ventricle (RV). The catheter is advanced to the level of the main pulmonary artery (MPA), where it is secured in place. For casting of the right lungs, the catheter is advanced in the pulmonary artery (PA) of the right lung, where it is secured in place to avoid perfusion of the left lung.
3. The blood is flushed out of the PAs by pumping 2 ml of diluted heparin sodium (5 units/ml) (APP Pharmaceuticals, Inc., Schaumburg, IL, USA) using a continuous syringe pump set at 2 ml/min. A small incision is made in the left atrial appendage of the left ventricle to allow the solution to flow out the pulmonary artery circulation.
4. To ensure uniform filling especially in the lower lung segments, the lung is held in an upright position.
5. The silicone polymer casting compound, MV-yellow Microfil with a viscosity of 25 centipoise (cP; 0.01 gram per centimeter-second), is mixed with medium-viscosity (MV) diluent in a 5:4 (diluent:compound) volume ratio and added to 5% (by volume) curing agent. This freshly mixed silicone polymer casting material is then pumped through the catheter at 2 ml/min until the polymer reached the RV. The flow rate is reduced as the polymer entered the pulmonary circulation to 0.05 ml/min.
6. The pump is stopped when the polymer is uniformly visible on the lung surface. The PA irrigating the left lung is ligated before being excised from the heart-lung bloc.
7. The left lung with its PA ligated is then transferred in a small container and store at 4° C. for 24 hours to allow complete polymerization of the silicone polymer. In the case of the right lung casting, the right PA is ligated.
8. Once polymerized, 10% formalin is added to the container to submerge the left lung (or lobes of the right lung) with formalin and store at 4° C. for an additional 48 hours.
9. The left lung (or lobes of the right lung) is then shipped to the department of engineering of the University of Sherbrooke (Quebec, Canada) for the micro-CT imaging using the Skyscan from Bruker (Manning Park, MA, USA). Images are then be transfer to Fluidda inc. for analysis.

Results:
Mean Pulmonary Pressure:

| | Mean pulmonary pressure in female rat | | | | |
| --- | --- | --- | --- | --- | --- |
| Treatment | Mean Pulmonary Pressure (mmHg) | SEM | p value compared to Control | p value compared to MCT + Vehicle | n |
| Control | 16.4 | 1.28 | n/a | 0.073 | 5 |
| MCT + Vehicle | 23.7 | 2.63 | 0.073 | n/a | 9 |
| MCT + compound A, 70 mg/kg QD | 22.2 | 2.00 | 0.054 | 0.659 | 7 |
| MCT + compound A, 120 mg/kg QD | 16.9 | 1.00 | 0.797 | 0.017 | 11 |
| MCT + Sildenafil, 50 mg/kg BID | 18.9 | 0.96 | 0.158 | 0.081 | 11 |

Conclusion

In the present study, treatment with compound A reduces significantly the pulmonary pressure in female rat where pulmonary hypertension has been induced by monocrotaline but has no effect in male rat.

FURTHER EXEMPLARY EMBODIMENTS

1. A method for treating an inflammatory disease, disorder or condition in a patient in need thereof, wherein the inflammatory disease, disorder or condition is selected from:
   a. an inflammatory disease, disorder, or condition in the pancreas selected from diabetes type-1, diabetes type-2, acute and chronic pancreatitis;
   b. an inflammatory disease, disorder, or condition in the kidney selected from glomerulosclerosis, glomerulonephritis, nephritis, acute kidney injury, Berger's disease, Goodpasture's syndrome, Wegener's granulomatosis and kidney transplant acute or chronic rejection;

c. an inflammatory disease, disorder, or condition in the liver selected from nonalcoholic steatohepatitis (NASH), non-alcoholic fatty liver disease (NAFLD), cholestatic liver disease, sclerosing cholangitis and liver transplant acute or chronic rejection;

d. an inflammatory disease, disorder, or condition in the lung or heart selected from chronic obstructive pulmonary disease (COPD), asthma, pulmonary fibrosis, pulmonary hypertension, sarcoidosis, myocarditis, pericarditis and lung or heart transplant acute or chronic rejection;

e. an inflammatory disease, disorder, or condition in the skin selected from contact dermatitits, atopic dermatitis, psoriasis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, acnea, keloid scar, and other inflammatory or allergic conditions of the skin;

f. an inflammatory disease, disorder, or condition in the vessel/blood selected from Behcet's disease, vasculitis, sepsis, tumor angiogenesis, atherosclerosis, proliferative vascular disease and restenosis;

g. an inflammatory disease, disorder, or condition in the eye selected from conjunctivitis, scleritis, episcleritis, panuveitis, choroiditis, chorioretinitis, neuroretinitis, uveitis, orbital inflammatory disease, and optical neuritis;

h. an inflammatory disease, disorder, or condition in the central or peripheral nervous system selected from non-viral and viral encephalitis and meningitis, depression, neuropathic pain, including chronic pain, traumatic brain injury, including stroke, Alzheimer disease, Parkinson disease, Myelitis, Charcot-Marie-Tooth disease type 1 (including CMT1A and CMT1B), Multiple sclerosis, Amyotrophic lateral sclerosis (ALS), Creutzfeldt-Jakob disease, demyelinating polyneuropathy and peripheral neuropathy;

i. an autoimmune disease, disorder, or condition selected from Lupus, including in the skin and kidney, Guillain-Barre syndrome, Myasthenia gravis, Hashimoto's thyroiditis, idiopathic purpura, aplastic anemia, Graves disease, and Myocarditis;

j. an inflammatory disease, disorder, or condition in the intestine selected from intestinal failure, Ulcerative colitis and Crohn's disease;

k. an inflammatory disease, disorder, or condition in the reproductive system selected from endometriosis, uterine fibroma, prostate dysplasia or growth, and cervix dysplasia; and l. an inflammatory disease, disorder, or condition in the bone and/or joints selected from juvenile idiopathic arthritis, psoriatic arthritis, periodontitis, and hand, foot, ankle, knee, hip, shoulder, elbow or spine arthritis and/or demineralization; comprising a step of administering to the patient a compound of Formula (I):

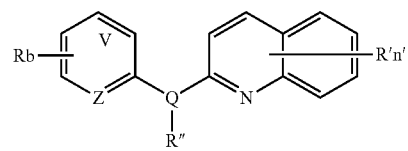

or a pharmaceutically acceptable salt thereof, wherein: Z is C or N; V is C or N;

means an aromatic ring wherein V is C or N, and when V is N, V is ortho, meta or para relative to Z;

each R is independently hydrogen, halogen, —CN, hydroxyl, $(C_1-C_3)$fluoroalkyl, $(C_1-C_3)$fluoroalkoxy, $(C_3-C_6)$ cycloalkyl, —NO$_2$, —NR$_1$R$_2$, $(C_1-C_4)$alkoxy, phenoxy, —NR$_1$—SO$_2$—NR$_1$R$_2$, —NR$_1$—SO$_2$—R$_1$, —NR$_1$—C(=O)—R$_1$, —NR$_1$—C(=O)—NR$_1$R$_2$, —SO$_2$—NR$_1$R$_2$, —SO$_3$H, —O—SO$_2$—OR$_3$, —O—P(=O)—(OR$_3$)(OR$_4$), —O—CH$_2$—COOR$_3$, $(C_1-C_3)$alkyl, said alkyl being optionally mono- or di-substituted by a hydroxyl group or a group of formula (IIa):

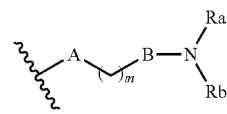

or a group of formula (IIIa):

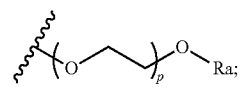

Q is N or O, provided that R" does not exist when Q is O;

each of R$_1$ and R$_2$ is independently hydrogen or $(C_1-C_3)$ alkyl;

each of R$_3$ and R$_4$ is independently hydrogen, Li$^+$, Na$^+$, K$^+$, N$^+$(Ra)$_4$ or benzyl;

n is 1, 2 or 3;

n' is 1, 2 or 3;

each R' is independently hydrogen, $(C_1-C_3)$alkyl, hydroxyl, halogen, —NO$_2$, —NR$_1$R$_2$, morpholinyl, morpholino, N-methylpiperazinyl, $(C_1-C_3)$fluoroalkyl, $(C_1-C_4)$alkoxy, —O—P(=O)—(OR$_3$)(OR$_4$), —CN, a group of formula (Ia):

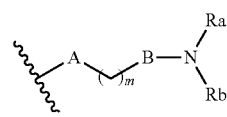

or a group of formula

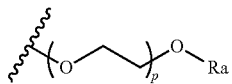
(IIIa)

A is a covalent bond, oxygen, or NH;
B is a covalent bond or NH;
m is 1, 2, 3, 4 or 5;
p is 1, 2 or 3;
each of Ra and Rb is independently hydrogen, $(C_1\text{-}C_5)$alkyl, or $(C_3\text{-}C_6)$cycloalkyl, or Ra and Rb form together with the nitrogen atom to which they are attached a saturated 5- or 6-membered heterocycle, said heterocycle being optionally substituted by one or more Ra, provided that when R' is a group (IIa) or (IIIa), n' may be 2 or 3 only if other R' groups are different from said group (IIa) or (IIIa); and
R" is hydrogen, $(C_1\text{-}C_4)$alkyl, or a group of formula (IIa) as defined herein.

2. The method of embodiment 1, wherein the compound is of formula (Ia):

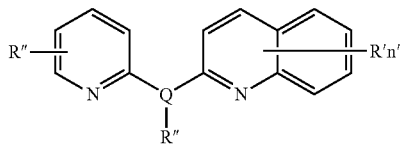
(Ia)

or a pharmaceutically acceptable salt thereof.

3. The method of embodiment 1, wherein the compound is of formula (Ib):

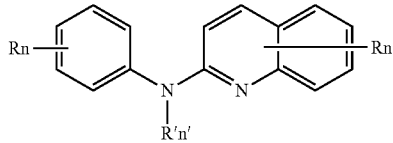
(Ib)

or a pharmaceutically acceptable salt thereof.

4. The method of embodiment 1, wherein the compound is of formula (Ic):

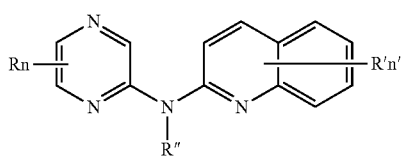
(Ic)

or a pharmaceutically acceptable salt thereof.

5. The method of embodiment 1, wherein the compound is of formula (Ib'):

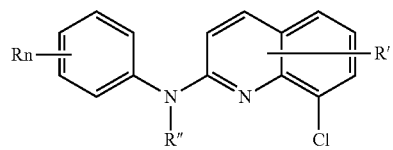
(Ib')

or a pharmaceutically acceptable salt thereof.

6. The method of embodiment 1, wherein the compound is of formula (Id):

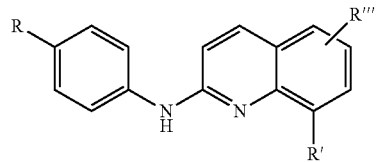

(Id)
or a pharmaceutically acceptable salt thereof.

7. A compound of formula (IV):

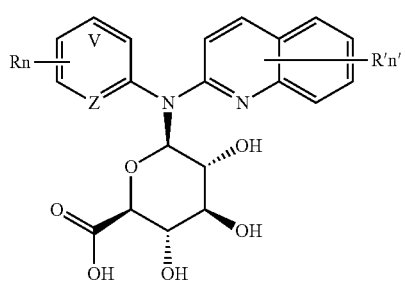
(IV)

or a pharmaceutically acceptable salt thereof, wherein each of variables V, Z, R, R', n, and n' is as described in embodiment 1, provided that the compound is not

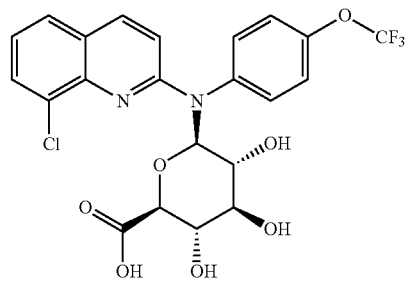 [SMILES: O=C(O)[C@H]1O[C@@H](N(c2ccc(OC(F)(F)F)cc2)c2ccc3cccc(Cl)c3n2)[C@H](O)[C@@H](O)[C@@H]1O]

8. The compound of embodiment 7, wherein the compound is of formula (IVa):

(IVa)
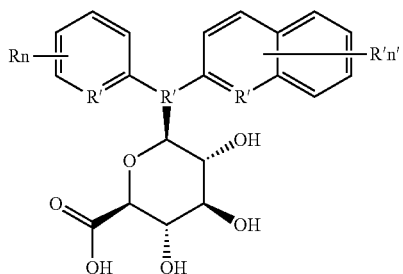

or a pharmaceutically acceptable salt thereof.

9. The compound of embodiment 7, wherein the compound is of formula (IVb):

(IVb)
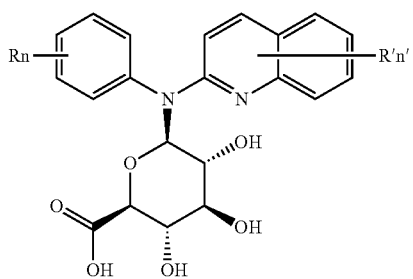

or a pharmaceutically acceptable salt thereof.

10. The compound of embodiment 7, wherein the compound is of formula (IVc):

(IVc)
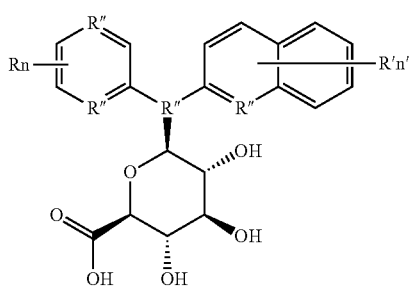

or a pharmaceutically acceptable salt thereof.

11. The compound of embodiment 7, wherein the compound is of formula (IVb'):

(IVb')
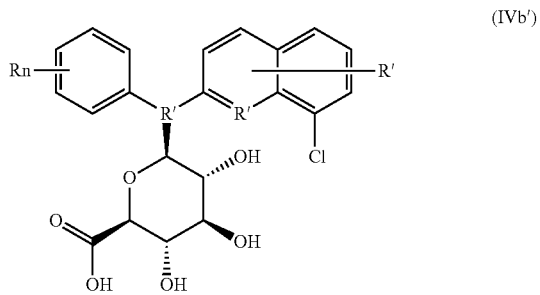

or a pharmaceutically acceptable salt thereof.

12. The compound of embodiment 7, wherein the compound is of formula (IVd):

(IVd)
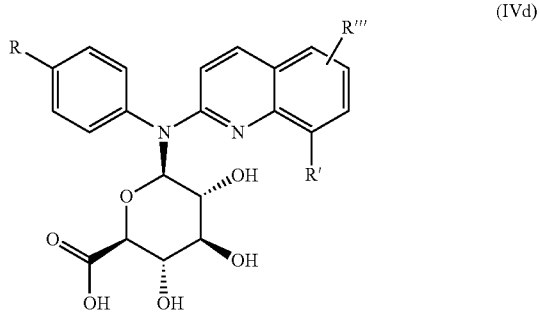

or a pharmaceutically acceptable salt thereof.

13. A pharmaceutical composition comprising a compound of any one of embodiments 7-12, or a pharmaceutically acceptable salt thereof, and a pharmaceutically acceptable carrier, adjuvant, or vehicle.

14. A method for treating an inflammatory disease, disorder or condition comprising administering to a patient in need thereof a compound of any one of embodiments 7-12, or a pharmaceutically acceptable salt thereof, or a pharmaceutical composition of embodiment 13.

15. The method of any one of embodiments 1-6 and 14, wherein the inflammatory disease, disorder or condition is in the pancreas selected from diabetes type-1, diabetes type-2, acute and chronic pancreatitis.

16. The method of any one of embodiments 1-6 and 14, wherein the inflammatory disease, disorder or condition is in the kidney selected from glomerulosclerosis, glomerulonephritis, nephritis, acute kidney injury, Berger's disease, Goodpasture's syndrome, Wegener's granulomatosis and kidney transplant acute or chronic rejection.

17. The method of any one of embodiments 1-6 and 14, wherein the inflammatory disease, disorder or condition is in the liver selected from nonalcoholic steatohepatitis (NASH), non-alcoholic fatty liver disease (NAFLD), cholestatic liver disease, sclerosing cholangitis and liver transplant acute or chronic rejection.

18. The method of any one of embodiments 1-6 and 14, wherein the inflammatory disease, disorder or condition is in the lung or heart selected from chronic obstructive pulmonary disease (COPD), asthma, pulmonary fibrosis, pulmonary hypertension, sarcoidosis, myocarditis, pericarditis and lung or heart transplant acute or chronic rejection.

19. The method of any one of embodiments 1-6 and 14, wherein the inflammatory disease, disorder or condition is in the skin selected from contact dermatitits, atopic dermatitis, psoriasis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, acnea, keloid scar, and other inflammatory or allergic conditions of the skin.

20. The method of any one of embodiments 1-6 and 14, wherein the inflammatory disease, disorder or condition is in the vessel/blood selected from Behcet's disease, vasculitis, sepsis, tumor angiogenesis, atherosclerosis, proliferative vascular disease and restenosis.

21. The method of any one of embodiments 1-6 and 14, wherein the inflammatory disease, disorder or condition is in the eye selected from conjunctivitis, scleritis, episcleritis, panuveitis, choroiditis, chorioretinitis, neuroretinitis, uveitis, orbital inflammatory disease, and optical neuritis.

22. The method of any one of embodiments 1-6 and 14, wherein the inflammatory disease, disorder or condition is in the central or peripheral nervous system selected from non-viral and viral encephalitis and meningitis, depression, neuropathic pain, including chronic pain, traumatic brain injury, including stroke, Alzheimer disease, Parkinson disease, Myelitis, Charcot-Marie-Tooth disease type 1 (including CMT1A and CMT1B), Multiple sclerosis, Amyotrophic lateral sclerosis (ALS), Creutzfeldt-Jakob disease, demyelinating polyneuropathy and peripheral neuropathy.

23. The method of any one of embodiments 1-6 and 14, wherein the inflammatorydisease, disorder or condition is an autoimmune disease, disorder, or condition selected from Lupus, including in the skin and kidney, Guillain-Barre syndrome, Myasthenia gravis, Hashimoto's thyroiditis, idiopathic purpura, aplastic anemia, Graves disease, and Myocarditis.

24. The method of any one of embodiments 1-6 and 14, wherein the inflammatory disease, disorder or condition is in the intestine selected from intestinal failure, Ulcerative colitis and Crohn's disease.

25. The method of any one of embodiments 1-6 and 14, wherein the inflammatory disease, disorder or condition is in the reproductive system selected from endometriosis, uterine fibroma, prostate dysplasia or growth, and cervix dysplasia.

26. The method of any one of embodiments 1-6 and 14, wherein the inflammatory disease, disorder or condition is in the bone and/or joints selected from juvenile idiopathic arthritis, psoriatic arthritis, periodontitis, and hand, foot, ankle, knee, hip, shoulder, elbow or spine arthritis and/or demineralization.

27. The method of any one of embodiments 1-6 and 14-26, further comprising measuring a level of a compound of formula (I), or a pharmaceutically acceptable salt thereof, in a blood, plasma, tissue, saliva, and/or serum sample of the patient.

28. The method of any one of embodiments 1-6 and 14-27, further comprising measuring a level of a compound of formula (IV), or a pharmaceutically acceptable salt thereof, in a blood, plasma, tissue, saliva, and/or serum sample of the patient.

29. The method of any one of embodiments 1-6 and 14-28, further comprising measuring a total level of compounds of formulas (I) and (IV), or pharmaceutically acceptable salts thereof, in a blood, plasma, tissue, saliva, and/or serum sample of the patient.

30. The method of any one of embodiments 1-6 and 14-29, further comprising measuring a presence and/or expression level of miR-124 in a blood and/or tissue sample of the patient, prior to and during the course of the treatment.

31. The method of any one of embodiments 1-6 and 14-30, further comprising selecting a patient by a measured presence and/or expression level of miR-124 in a blood and/or tissue sample of the patient.

32. The method of any one of embodiments 1-6 and 14-31, further comprising using an algorithm that combines miR-124 level and the level of a cytokine or another biomarker, or levels of compounds of formulas (I) or (IV) or pharmaceutically acceptable salts thereof, to monitor severity of a disease, disorder, or condition, and/or to monitor efficacy of a treatment.

33. The method of any one of embodiments 1-6 and 14-31, further comprising using an algorithm that combines miR-124 level and the level of a cytokine or another biomarker, or levels of compounds of formulas (I) or (IV) or pharmaceutically acceptable salts thereof to select patients for a treatment.

34. An algorithm that combines miR-124 level and selected cytokine or another biomarker, or levels of compounds of formulas (I) or (IV) or pharmaceutically acceptable salts thereof to monitor severity of a disease, disorder, or condition, and/or to monitor efficacy of a treatment.

The invention claimed is:

1. A method for treating an inflammatory disease, disorder or condition comprising administering a compound to a patient suffering from the inflammatory disease, disorder or condition, wherein the compound is 8-Chloro-N-(4-(trifluoromethoxy)phenyl)quinolin-2-amine or a pharmaceutically acceptable salt thereof,
wherein the inflammatory disease, disorder or condition being treated by the administration of the compound is selected from the group consisting of:
(a) an inflammatory disease, disorder, or condition in the pancreas selected from diabetes type-1, diabetes type-2, acute and chronic pancreatitis;
(b) an inflammatory disease, disorder, or condition in the kidney selected from glomerulosclerosis, glomerulonephritis, nephritis, acute kidney injury, Berger's disease, Goodpasture's syndrome, Wegener's granulomatosis and kidney transplant acute or chronic rejection;
(c) an inflammatory disease, disorder, or condition in the liver selected from nonalcoholic steatohepatitis (NASH), non-alcoholic fatty liver disease (NAFUD), cholestatic liver disease, sclerosing cholangitis and liver transplant acute or chronic rejection;
(d) an inflammatory disease, disorder, or condition in the lung or heart selected from chronic obstructive pulmonary disease (COPD), pulmonary fibrosis, pulmonary hypertension, sarcoidosis, myocarditis, pericarditis and lung or heart transplant acute or chronic rejection;
(e) an inflammatory disease, disorder, or condition in the skin selected from contact dermatitis, atopic dermatitis, alopecia areata, erythema multiforma, dermatitis herpetiformis, scleroderma, vitiligo, hypersensitivity angiitis, uticaria, bullous pemphigoid, pemphigus vulgaris, pemphigus foliaceus, paraneoplastic pemphigus, epidermolysis bullosa acquisita, acnea and keloid scar;
(f) an inflammatory disease, disorder, or condition in the vessel/blood selected from Behcet's disease, vasculitis, sepsis, tumor angiogenesis, proliferative vascular disease and restenosis;
(g) an inflammatory disease, disorder, or condition in the eye selected from conjunctivitis, scleritis, episcleritis, panuveitis, choroiditis, chorioretinitis, neuroretinitis, uveitis, orbital inflammatory disease, and optical neuritis;
(h) an inflammatory disease, disorder, or condition in the central or peripheral nervous system selected from non-viral and viral encephalitis and meningitis, depression, neuropathic pain, traumatic brain injury, Myelitis, Charcot-Marie-Tooth disease type 1, Amyotrophic lateral sclerosis (ALS), Creutzfeldt-Jakob disease, demyelinating polyneuropathy and peripheral neuropathy;
(i) an autoimmune disease, disorder, or condition selected from Lupus, Guillain-Barre syndrome, Myasthenia gravis, Hashimoto's thyroiditis, idiopathic purpura, aplastic anemia, Graves disease, and Myocarditis;
(k) an inflammatory disease, disorder, or condition in the reproductive system selected from endometriosis, uterine fibroma, prostate dysplasia or growth, and cervix dysplasia; and
(l) an inflammatory disease, disorder, or condition in the bone and/or joints selected from juvenile idiopathic arthritis, psoriatic arthritis, periodontitis, and hand, foot, ankle, knee, hip, shoulder, elbow or spine arthritis and/or demineralization.

2. A method for treating an inflammatory disease, disorder or condition comprising administering to a patient suffering from the inflammatory disease, disorder or condition a compound of formula (IV):

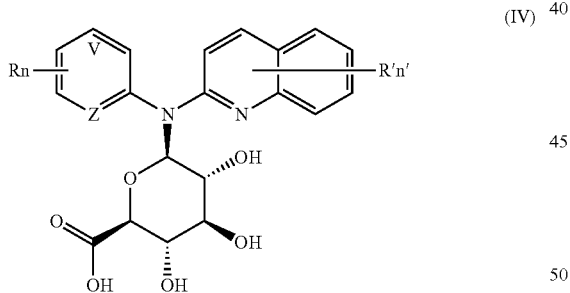

(IV)

or a pharmaceutically acceptable salt thereof, wherein:
Z is C or N;
V is C or N;

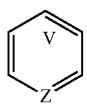

means an aromatic ring, wherein V is C or N, and when V is N, V is ortho, meta or para relative to Z;
each R is independently hydrogen, halogen, —CN, hydroxyl, $(C_1\text{-}C_3)$fluoroalkyl, $(C_1\text{-}C_3)$fluoroalkoxy, $(C_3\text{-}C_6)$cycloalkyl, —$NO_2$, —$NR_1R_2$, $(C_1\text{-}C_4)$ alkoxy, phenoxy, —$NR_1$—$SO_2$—$NR_1R_2$, —$NR_1$—$SO_2$—R1, —$NR_1$—C(=O)—$R_1$, —$NR_1$—C(=O)—$NR_1R_2$, —$SO_2$—$NR_1R_2$, —$SO_3H$, —O—$SO_2$—$OR_3$, —O—P(=O)—$(OR_3)(OR_4)$, —O—$CH_2$—$COOR_3$, $(C_1\text{-}C_3)$alkyl, the alkyl being optionally mono- or di-substituted by a hydroxyl group or a group of formula (IIa):

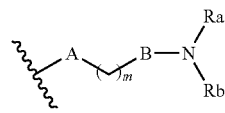

or a group of formula (IIIa):

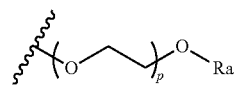

each of $R_1$ and $R_2$ is independently hydrogen or $(C_1\text{-}C_3)$alkyl;
each of $R_3$ and $R_4$ is independently hydrogen, $Li^+$, $Na^+$, $K^+$, $N^+ (Ra)_4$ or benzyl;
n is 1, 2 or 3;
n' is 1, 2 or 3;
each R' is independently hydrogen, $(C_1\text{-}C_3)$alkyl, hydroxyl, halogen, —$NO_2$, —$NR_1R_2$, morpholinyl, morpholino, N-methylpiperazinyl, $(C_1\text{-}C_3)$fluoroalkyl, $(C_1\text{-}C_4)$alkoxy, —O—P(=O)—$(OR_3)(OR_4)$, —CN, a —NH—$SO_2$—$N(CH_3)_2$ group, a group of formula (IIa):

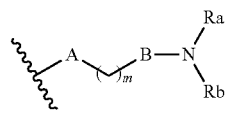

or a group of formula (IIIa):

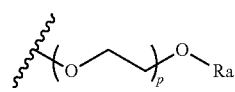

A is a covalent bond, oxygen, or NH;
B is a covalent bond or NH;
m is 1, 2, 3, 4 or 5;
p is 1, 2 or 3;
each of Ra and Rb is independently hydrogen, $(C_1\text{-}C_5)$ alkyl, or $(C_3\text{-}C_6)$cycloalkyl, or Ra and Rb form together with the nitrogen atom to which Ra and Rb are attached a saturated 5- or 6-membered heterocycle, the heterocycle optionally containing a further heteroatom chosen among N, O, S, the heterocycle being optionally substituted by one or more Ra, provided that when R' is a group (IIa) or (IIIa), n' may be 2 or 3 only if other R' groups are different from the group (IIa) or (IIIa); and
R" is hydrogen, $(C_1\text{-}C_4)$alkyl, or a group of formula (IIa) as defined herein, wherein the inflammatory disease, disorder or condition being treated by the administration of the compound of formula (IV) is selected from the group consisting of:

(a) an inflammatory disease, disorder, or condition in the pancreas selected from diabetes type-1, diabetes type-2, acute and chronic pancreatitis;

(b) an inflammatory disease, disorder, or condition in the kidney selected from glomerulosclerosis, glomerulonephritis, nephritis, acute kidney injury, Berger's disease, Goodpasture's syndrome, Wegener's granulomatosis and kidney transplant acute or chronic rejection;

(c) an inflammatory disease, disorder, or condition in the liver selected from nonalcoholic steatohepatitis (NASH), non-alcoholic fatty liver disease (NAFLD), cholestatic liver disease, sclerosing cholangitis and liver transplant acute or chronic rejection;

(d) an inflammatory disease, disorder, or condition in the lung or heart selected from chronic obstructive pulmonary disease (COPD), pulmonary fibrosis, pulmonary hypertension, sarcoidosis, myocarditis, pericarditis and lung or heart transplant acute or chronic rejection;

(e) an inflammatory disease, disorder, or condition in the skin selected from contact dermatitits, atopic dermatitis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, acnea and keloid scar;

(f) an inflammatory disease, disorder, or condition in the vessel/blood selected from Behcet's disease, vasculitis, sepsis, tumor angiogenesis, proliferative vascular disease and restenosis;

(g) an inflammatory disease, disorder, or condition in the eye selected from conjunctivitis, scleritis, episcleritis, panuveitis, choroiditis, chorioretinitis, neuroretinitis, uveitis, orbital inflammatory disease, and optical neuritis;

(h) an inflammatory disease, disorder, or condition in the central or peripheral nervous system selected from non-viral and viral encephalitis and meningitis, depression, neuropathic pain, traumatic brain injury, Myelitis, Charcot-Marie-Tooth disease type 1, Amyotrophic lateral sclerosis (ALS), Creutzfeldt-Jakob disease, demyelinating polyneuropathy and peripheral neuropathy;

(i) an autoimmune disease, disorder, or condition selected from Lupus, Guillain-Barre syndrome, Myasthenia gravis, Hashimoto's thyroiditis, idiopathic purpura, aplastic anemia, Graves disease, and Myocarditis;

(k) an inflammatory disease, disorder, or condition in the reproductive system selected from endometriosis, uterine fibroma, prostate dysplasia or growth, and cervix dysplasia; and (l) an inflammatory disease, disorder, or condition in the bone and/or joints selected from juvenile idiopathic arthritis, psoriatic arthritis, periodontitis, and hand, foot, ankle, knee, hip, shoulder, elbow or spine arthritis and/or demineralization.

3. The method according to claim 2, wherein the compound is of formula (IVb):

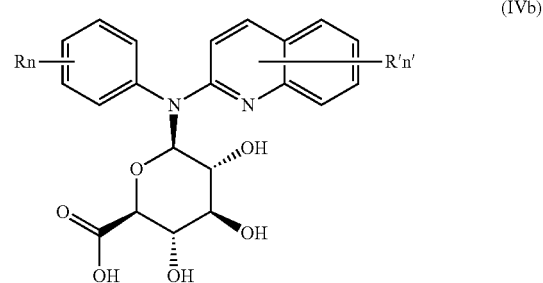

(IVb)

or a pharmaceutically acceptable salt thereof.

4. The method according to claim 2, wherein the compound is of formula (IVb'):

(IVb')

or a pharmaceutically acceptable salt thereof.

5. The method according to claim 2, wherein the compound is or a pharmaceutically acceptable salt thereof.

6. The method according to claim 1, wherein the inflammatory disease, disorder or condition is in the liver and is selected from nonalcoholic steatohepatitis (NASH), non-alcoholic fatty liver disease (NAFLD), cholestatic liver disease, sclerosing cholangitis and liver transplant acute or chronic rejection.

7. The method according to claim 1, wherein the inflammatory disease, disorder or condition is in the lung or heart and is selected from chronic obstructive pulmonary disease (COPD), pulmonary fibrosis, pulmonary hypertension, sarcoidosis, myocarditis, pericarditis and lung or heart transplant acute or chronic rejection.

8. The method according to claim 1, further comprising measuring a level of the 8-Chloro-N-(4-(trifluoromethoxy)phenyl)quinolin-2-amine or the pharmaceutically acceptable salt thereof, in a blood, plasma, tissue, saliva, and/or serum sample of the patient.

9. The method according to claim 1, wherein a presence and/or expression level of miR-124 in a blood and/or tissue sample of the patient is measured prior to and after administering the 8-Chloro-N-(4-(trifluoromethoxy)phenyl)quinolin-2-amine or the pharmaceutically acceptable thereof to the patient.

10. The method according to claim 1, further comprising monitoring a severity of the inflammatory disease, disorder, or condition or monitoring efficacy of the 8-Chloro-N-(4-(trifluoromethoxy)phenyl)quinolin-2-amine or the pharmaceutically acceptable salt thereof in treating the inflammatory, disease, disorder, or condition in the patient, the monitoring including using an algorithm that combines an miR-124 level and the level of a cytokine or another biomarker, or the level of the 8-Chloro-N-(4-(trifluoromethoxy)phenyl)quinolin-2-amine or the pharmaceutically acceptable salt thereof.

11. A method for treating an inflammatory disease, disorder or condition comprising administering to a patient suffering from the inflammatory disease, disorder or condition a compound of Formula (I):

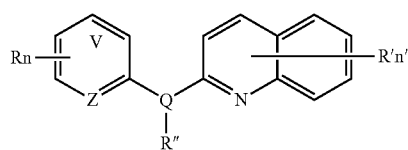

or a metabolite or a pharmaceutically acceptable salt thereof, wherein:

Z is C or N;

V is C or N;

means an aromatic ring, wherein V is C or N, and when V is N, V is ortho, meta or para relative to Z;

each R is independently hydrogen, halogen, —CN, hydroxyl, $(C_1$-$C_3)$fluoroalkyl, $(C_1$-$C_3)$fluoroalkoxy, $(C_3$-$C_6)$cycloalkyl, —$NO_2$, —$NR_1R_2$, $(C_1$-$C_4)$alkoxy, phenoxy, —$NR_1$—$SO_2$—$NR_1R_2$, —$NR_1$—$SO_2$—$R_1$, —$NR_1$—C(=O)—$R_1$, —$NR_1$—C(=O)—$NR_1R_2$, —$SO_2$—$NR_1R_2$, —$SO_3H$, —O—$SO_2$—$OR_3$, —O—P(=O)—$(OR_3)(OR_4)$, —O—$CH_2$—$COOR_3$, $(C_1$-$C_3)$ alkyl, the alkyl being optionally mono- or di-substituted by a hydroxyl group, a group of formula (IIa):

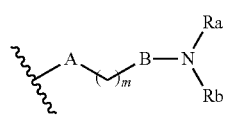

or a group of formula (IIIa):

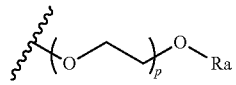

Q is N or O, provided that R″ does not exist when Q is O;

each of $R_1$ and $R_2$ is independently hydrogen or $(C_1$-$C_3)$ alkyl;

each of $R_3$ and $R_4$ is independently hydrogen, $Li^+$, $Na^+$, $K^+$, $N^+(Ra)_4$ or benzyl;

n is 1, 2 or 3;

n' is 1, 2 or 3;

each R' is independently hydrogen, $(C_1$-$C_3)$alkyl, hydroxyl, halogen, —$NO_2$, —$NR_1R_2$, morpholinyl, morpholino, N-methylpiperazinyl, $(C_1$-$C_3)$fluoroalkyl, $(C_1$-$C_4)$alkoxy, —O—P(=O)—$(OR_3)(OR_4)$, —CN, a —NH—$SO_2$—$N(CH_3)_2$ group, a group of formula (IIa):

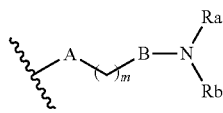

or a group of formula (IIIa):

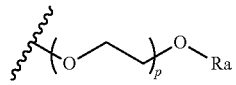

A is a covalent bond, oxygen, or NH;

B is a covalent bond or NH;

m is 1, 2, 3, 4 or 5;

p is 1, 2 or 3;

each of Ra and Rb is independently hydrogen, $(C_1$-$C_5)$ alkyl, or $(C_3$-$C_6)$cycloalkyl, or Ra and Rb form together with the nitrogen atom to which Ra and Rb are attached a saturated 5- or 6-membered heterocycle, the heterocycle optionally containing a further heteroatom chosen among N, O, S, the heterocycle being optionally substituted by one or more Ra, provided that when R' is a group (IIa) or (IIIa), n' may be 2 or 3 only if other R' groups are different from the group (IIa) or (IIIa); and wherein the compound of formula (I) is administered together with one or more JAK-inhibitor, and wherein the inflammatory disease, disorder or condition being treated by the administration of the compound of formula (I) is selected from the group consisting of:

(a) an inflammatory disease, disorder, or condition in the pancreas selected from diabetes type-1, diabetes type-2, acute and chronic pancreatitis;

(b) an inflammatory disease, disorder, or condition in the kidney selected from glomerulosclerosis, glomerulonephritis, nephritis, acute kidney injury, Berger's disease, Goodpasture's syndrome, Wegener's granulomatosis and kidney transplant acute or chronic rejection;

(c) an inflammatory disease, disorder or condition in the liver selected from nonalcoholic steatohepatitis (NASH), non-alcoholic fatty liver disease (NAFLD), cholestatic liver disease, sclerosing cholangitis and liver transplant acute or chronic rejection;

(d) an inflammatory disease, disorder, or condition in the lung or heart selected from chronic obstructive pulmonary disease (COPD), pulmonary fibrosis, pulmonary hypertension, sarcoidosis, myocarditis, pericarditis and lung or heart transplant acute or chronic rejection;

(e) an inflammatory disease, disorder, or condition in the skin selected from contact dermatitis, atopic dermatitis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, acnea and keloid scar;

(f) an inflammatory disease, disorder, or condition in the vessel/blood selected from Behcet's disease, vasculitis, sepsis, tumor angiogenesis, proliferative vascular disease and restenosis;

(g) an inflammatory disease, disorder, or condition in the eye selected from conjunctivitis, scleritis, episcleritis, panuveitis, choroiditis, chorioretinitis, neuroretinitis, uveitis, orbital inflammatory disease, and optical neuritis;

(h) an inflammatory disease, disorder, or condition in the central or peripheral nervous system selected from non-viral and viral encephalitis and meningitis, depression, neuropathic pain, traumatic brain injury, Myelitis, Charcot-Marie-Tooth disease type 1, Amyotrophic lateral sclerosis (ALS), Creutzfeldt-Jakob disease, demyelinating polyneuropathy and peripheral neuropathy;

(i) an autoimmune disease, disorder, or condition selected from Lupus, Guillain-Barre syndrome, Myasthenia gravis, Hashimoto's thyroiditis, idiopathic purpura, aplastic anemia, Graves disease, and Myocarditis;

(k) an inflammatory disease, disorder, or condition in the reproductive system selected from endometriosis, uterine fibroma, prostate dysplasia or growth, and cervix dysplasia; and (l) an inflammatory disease, disorder, or condition in the bone and/or joints selected from juvenile idiopathic arthritis, psoriatic arthritis, periodontitis, and hand, foot, ankle, knee, hip, shoulder, elbow or spine arthritis and/or demineralization.

12. The method according to claim 11, wherein the compound of formula (I) is administered together with tofacitinib.

13. The method according to claim 11, wherein the compound of formula (I) is a compound of formula (Ib):

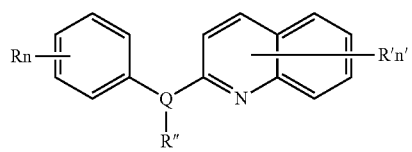

or a metabolite or a pharmaceutically acceptable salt thereof and is administered together with one or more JAK-inhibitor.

14. The method according to claim 11, wherein the compound of formula (I) is a compound of formula (Ib):

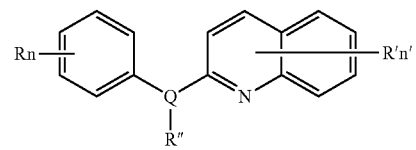

or a metabolite or pharmaceutically acceptable salt thereof and is administered together with tofacitinib.

15. The method according to claim 2, wherein the compound of formula (IV) is administered together with one or more JAK-inhibitor.

16. The method according to claim 2, wherein the compound of formula (IV) is administered together with tofacitinib.

17. The method according to claim 4, wherein the compound of formula (IVb') is

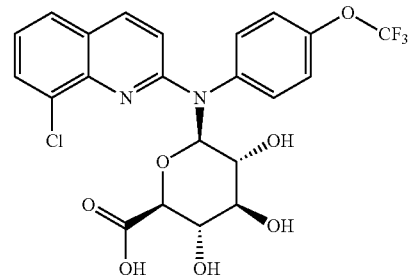 [SMILES: O=C(O)[C@H]1O[C@@H](N(c2ccc(OC(F)(F)F)cc2)c2ccc3cccc(Cl)c3n2)[C@H](O)[C@@H](O)[C@@H]1O]

and is administered together with one or more JAK-inhibitor.

18. The method according to claim 4, wherein the compound of formula (IVb') is

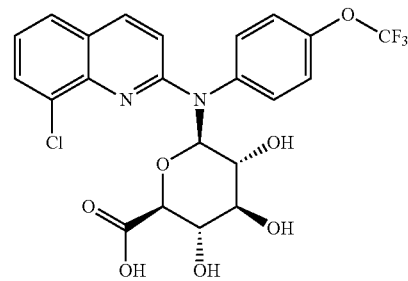 [SMILES: O=C(O)[C@H]1O[C@@H](N(c2ccc(OC(F)(F)F)cc2)c2ccc3cccc(Cl)c3n2)[C@H](O)[C@@H](O)[C@@H]1O]

and is administered together with tofacitinib.

19. A pharmaceutical composition comprising a compound of formula (I):

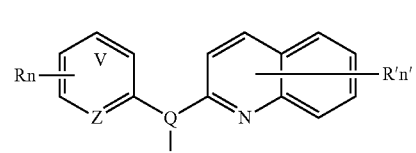

or a metabolite or a pharmaceutically acceptable salt thereof, and
one or more JAK-inhibitor, wherein:
Z is C or N;
V is C or N;

means an aromatic ring, wherein V is C or N, and when V is N, V is ortho, meta or para relative to Z;
each R is independently hydrogen, halogen, —CN, hydroxyl, $(C_1-C_3)$fluoroalkyl, $(C_1-C_3)$fluoroalkoxy, $(C_3-C_6)$cycloalkyl, —NO$_2$, —NR$_1$R$_2$, $(C_1-C_4)$alkoxy, phenoxy, —NR$_1$—SO$_2$—NR$_1$R$_2$, —NR$_1$—SO$_2$—R1, —NR$_1$—C(=O)—R$_1$, —NR$_1$—C(=O)—NR$_1$R$_2$, —SO$_2$—NR$_1$R$_2$, —SO$_3$H, —O—SO$_2$—OR$_3$, —O—P(=O)—(OR$_3$)(OR$_4$), —O—CH$_2$—COOR$_3$, $(C_1-C_3)$ alkyl, the alkyl being optionally mono- or di-substituted by a hydroxyl group or a group of formula (IIa):

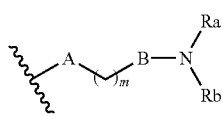

or a group of formula (IIIa):

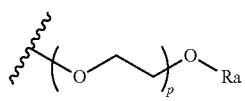

Q is N or O, provided that R" does not exist when Q is O;
each of R$_1$ and R$_2$ is independently hydrogen or $(C_1-C_3)$ alkyl;
each of R$_3$ and R$_4$ is independently hydrogen, Li$^+$, Na$^+$, K$^+$, N$^+$(Ra)$_4$ or benzyl;
n is 1, 2 or 3;
n' is 1, 2 or 3;
each R' is independently hydrogen, $(C_1-C_3)$alkyl, hydroxyl, halogen, —NO$_2$, —NR$_1$R$_2$, morpholinyl, morpholino, N-methylpiperazinyl, $(C_1-C_3)$fluoroalkyl, $(C_1-C_4)$alkoxy, —O—P(=O)—(OR$_3$)(OR$_4$), —CN, a —NH—SO$_2$—N(CH$_3$)$_2$ group, a group of formula (IIa):

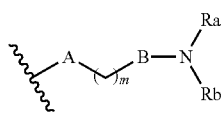

or a group of formula (IIIa):

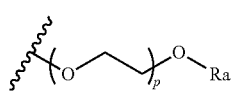

A is a covalent bond, oxygen, or NH;
B is a covalent bond or NH;

m is 1, 2, 3, 4 or 5;
p is 1, 2 or 3;
each of Ra and Rb is independently hydrogen, $(C_1-C_5)$ alkyl, or $(C_3-C_6)$cycloalkyl, or Ra and Rb form together with the nitrogen atom to which Ra and Rb are attached a saturated 5- or 6-membered heterocycle, the heterocycle optionally containing a further heteroatom chosen among N, O, S, the heterocycle being optionally substituted by one or more Ra, provided that when R' is a group (IIa) or (IIIa), n' may be 2 or 3 only if other R' groups are different from the group (IIa) or (IIIa); and
R" is hydrogen, $(C_1-C_4)$alkyl, or a group of formula (IIa) as defined herein.

20. The pharmaceutical composition according to claim 19, wherein the one or more JAK-inhibitor includes tofacitinib.

21. The pharmaceutical composition according to claim 19, wherein the compound is of formula (Ib'):

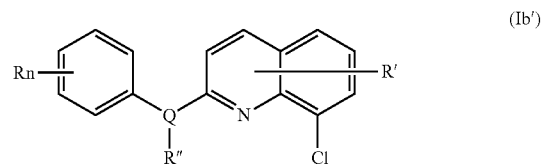

or a metabolite or a pharmaceutically acceptable salt thereof.

22. The pharmaceutical composition according to claim 19, wherein:
the compound of formula (I) is 8-Chloro-N-(4-(trifluoromethoxy)phenyl)quinolin-2-amine, and
the one or more JAK-inhibitor is tofacitinib.

23. A pharmaceutical composition comprising a compound of formula (IV):

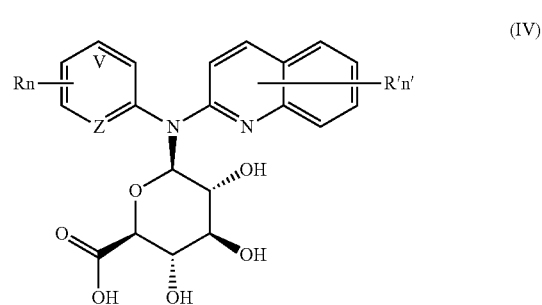

or a pharmaceutically acceptable salt thereof, and
one or more JAK-inhibitor,
wherein:
Z is C or N;
V is C or N;

means an aromatic ring, wherein V is C or N, and when V is N, V is ortho, meta or para relative to Z;

each R is independently hydrogen, halogen, —CN, hydroxyl, $(C_1-C_3)$fluoroalkyl, $(C_1-C_3)$fluoroalkoxy, $(C_3-C_6)$cycloalkyl, —NO$_2$, —NR$_1$R$_2$, $(C_1-C_4)$alkoxy, phenoxy, —NR$_1$—SO$_2$—NR$_1$R$_2$, —NR$_1$—SO$_2$—R1, —NR$_1$—C(=O)—R$_1$, —NR$_1$—C(=O)—NR$_1$R$_2$, —SO$_2$—NR$_1$R$_2$, —SO$_3$H, —O—SO$_2$—OR$_3$, —O—P(=O)—(OR$_3$)(OR$_4$), —O—CH$_2$—COOR$_3$, $(C_1-C_3)$ alkyl, the alkyl being optionally mono- or di-substituted by a hydroxyl group or a group of formula (IIa):

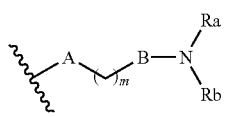

or a group of formula (IIIa):

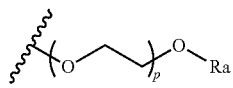

each of R$_1$ and R$_2$ is independently hydrogen or $(C_1-C_3)$ alkyl;
each of R$_3$ and R$_4$ is independently hydrogen, Li$^+$, Na$^+$, K$^+$, N$^+$(Ra)$_4$ or benzyl;
n is 1, 2 or 3;
n' is 1, 2 or 3;
each R' is independently hydrogen, $(C_1-C_3)$alkyl, hydroxyl, halogen, —NO$_2$, —NR$_1$R$_2$, morpholinyl, morpholino, N-methylpiperazinyl, $(C_1-C_3)$fluoroalkyl, $(C_1-C_4)$alkoxy, —O—P(=O)—(OR$_3$)(OR$_4$), —CN, a —NH—SO$_2$—N(CH$_3$)$_2$ group, a group of formula (IIa):

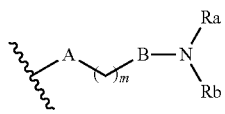

or a group of formula (IIIa):

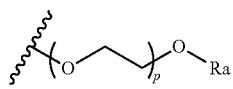

A is a covalent bond, oxygen, or NH;
B is a covalent bond or NH;
m is 1, 2, 3, 4 or 5;
p is 1, 2 or 3;
each of Ra and Rb is independently hydrogen, $(C_1-C_5)$ alkyl, or $(C_3-C_6)$cycloalkyl, or Ra and Rb form together with the nitrogen atom to which Ra and Rb are attached a saturated 5- or 6-membered heterocycle, the heterocycle optionally containing a further heteroatom chosen among N, O, S, the heterocycle being optionally substituted by one or more Ra, provided that when R' is a group (IIa) or (IIIa), n' may be 2 or 3 only if other R' groups are different from the group (IIa) or (IIIa); and R" is hydrogen, $(C_1-C_4)$alkyl, or a group of formula (IIa) as defined herein.

24. The pharmaceutical composition according to claim 23, wherein the one or more JAK-inhibitor includes tofacitinib.

25. The pharmaceutical composition according to claim 23, wherein the compound is:

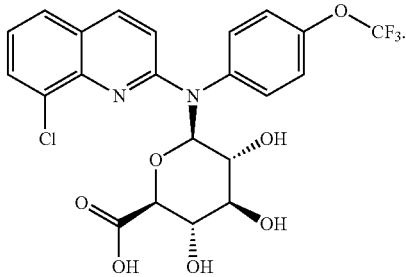 [SMILES: O=C(O)[C@H]1O[C@@H](N(c2ccc(OC(F)(F)F)cc2)c2ccc3cccc(Cl)c3n2)[C@H](O)[C@@H](O)[C@@H]1O]

26. The pharmaceutical composition according to claim 25, wherein the one or more JAK-inhibitor includes tofacitinib.

27. The method according to claim 11, wherein the compound of formula (I) is a compound of formula (Ib'):

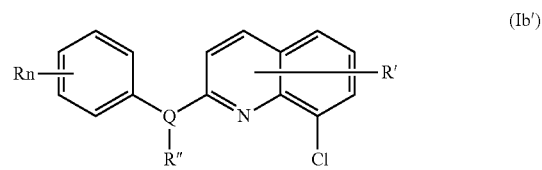

(Ib')

or a metabolite or a pharmaceutically acceptable salt thereof, and is administered together with one or more JAK-inhibitor.

28. The method according to claim 11, wherein the compound of formula (I) is a compound of formula (Ib'):

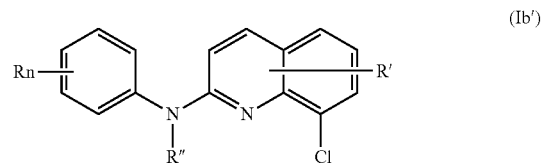

(Ib')

or a metabolite or a pharmaceutically acceptable salt thereof, and is administered together with tofacitinib.

29. The method according to claim 11, wherein the compound of formula (I) is chosen among:

96

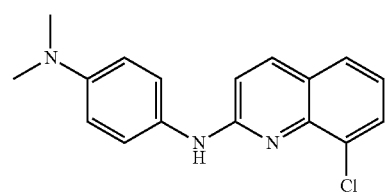

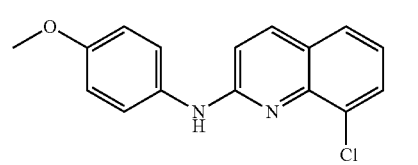
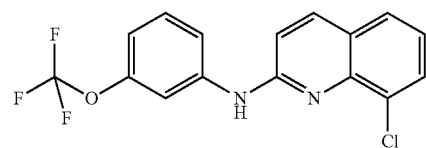
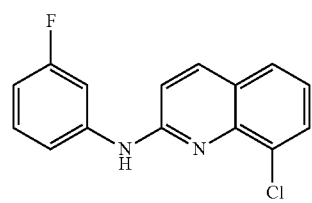
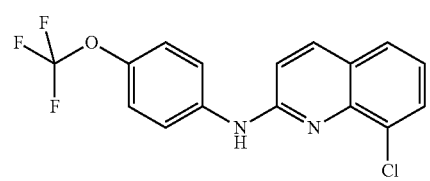
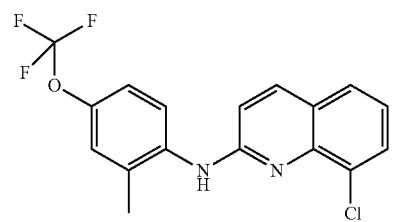
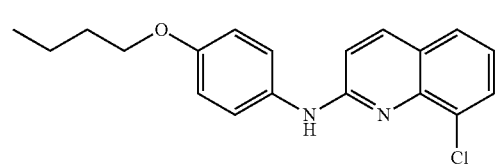
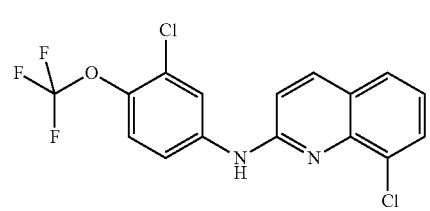
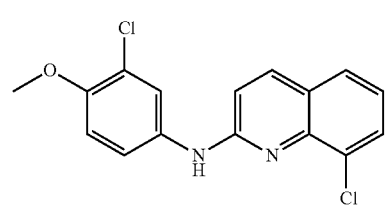
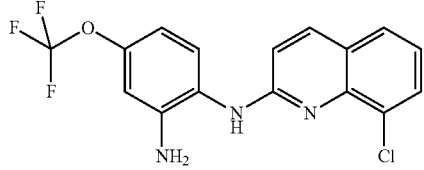

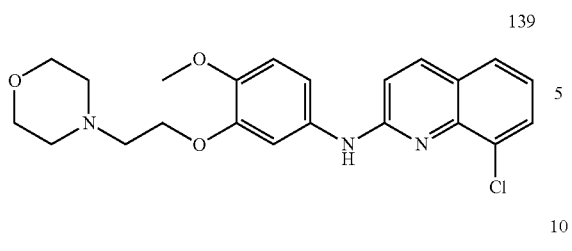
139
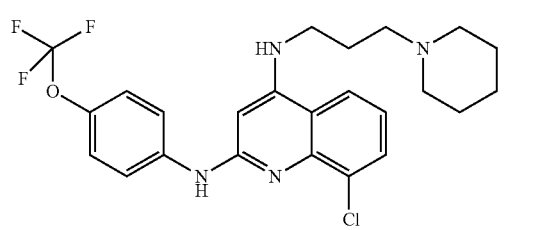
148
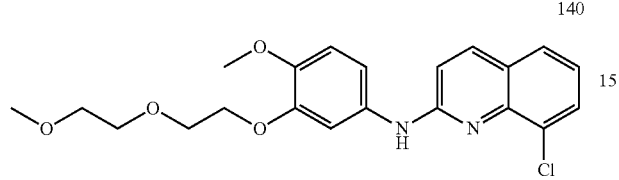
140
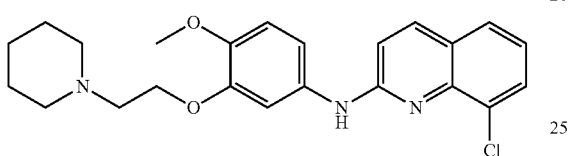
141
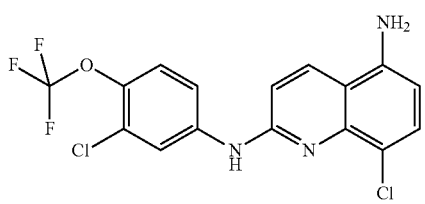
143
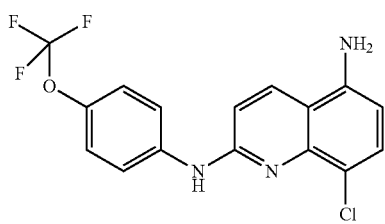
145
149
150
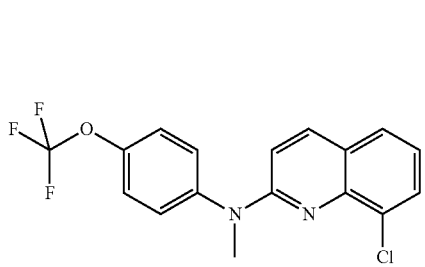
146
151
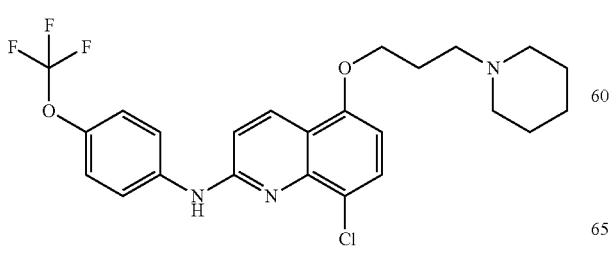
147
152

153 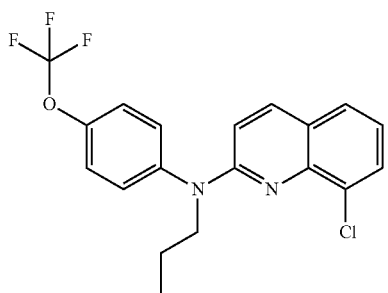
154 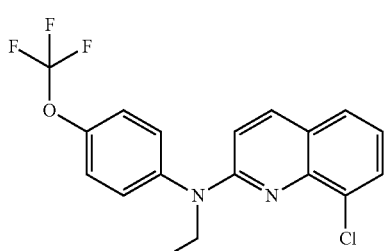
155 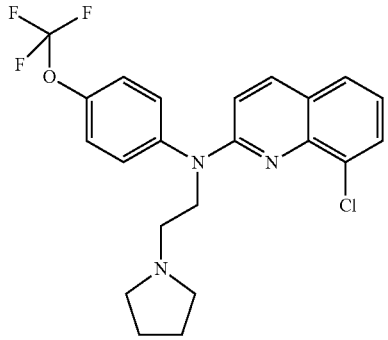
156 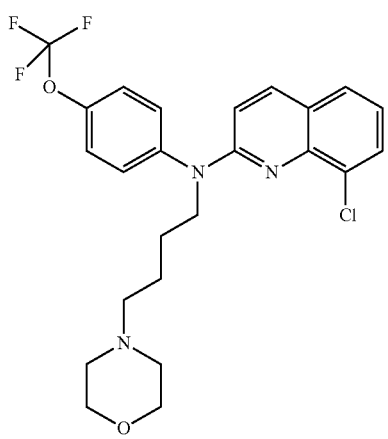
157 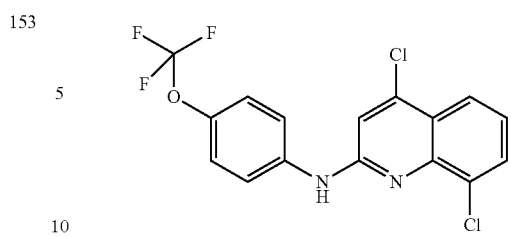
158 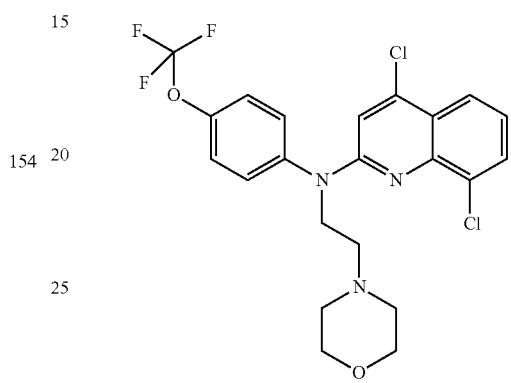
159 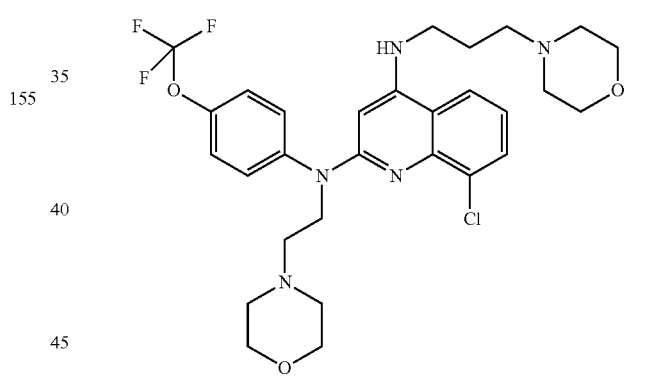
160 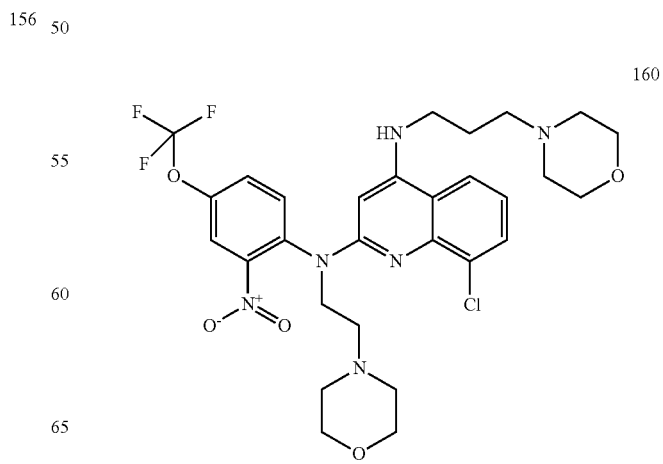

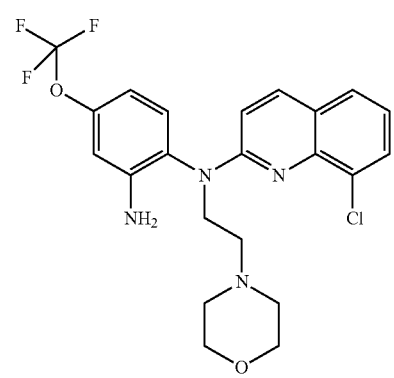
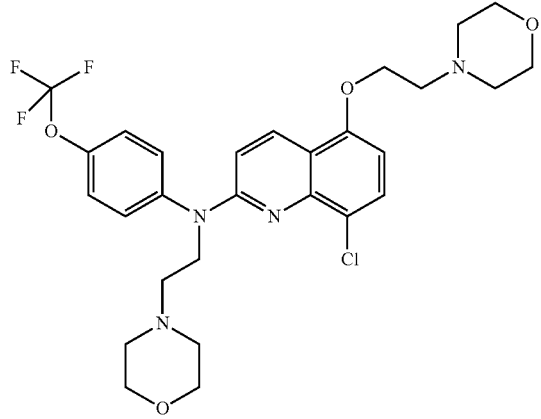
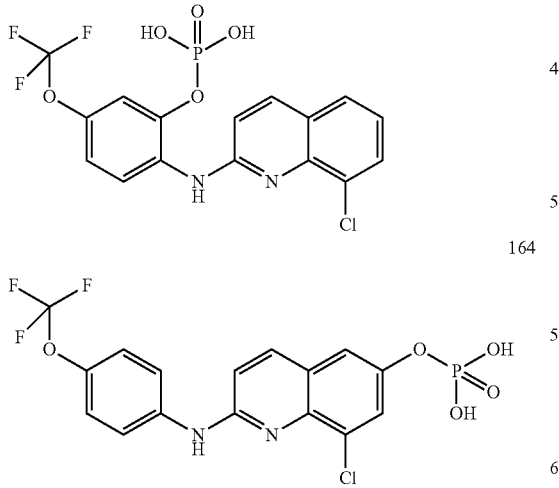
or a metabolite or a pharmaceutically acceptable salt thereof, and
is administered together with one or more JAK-inhibitor.
30. The method according to claim 11, wherein the compound of formula (I) is chosen among:
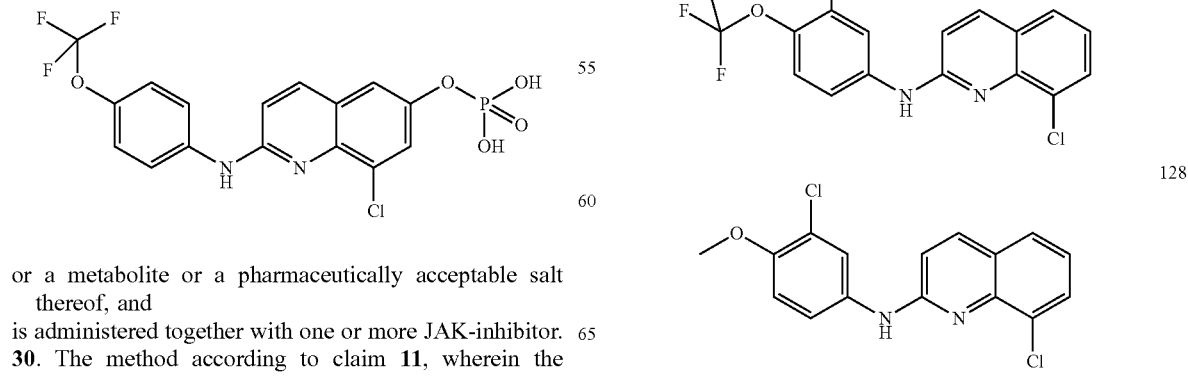

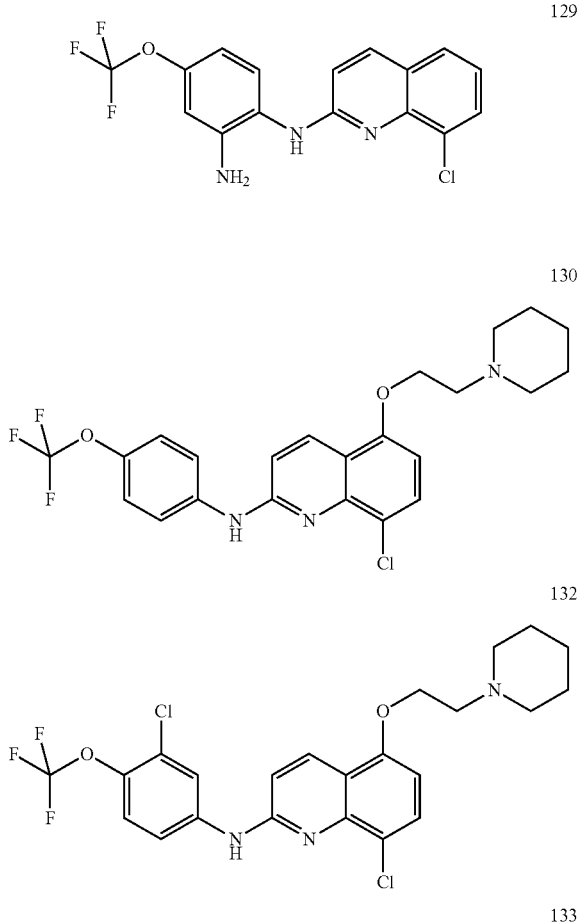
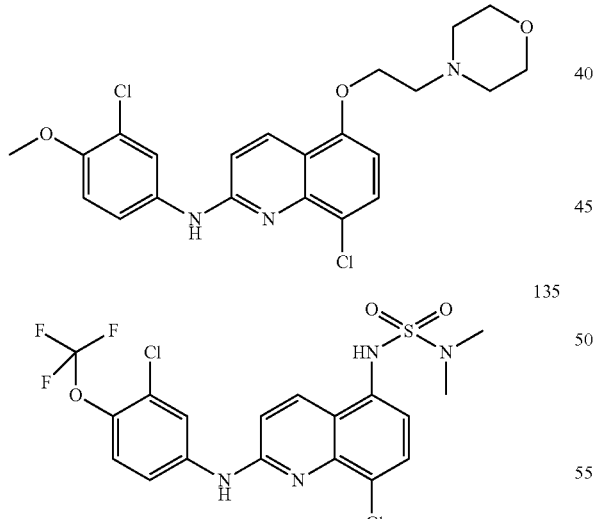
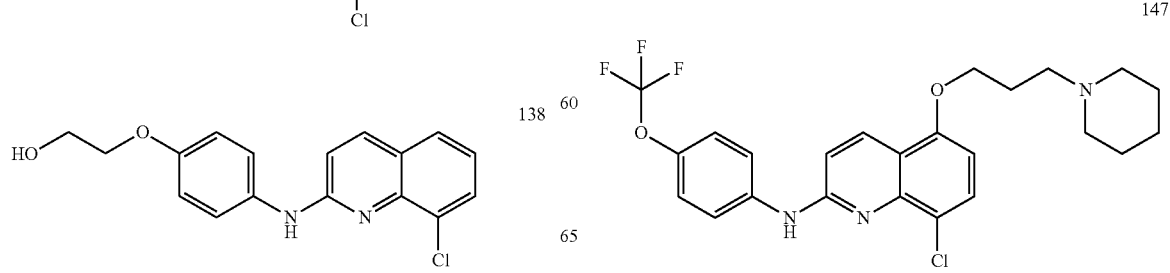

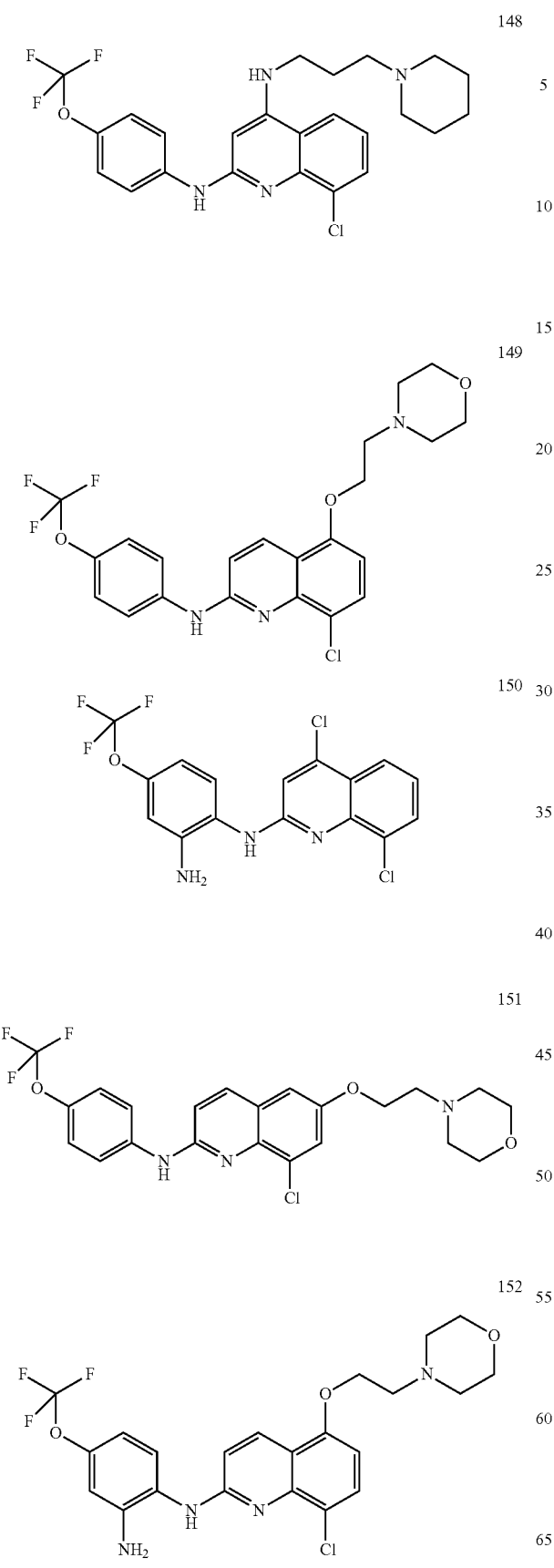
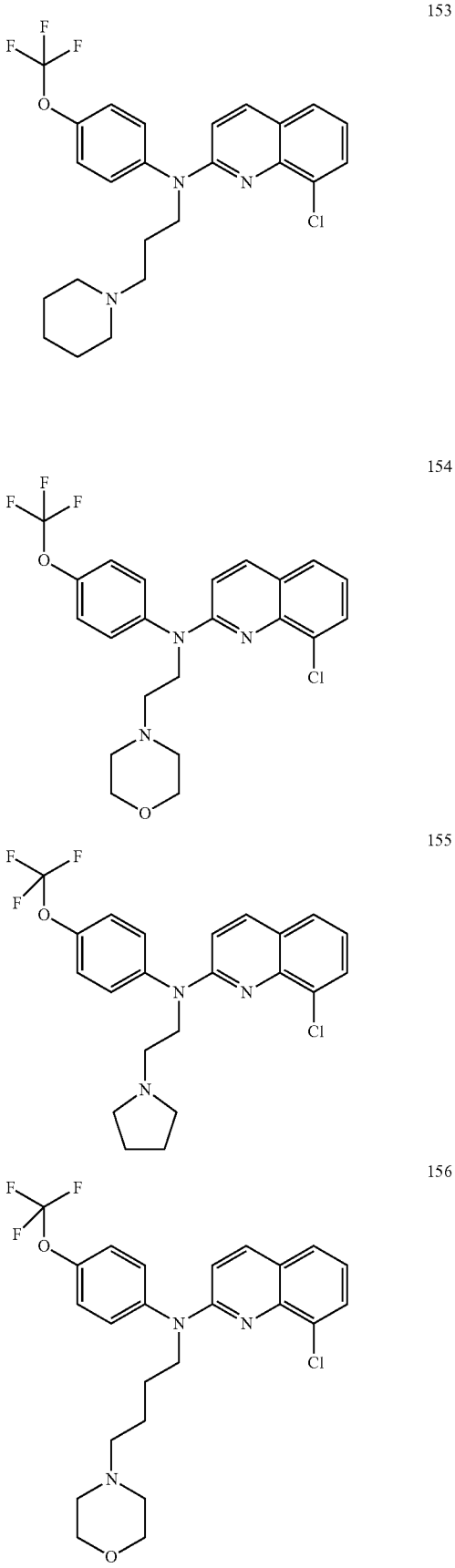

157

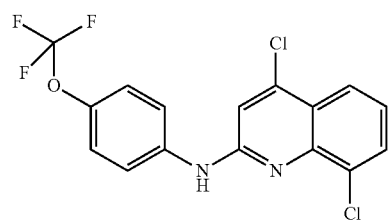

158

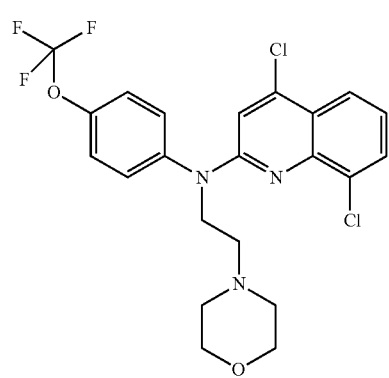

159

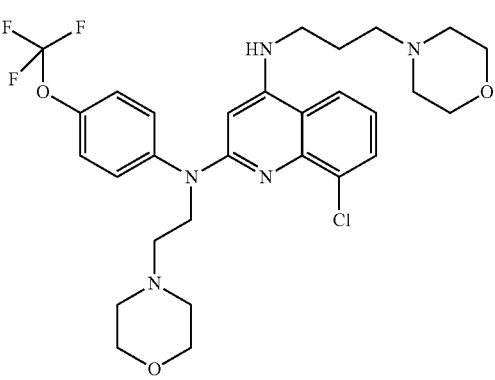

160

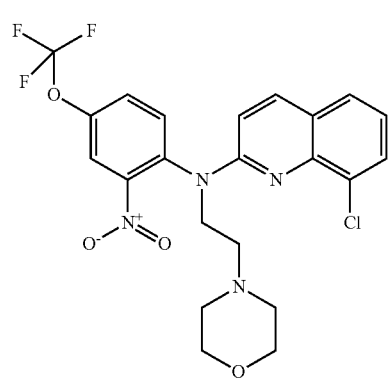

161

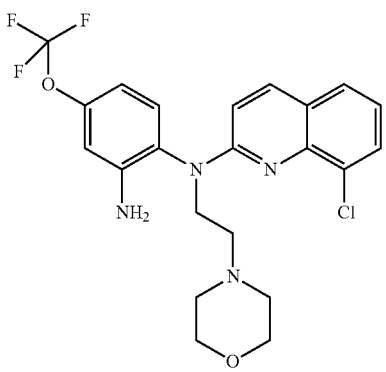

162

163

164 or a metabolite or a pharmaceutically acceptable salt thereof, and
is administered together with tofacitinib.

31. The method according to claim 11, wherein the compound of formula (I) is 8-Chloro-N-(4-(trifluoromethoxy)phenyl)quinolin-2-amine and is administered together with one or more JAK-inhibitor.

32. The method according to claim 11, wherein the compound of formula (I) is 8-Chloro-N-(4-(trifluoromethoxy)phenyl)quinolin-2-amine and is administered together with tofacitinib.

33. The pharmaceutical composition according to claim 19, wherein the compound is of formula (Ib):

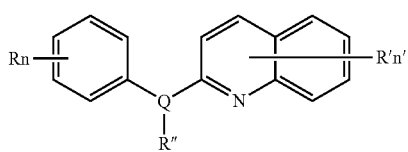
(Ib)

or a metabolite or a pharmaceutically acceptable salt thereof.

34. The pharmaceutical composition according to claim 19, wherein the compound is of formula (Ib):

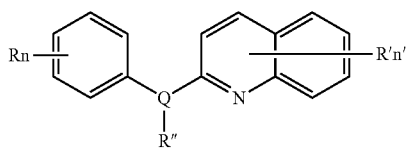
(Ib)

or a metabolite or a pharmaceutically acceptable salt thereof, and the one or more JAK-inhibitor includes tofacitinib.

35. The pharmaceutical composition according to claim 19, wherein the compound is of formula (Ib'):

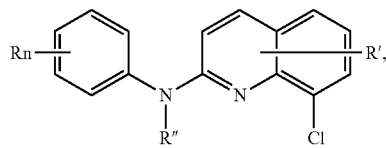
(Ib')

or a metabolite or a pharmaceutically acceptable salt thereof, and the one or more JAK-inhibitor includes tofacitinib.

36. The pharmaceutical composition according to claim 19, wherein the compound of formula (I) is 8-Chloro-N-(4-(trifluoromethoxy)phenyl)quinolin-2-amine.

37. The pharmaceutical composition according to claim 19, wherein the compound of formula (I) is chosen among:

96
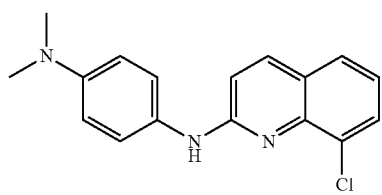

98
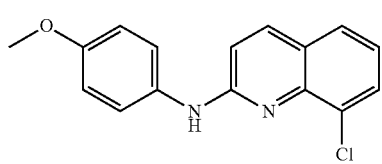

-continued

108

109
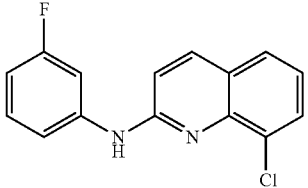

115
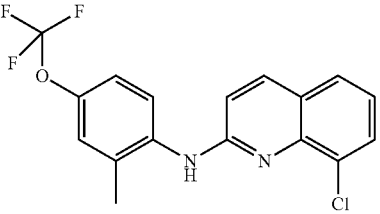

122
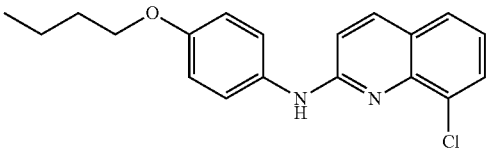

125
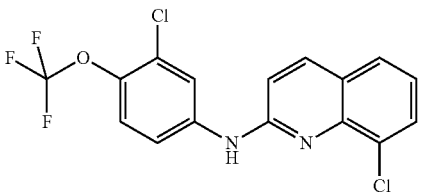

128
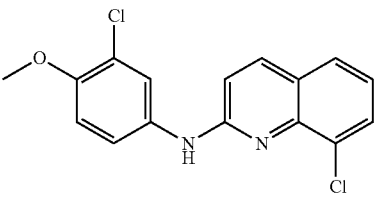

129
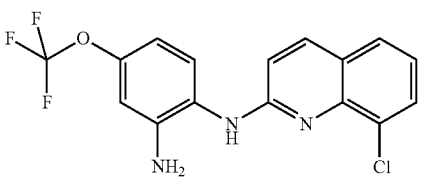

130
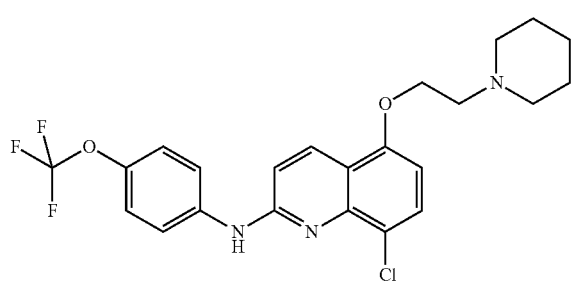

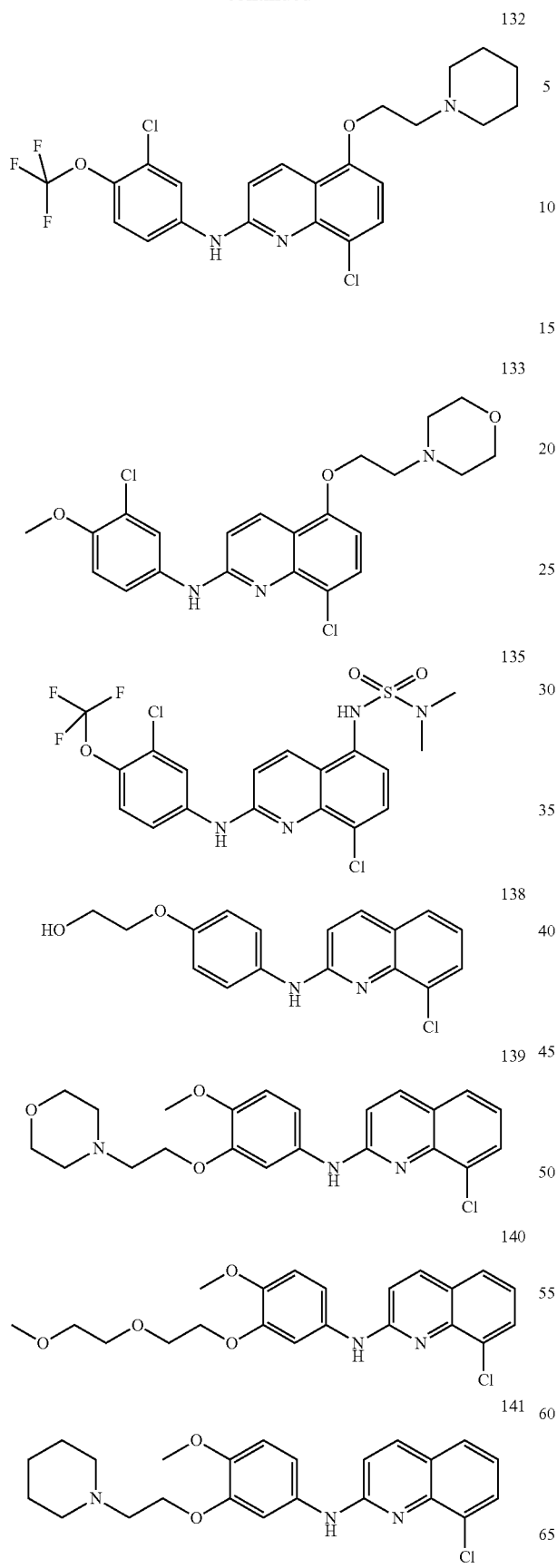
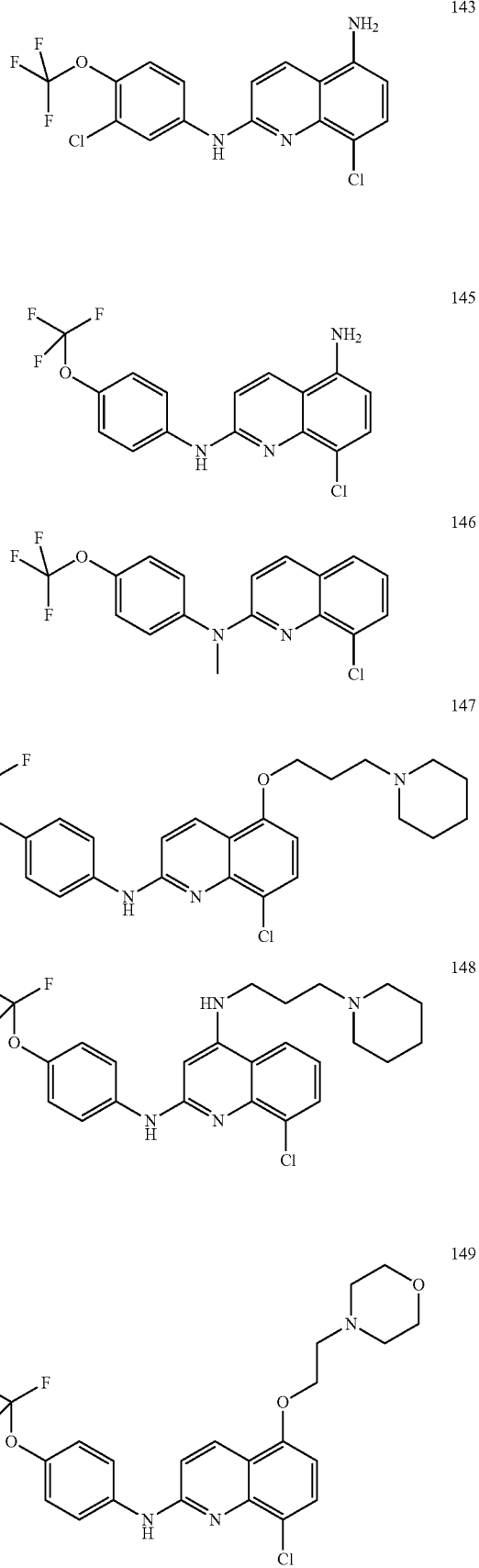

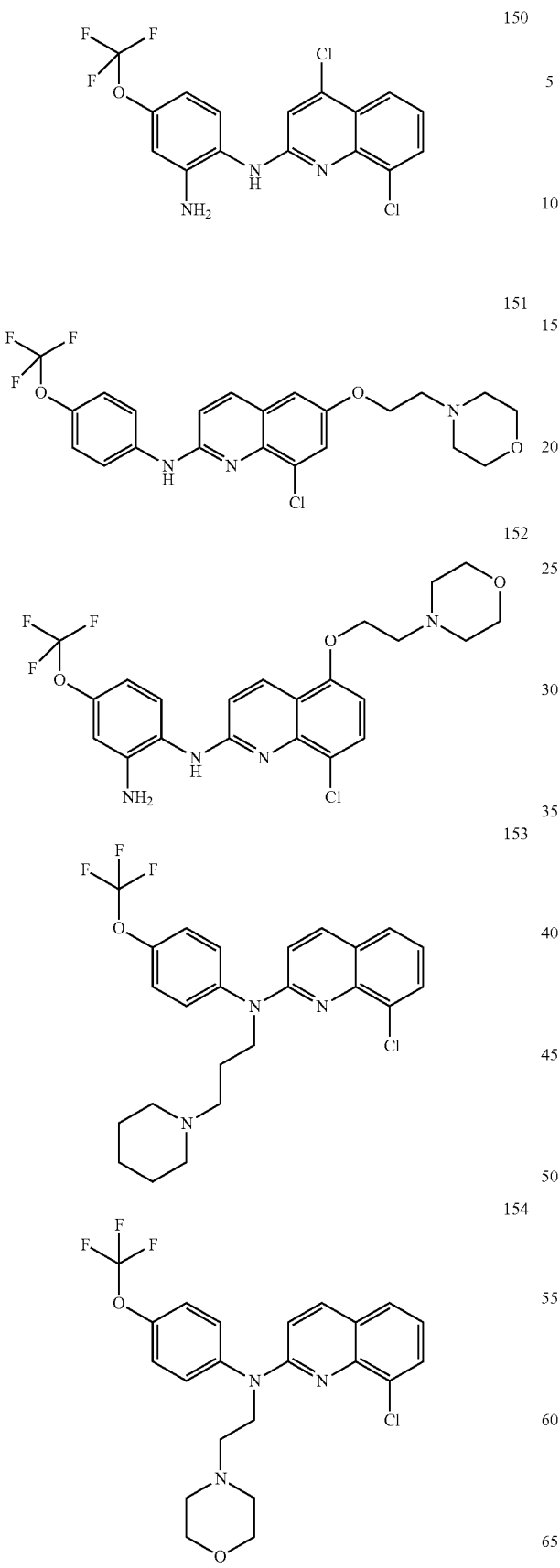
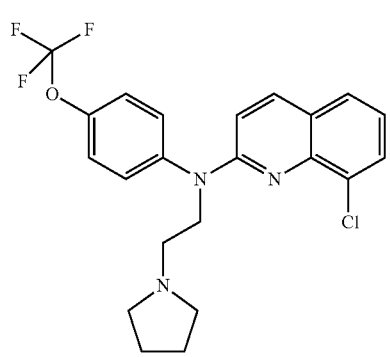
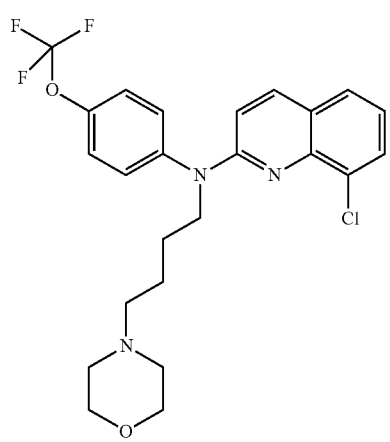
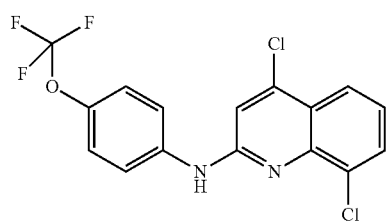
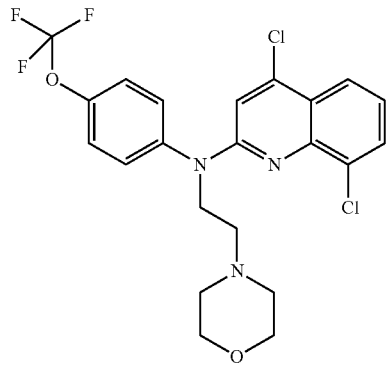

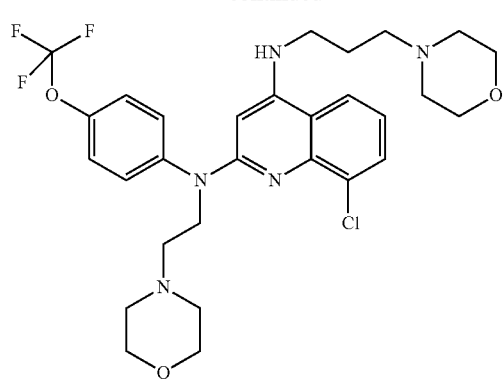
159
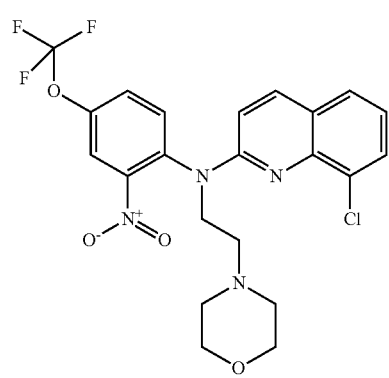
160
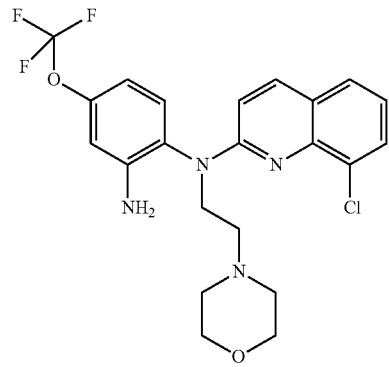
161
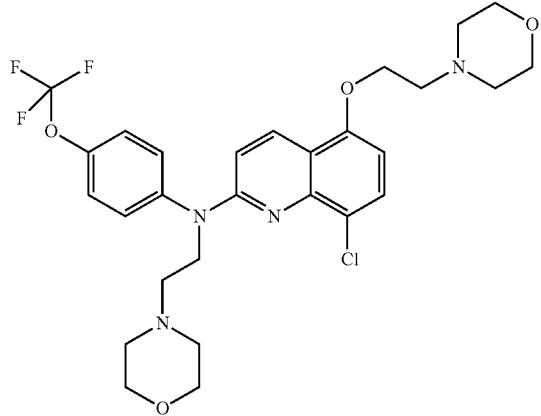
162
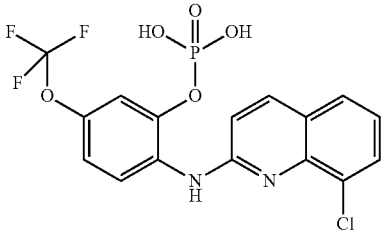
163
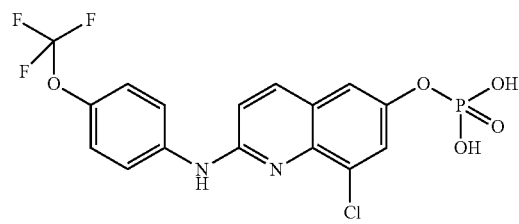
164
or a metabolite or a pharmaceutically acceptable salt thereof.
38. The pharmaceutical composition according to claim 19, wherein the compound of formula (I) is chosen among:
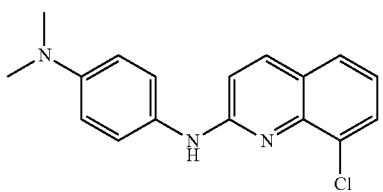
96
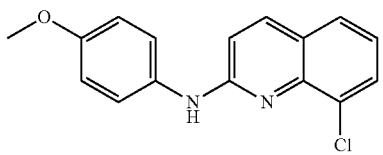
98
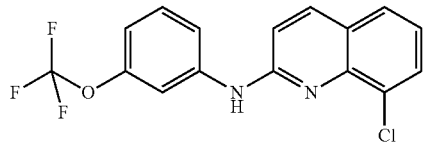
108
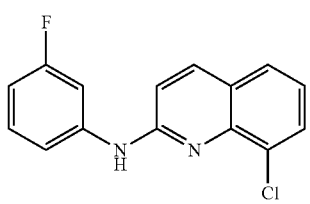
109
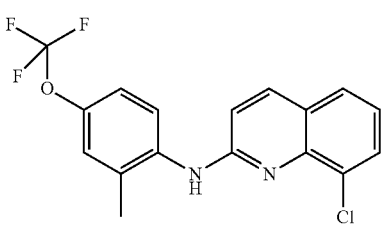
115

-continued

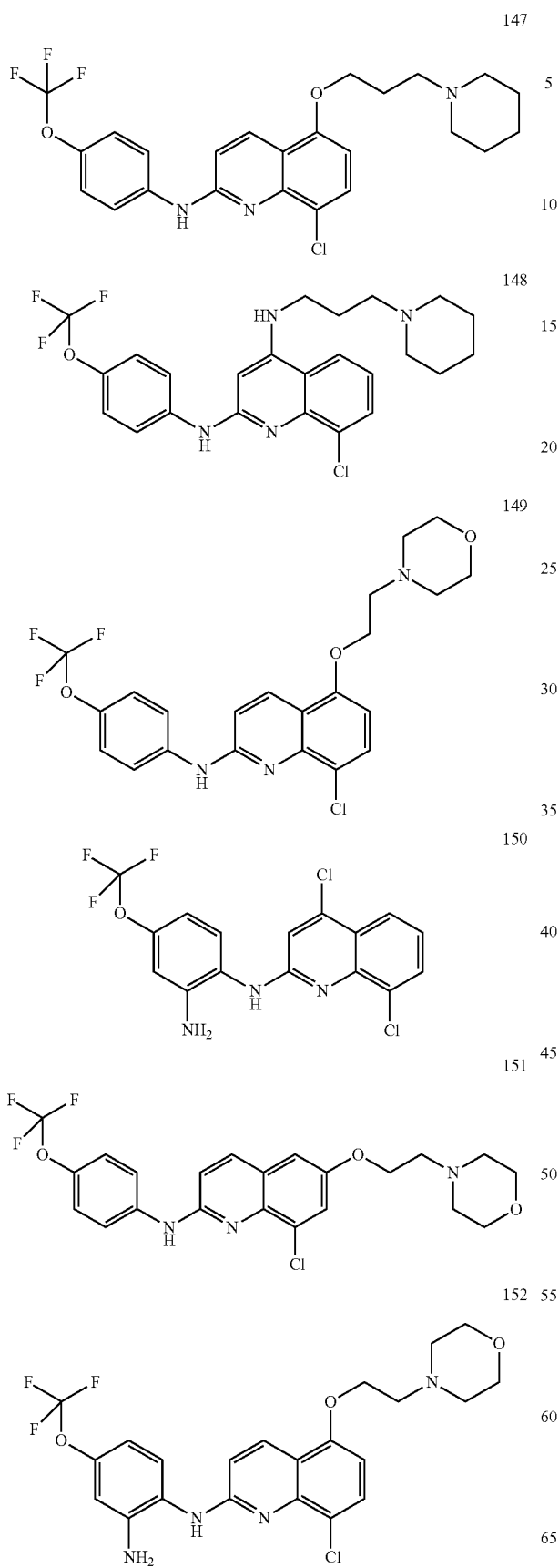
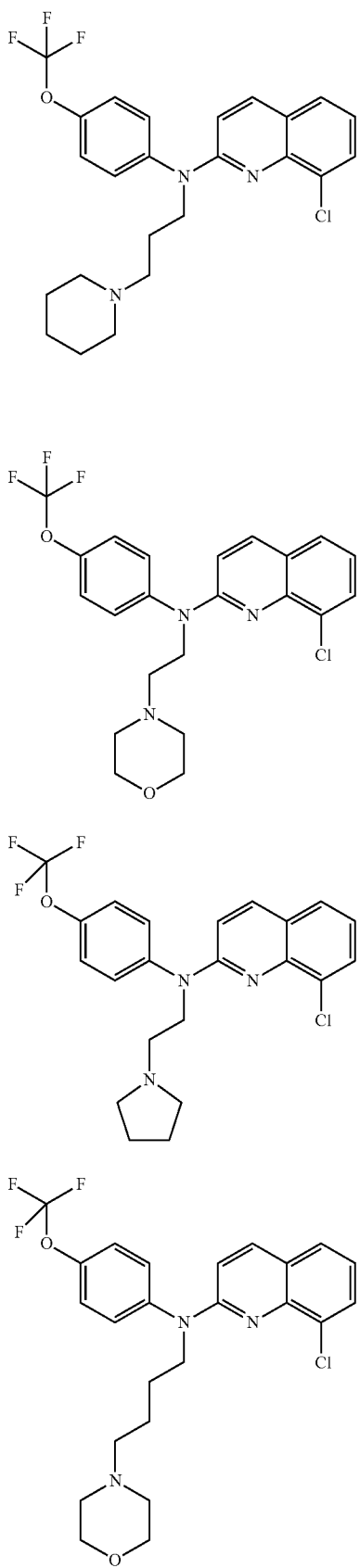

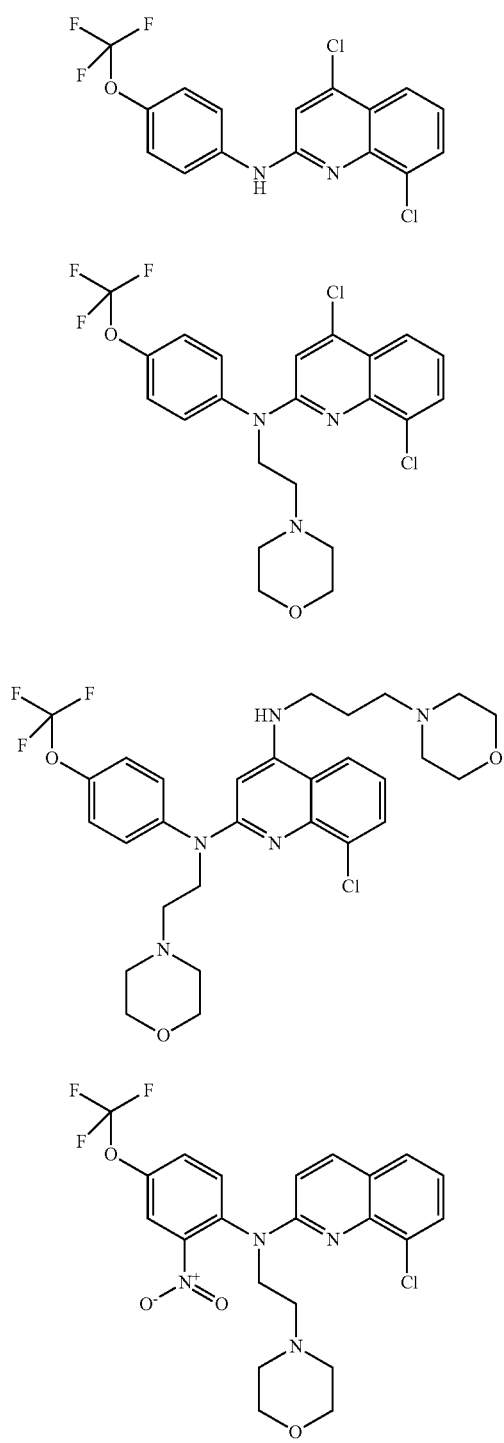
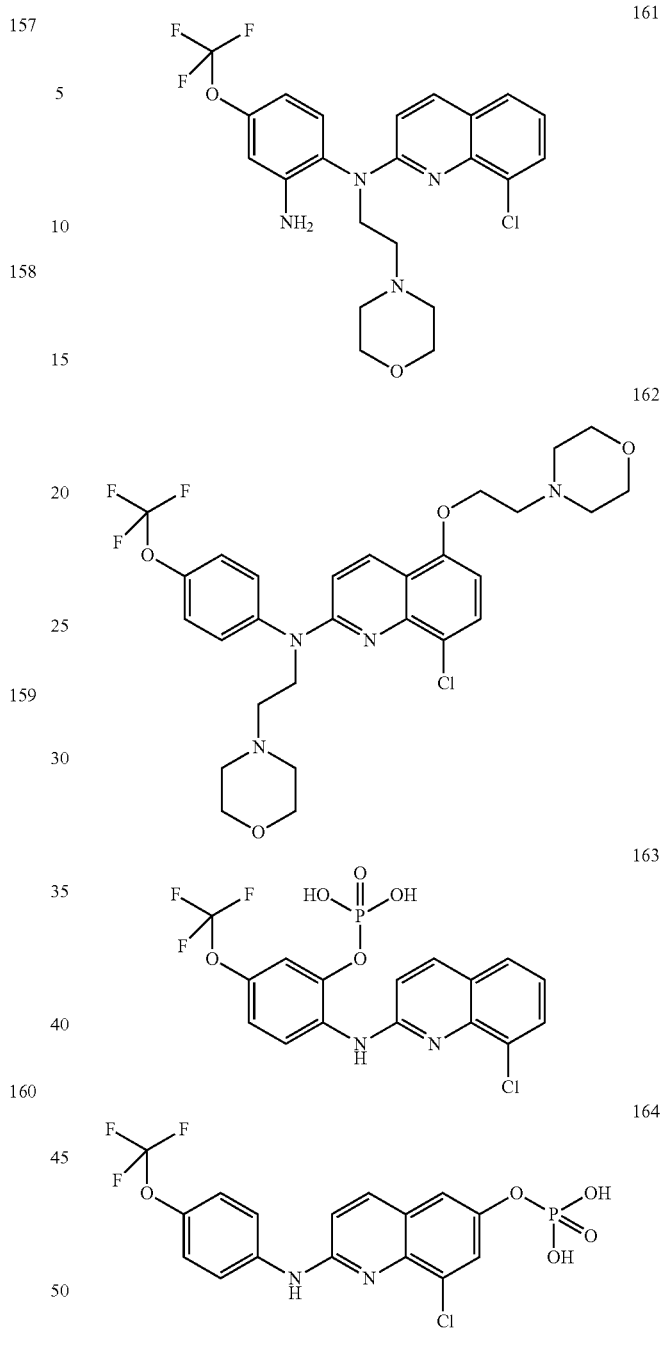
or a metabolite or a pharmaceutically acceptable salt thereof, and
the one or more JAK-inhibitor includes tofacitinib.
* * * * *